US010172875B2

(12) United States Patent
Ponte et al.

(10) Patent No.: US 10,172,875 B2
(45) Date of Patent: Jan. 8, 2019

(54) THERAPEUTIC COMBINATIONS COMPRISING ANTI-FOLR1 IMMUNOCONJUGATES

(71) Applicant: ImmunoGen, Inc., Waltham, MA (US)

(72) Inventors: Jose Ponte, Weymouth, MA (US); Jan Pinkas, Belmont, MA (US); Rodrigo R. Ruiz-Soto, Boston, MA (US)

(73) Assignee: ImmunoGen, inc., Waltham, MA (US)

( * ) Notice: Subject to any disclaimer, the term of this patent is extended or adjusted under 35 U.S.C. 154(b) by 0 days.

(21) Appl. No.: 15/268,298

(22) Filed: Sep. 16, 2016

(65) Prior Publication Data

US 2017/0095571 A1  Apr. 6, 2017

Related U.S. Application Data

(60) Provisional application No. 62/220,028, filed on Sep. 17, 2015, provisional application No. 62/242,669, filed on Oct. 16, 2015, provisional application No. 62/250,756, filed on Nov. 4, 2015.

(51) Int. Cl.
*A61K 39/395* (2006.01)
*A61K 31/704* (2006.01)
*A61K 45/06* (2006.01)
*C07K 16/28* (2006.01)
*A61K 31/555* (2006.01)
*A61K 33/24* (2006.01)
*A61K 47/68* (2017.01)
*A61K 39/00* (2006.01)

(52) U.S. Cl.
CPC .......... *A61K 31/704* (2013.01); *A61K 31/555* (2013.01); *A61K 33/24* (2013.01); *A61K 39/3955* (2013.01); *A61K 45/06* (2013.01); *A61K 47/6803* (2017.08); *A61K 47/6849* (2017.08); *A61K 47/6851* (2017.08); *A61K 47/6869* (2017.08); *C07K 16/28* (2013.01); *A61K 2039/507* (2013.01); *A61K 2039/545* (2013.01); *C07K 2317/565* (2013.01)

(58) Field of Classification Search
None
See application file for complete search history.

(56) References Cited

U.S. PATENT DOCUMENTS

| | | |
|---|---|---|
| 4,256,746 A | 3/1981 | Miyashita et al. |
| 4,294,757 A | 10/1981 | Asai et al. |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 5,208,020 A | 5/1993 | Chari et al. |
| 5,416,016 A | 5/1995 | Low et al. |
| 5,416,064 A | 5/1995 | Chari et al. |
| 5,475,092 A | 12/1995 | Chari et al. |
| 5,585,499 A | 12/1996 | Chari et al. |
| 5,720,954 A | 2/1998 | Hudziak et al. |
| 5,846,545 A | 12/1998 | Chari et al. |
| 5,855,866 A | 1/1999 | Thorpe et al. |
| 6,051,230 A | 4/2000 | Thorpe et al. |
| 6,054,297 A | 4/2000 | Carter et al. |
| 6,333,410 B1 | 12/2001 | Chari et al. |
| 6,441,163 B1 | 8/2002 | Chari et al. |
| 6,716,821 B2 | 4/2004 | Zhao et al. |
| 6,884,879 B1 | 4/2005 | Baca et al. |
| 7,033,594 B2 | 4/2006 | Low et al. |
| 7,060,269 B1 | 6/2006 | Baca et al. |
| 7,112,317 B2 | 9/2006 | Thorpe et al. |
| 7,125,541 B2 | 10/2006 | Thorpe et al. |
| 7,169,901 B2 | 1/2007 | Baca et al. |
| 7,276,497 B2 | 10/2007 | Chari et al. |
| 7,297,334 B2 | 11/2007 | Baca et al. |
| 7,365,166 B2 | 4/2008 | Baca et al. |
| 7,368,565 B2 | 5/2008 | Chari et al. |
| 7,465,449 B2 | 12/2008 | Violette et al. |
| 7,473,796 B2 | 1/2009 | Chari et al. |
| 7,622,115 B2 | 11/2009 | Fyfe et al. |
| 7,740,854 B2 | 6/2010 | Low et al. |

(Continued)

FOREIGN PATENT DOCUMENTS

| | | |
|---|---|---|
| CN | 101139613 A | 3/2008 |
| CN | 101440130 A | 5/2009 |

(Continued)

OTHER PUBLICATIONS

Strome et al., The Oncologist, 2007; 12:1084-95 (Year: 2007).*
Brand et al., Anticancer Res. 2006; 26:463-70 (Year: 2006).*
Ab, O., et al., "Anitbody-Maytansinoid Conjugates Targeting Folate Receptor 1 for Cancer Therapy," 2010 EORTC-NCI-AACR Symposium—Berlin, Germany (Nov. 16-19, 2010), Abstract 236, 1 Page, American Association for Cancer Research, Germany (distributed in print Nov. 16, 2010; available online Oct. 29, 2010).
Ab, O., et al., "IMGN853, An Anti-Folate Receptor 1 Antibody-maytansinoid Conjugate for Targeted Cancer Therapy," 102nd Annual AACR Meeting—Orlando, FL (Apr. 2-6, 2011), Abstract 4576, 1 Page, American Association for Cancer Research, United States (distributed in print Mar. 8, 2011; available online Feb. 25, 2011).

(Continued)

*Primary Examiner* — Sheela J. Huff
(74) *Attorney, Agent, or Firm* — Sterne, Kessler, Goldstein & Fox P.L.L.C.

(57) ABSTRACT

Therapeutic combinations of immunoconjugates that bind to FOLR1 (e.g., IMGN853) with anti-VEGF agents (e.g., bevacizumab), a platinum-based agent, and/or doxorubicin are provided. Methods of administering the combinations to treat cancers, e.g., ovarian cancers, with greater clinical efficacy and/or decreased toxicity are also provided.

25 Claims, 12 Drawing Sheets
Specification includes a Sequence Listing.

(56) References Cited

U.S. PATENT DOCUMENTS

| | | | |
|---|---|---|---|
| 7,915,388 B2 | 3/2011 | Wu et al. | |
| 8,124,083 B2 | 2/2012 | Nicolaides et al. | |
| 8,153,126 B2 | 4/2012 | Violette et al. | |
| 8,236,319 B2 | 8/2012 | Chari et al. | |
| 8,557,966 B2 | 10/2013 | Ab et al. | |
| 8,557,996 B2 | 10/2013 | Chaffee et al. | |
| 8,709,432 B2 | 4/2014 | Carrigan et al. | |
| 8,778,340 B2 | 7/2014 | Dupont et al. | |
| 8,795,673 B2 | 8/2014 | Li et al. | |
| 8,834,877 B2 | 9/2014 | O'Shannessy et al. | |
| 9,133,275 B2 | 9/2015 | Ab et al. | |
| 9,200,073 B2 | 12/2015 | Carrigan et al. | |
| 9,598,490 B2 * | 3/2017 | Ab | C07K 16/28 |
| 9,637,547 B2 | 5/2017 | Ab et al. | |
| 9,657,100 B2 | 5/2017 | Ab et al. | |
| 9,670,278 B2 | 6/2017 | Ab et al. | |
| 9,670,279 B2 | 6/2017 | Ab et al. | |
| 9,670,280 B2 * | 6/2017 | Ab | C07K 16/28 |
| 9,702,881 B2 | 7/2017 | Carrigan et al. | |
| 2003/0028009 A1 | 2/2003 | Huse | |
| 2003/0148406 A1 | 8/2003 | King et al. | |
| 2003/0157090 A1 | 8/2003 | Benvenuto et al. | |
| 2003/0229208 A1 | 12/2003 | Queen et al. | |
| 2003/0233675 A1 | 12/2003 | Cao et al. | |
| 2004/0031072 A1 | 2/2004 | La Rosa et al. | |
| 2004/0087478 A1 | 5/2004 | Gillen et al. | |
| 2004/0157214 A1 | 8/2004 | McCafferty et al. | |
| 2004/0170630 A1 | 9/2004 | Huang et al. | |
| 2004/0180386 A1 | 9/2004 | Carr et al. | |
| 2004/0235840 A1 | 11/2004 | Chari et al. | |
| 2005/0025763 A1 | 2/2005 | Williams et al. | |
| 2005/0244901 A1 | 11/2005 | Peschen et al. | |
| 2006/0030524 A1 | 2/2006 | Cohen et al. | |
| 2006/0110771 A1 | 5/2006 | Katagiri et al. | |
| 2006/0228349 A1 | 10/2006 | Acton et al. | |
| 2006/0239910 A1 | 10/2006 | Nicolaides et al. | |
| 2007/0041985 A1 | 2/2007 | Unger et al. | |
| 2007/0048315 A1 | 3/2007 | Presta et al. | |
| 2007/0071675 A1 | 3/2007 | Wu et al. | |
| 2007/0098719 A1 | 5/2007 | Smith et al. | |
| 2007/0099251 A1 | 5/2007 | Zhang et al. | |
| 2007/0231266 A1 | 10/2007 | Low et al. | |
| 2007/0253950 A1 | 11/2007 | Jacobsen | |
| 2007/0286858 A1 | 12/2007 | Clancy et al. | |
| 2007/0294782 A1 | 12/2007 | Abad et al. | |
| 2008/0081047 A1 | 4/2008 | Berry et al. | |
| 2008/0104734 A1 | 5/2008 | Kav et al. | |
| 2008/0131366 A1 | 6/2008 | Ratnam | |
| 2008/0138396 A1 | 6/2008 | Low et al. | |
| 2008/0171014 A1 | 7/2008 | Wu et al. | |
| 2008/0181888 A1 | 7/2008 | Ambrose et al. | |
| 2008/0227704 A1 | 9/2008 | Kamens | |
| 2008/0260748 A1 | 10/2008 | Iwamoto et al. | |
| 2009/0081710 A1 | 3/2009 | Low et al. | |
| 2009/0087478 A1 | 4/2009 | Hansen et al. | |
| 2009/0104215 A1 | 4/2009 | Ekiel et al. | |
| 2009/0136516 A1 | 5/2009 | Tedder et al. | |
| 2009/0156788 A1 | 6/2009 | Presta et al. | |
| 2009/0162374 A1 * | 6/2009 | Geraghty | A61K 39/39541 424/153.1 |
| 2009/0169547 A1 | 7/2009 | Sahin et al. | |
| 2009/0186027 A1 | 7/2009 | Solomon et al. | |
| 2009/0214636 A1 | 8/2009 | Low et al. | |
| 2009/0215165 A1 | 8/2009 | Rance et al. | |
| 2009/0232810 A1 | 9/2009 | Kraus et al. | |
| 2009/0232822 A1 | 9/2009 | Joseloff et al. | |
| 2009/0274697 A1 | 11/2009 | Grasso et al. | |
| 2009/0274713 A1 | 11/2009 | Chari et al. | |
| 2009/0280124 A1 | 11/2009 | Labat et al. | |
| 2009/0280128 A1 | 11/2009 | Kamogawa et al. | |
| 2009/0285795 A1 | 11/2009 | Patell | |
| 2009/0285813 A1 | 11/2009 | Frey et al. | |
| 2009/0317921 A1 | 12/2009 | Groome et al. | |
| 2009/0324491 A1 | 12/2009 | Aburatani et al. | |
| 2009/0324594 A1 | 12/2009 | Nicolaides et al. | |
| 2010/0055034 A1 | 3/2010 | Martin et al. | |
| 2010/0086537 A1 | 4/2010 | Sooknanan et al. | |
| 2010/0087509 A1 | 4/2010 | Van Rompaey et al. | |
| 2010/0092470 A1 | 4/2010 | Bhatt et al. | |
| 2010/0104626 A1 | 4/2010 | Leamon et al. | |
| 2010/0111852 A1 | 5/2010 | Yoshida | |
| 2010/0111866 A1 | 5/2010 | Kratz | |
| 2010/0129314 A1 | 5/2010 | Singh et al. | |
| 2010/0239581 A1 | 9/2010 | Joseloff et al. | |
| 2010/0255479 A1 | 10/2010 | Mikolajczyk et al. | |
| 2010/0272741 A1 | 10/2010 | Knutson et al. | |
| 2010/0323973 A1 | 12/2010 | Leamon et al. | |
| 2010/0330572 A1 | 12/2010 | Assaraf et al. | |
| 2011/0002942 A1 | 1/2011 | Presta et al. | |
| 2011/0021555 A1 | 1/2011 | Nordsiek et al. | |
| 2011/0038867 A1 | 2/2011 | Pincelli et al. | |
| 2011/0059469 A1 | 3/2011 | Aburatani et al. | |
| 2011/0195022 A1 | 8/2011 | Deckert et al. | |
| 2011/0206662 A1 * | 8/2011 | Dupont | A61K 31/282 424/133.1 |
| 2011/0256127 A1 | 10/2011 | Bourhis et al. | |
| 2012/0009181 A1 | 1/2012 | Ab et al. | |
| 2012/0148577 A1 * | 6/2012 | Fuchs | A61K 31/675 424/133.1 |
| 2012/0164137 A1 * | 6/2012 | Sass | C07K 16/00 424/133.1 |
| 2012/0177664 A1 | 7/2012 | Yokoseki et al. | |
| 2012/0183552 A1 | 7/2012 | Joseloff et al. | |
| 2012/0190661 A1 * | 7/2012 | Trogden | A61K 9/00 514/178 |
| 2012/0207771 A1 | 8/2012 | O'Shannessy et al. | |
| 2012/0251532 A1 | 10/2012 | Violette et al. | |
| 2012/0253021 A1 | 10/2012 | Li et al. | |
| 2012/0259100 A1 | 10/2012 | Jin | |
| 2012/0282282 A1 | 11/2012 | Lutz et al. | |
| 2012/0282637 A1 | 11/2012 | Huber et al. | |
| 2013/0039916 A1 | 2/2013 | Presta et al. | |
| 2013/0295119 A1 | 11/2013 | Ab et al. | |
| 2014/0023665 A1 * | 1/2014 | Fishkin | C07D 498/18 424/178.1 |
| 2014/0072587 A1 | 3/2014 | Morariu | |
| 2014/0099332 A1 | 4/2014 | Testa et al. | |
| 2014/0302014 A1 * | 10/2014 | Narain | A61K 31/122 424/133.1 |
| 2014/0363451 A1 | 12/2014 | Running et al. | |
| 2014/0363453 A1 | 12/2014 | Carrigan et al. | |
| 2015/0132323 A1 * | 5/2015 | Lutz | C07K 16/28 424/178.1 |
| 2015/0297744 A1 | 10/2015 | Lutz et al. | |
| 2015/0306242 A1 | 10/2015 | Li et al. | |
| 2016/0060339 A1 | 3/2016 | Ab et al. | |
| 2016/0075781 A1 | 3/2016 | Ab et al. | |
| 2017/0239367 A1 | 8/2017 | Running et al. | |
| 2017/0306041 A1 | 10/2017 | Ab et al. | |
| 2017/0327575 A1 | 11/2017 | Ab et al. | |
| 2018/0003715 A1 | 1/2018 | Carrigan et al. | |

FOREIGN PATENT DOCUMENTS

| | | |
|---|---|---|
| EP | 1900752 A1 | 3/2008 |
| EP | 1864133 B1 | 3/2010 |
| WO | WO-9429351 A2 | 12/1994 |
| WO | WO-9711971 A1 | 4/1997 |
| WO | WO-02071928 A2 | 9/2002 |
| WO | WO-2004110498 A2 | 12/2004 |
| WO | WO-2005003154 A2 | 1/2005 |
| WO | WO-2005080431 A2 | 9/2005 |
| WO | WO-2006105141 A1 | 10/2006 |
| WO | WO-2006116592 A2 | 11/2006 |
| WO | WO-2007006041 A2 | 1/2007 |
| WO | WO-2007020965 A1 | 2/2007 |
| WO | WO-2007094754 A2 | 8/2007 |
| WO | WO-2007147265 A1 | 12/2007 |
| WO | WO-2008021290 A2 | 2/2008 |
| WO | WO-2008031577 A1 | 3/2008 |
| WO | WO-2008072723 A1 | 6/2008 |
| WO | WO-2008101231 A2 | 8/2008 |
| WO | WO-2008103473 A1 | 8/2008 |

(56) References Cited

FOREIGN PATENT DOCUMENTS

| WO | WO-2008145136 A1 | 12/2008 |
|---|---|---|
| WO | WO-2009080759 A1 | 7/2009 |
| WO | WO-2009087978 A1 | 7/2009 |
| WO | WO-2009132081 A2 | 10/2009 |
| WO | WO-2010033733 A1 | 3/2010 |
| WO | WO-2010111388 A2 | 9/2010 |
| WO | WO-2011042548 A1 | 4/2011 |
| WO | WO-2011106528 A1 | 9/2011 |
| WO | WO-2012061759 A2 | 5/2012 |
| WO | WO-2012135675 A2 | 10/2012 |
| WO | WO-2012138749 A1 | 10/2012 |
| WO | WO-2013012722 A1 | 1/2013 |
| WO | WO-2014036495 A2 | 3/2014 |
| WO | WO-2014186403 A2 | 11/2014 |
| WO | WO-2015031815 A3 | 5/2015 |
| WO | WO-2015054400 A3 | 6/2015 |
| WO | WO-2015149018 A1 | 10/2015 |

OTHER PUBLICATIONS

Ab, O., et al., "IMGN853, An Anti-Folate Receptor 1 Antibody-maytansinoid Conjugate for Targeted Cancer Therapy Poster," 102nd Annual AACR Meeting—Orlando, FL (Apr. 2-6, 2011), Abstract 4576, 1 Page, American Association for Cancer Research, United States (distributed in print Mar. 8, 2011; available online Feb. 25, 2011).

Allard, J.E., et al., "Overexpression of Folate Binding Protein is Associated with Shortened Progression-free Survival in Uterine Adenocarcinomas," Gynecologic Oncology 107(1):52-57, Academic Press, United States (2007).

Allen, T.M., et al., "Drug Delivery Systems: Entering the Mainstream," *Science* 303:1818-1822, AAAS, United States (2004).

Antony, A.C., "Folate Receptors," Annual Review of Nutrition 16:501-521, Annual Reviews, United States (1996).

Armstrong, D.K., et al., "Efficacy and Safety of Farletuzumab, a Humanized Monoclonal Antibody to Folate Receptor Alpha, in Platinum-sensitive Relapsed Ovarian Cancer Subjects: Preliminary Data from a Phase-2 Study," European Journal of Cancer Suppl. 7:450, Elsevier Science Ltd., England (2009).

Armstrong, D.K., et al., "Exploratory Phase II Efficacy Study of MORAb-003, a Monoclonal Antibody Against Folate Receptor Alpha, in Platinum-sensitive Ovarian Cancer in First Relapse," Journal of Clinical Oncology Suppl.26:293S, American Society of Clinical Oncology, United States (2008).

Arnal, I. et al., "How does taxol stabilize microtubules?" Current Biology 5:900-908, Cell Press, Unites States (1995).

Avastin® Full Prescribing Information, Genentech Inc., 35 pages (May 2015).

Avastin Official Patient and Caregiver Website, Genentech Inc., 5 pages, Acessed at https://www.avastin.com/patient/mcrc.html accessed on Jan. 12, 2018.

Basal, E., et al., "Functional Folate Receptor Alpha is Elevated in the Blood of Ovarian Cancer Patients," PloS One 4(7):e6292, Public Library of Science, United States (2009).

Baselga, J., et al., "Phase II Study of Weekly Intravenous Recombinant Humanized Anti-p185HER2 Monoclonal Antibody in Patients with HER2/neu Overexpressing Metastatic Breast Cancer," Journal of Clinical Oncology 14(3):737-744, American Society of Clinical Oncology, United States (1996).

Bendig, M.M., "Humanization of Rodent Monoclonal Antibodies by CDR Grafting," Methods: A Companion to Methods in Enzymology 8(2):83-93, Academic Press, United States (1995).

Brown, M., et al., "Tolerance of Single, but Not Multiple, Amino Acid Replacements in AntibodyVH CDR2: A Means of Minimizing B Cell Wastage from Somatic Hypermutation?," Journal of Immunology 156(9):3285-3291, American Association of Immunologists, United States (1996).

Bueno, R., et al., "The Alpha Folate Receptor is Highly Activated in Malignant Pleural Mesothelioma," The Journal of Thoracic and Cardiovascular Surgery 121(2):225-233, Mosby, United States (2001).

Cagle, P.T., et al., "Folate Receptor in Adenocarcinoma and Squamous Cell Carcinoma of the Lung: Potential Target for Folate-linked Therapeutic Agents," Archives of Pathology and Laboratory Medicine 137(2):241-244, College of American Pathologists, United States (Feb. 2013).

Carboplatin, "An organoplatinum compound that possesses antineoplastic activity," NIH TOXNET, accessed at https://chem.nim.nih.gov/chemidplus/name/carboplatin accessed on Jan. 12, 2018. 5 Pages.

Carrigan, C.N., et al., "Evaluation of Folate Receptor 1 (FOLR1) Expression by Calibrated Immunohistochemistry Identifies Candidate Tumor subtypes for Targeting by IMGN853, An Anti-FOLR1-maytansinoid Conjugate," 102nd Annual AACR Meeting—Orlando, FL (Apr. 2-6, 2011), Abstract 3617, 1 Page, American Association for Cancer Research, United States (distributed in print Mar. 8, 2011; available online Feb. 25, 2011).

Carrigan, C.N., et al., "Evaluation of Folate Receptor 1 (FOLR1) Expression by Calibrated Immunohistochemistry Identifies Candidate Tumor Subtypes for Targeting by IMGN853, an Anti-FOLR1-Maytansinoid Conjugate," 102nd Annual AACR Meeting—Orlando, FL (Apr. 2-6, 2011), Abstract 3617 Poster, American Association for Cancer Research, United States (Apr. 2, 2011).

Chen, J., et al., "Antibody-cytotoxic Agent Conjugates for Cancer Therapy," Expert Opinion on Drug Delivery 2(5):873-890, Informa Healthcare, England (2005).

Chen, Y., et al., "Drug Delivery Across the Blood-brain Barrier," Current Drug Delivery 1(4):361-376, Bentham Science Publishers, United Arab Emirates (2004).

Cisplatin, "An inorganic and water soluble platinum complex," NIH TOXNET, accessed at https://chem.nlm.nih.gov/chemidplus/rn/15663-27-1 accessed on Jan. 12, 2018. 7 Pages.

Cohen, M.H.; et al., "FDA Drug approval summary: Bevacizumab plus Carboplatin and Paclitaxel as First-Line Treatment of Advanced/Metastatic Recurrent Nonsquamous Non-small Cell Lung Cancer," *The Oncologist* 12:713-718,Society for Translational Oncology, United States (2007).

Colman, P.M., "Effects of Amino Acid Sequence Changes on Antibody-antigen Interactions," Research in Immunology 145(1):33-36, Elsevier, France (1994).

Colnaghi, M.I., "Generation of Monoclonal Antibodies for In Vivo Approaches," International Journal of Radiation Applications and Instrumentation. Part B, Nuclear Medicine and Biology 18(1):15-18, Pergamon Press, England (1991).

Conde, F.P., et al., "The Aspergillus Toxin Restriction is a Suitable Cytotoxic Agent for Generation of Immunoconjugates with Monoclonal Antibodies Directed Against Human Carcinoma Cells," European Journal of Biochemistry / FEBS 178(3):795-802, Federation of European Biochemical Societies, England (1989).

Coney, L.R., et al., "Chimeric Murine-human Antibodies Directed Against Folate Binding Receptor are Efficient Mediators of Ovarian Carcinoma Cell Killing," Cancer Research 54(9):2448-2455, American Association for Cancer Research, United States (1994).

Coney, L.R., et al., "Cloning of a Tumor-associated Antigen: MOv18 and MOv19 Antibodies Recognize a Folate-binding Protein," Cancer Research 51(22):6125-6132, American Association for Cancer Research, United States (1991).

Copeland, A., et al., "B1G510 (B1G510_9BURK) Unreviewed, UniProtKB/TrEMBL," UniProt, 3 pages, last modified Dec. 14, 2011, accessed at http://www.uniprot.org/uniprot/B1G510>.

Dhar, S.; et al., "Targeted delivery of a cisplatin prodrug for safer and more effective prostate cancer therapy in vivo," *PNAS* 108(5):1850-1855, Unites States National Academy of Sciences, Unites States (2011).

Dirks, N.L., et al., "Population Pharmacokinetics of Cetuximab in Patients With Squamous Cell Carcinoma of the Head and Neck," Journal of Clinical Pharmacology 48(3):267-278, The American College of Clinical Pharmacology, United States (2008).

(56) References Cited

OTHER PUBLICATIONS

Ebel, W., et al., "Preclinical Evaluation of MORAb-003, a Humanized Monoclonal Antibody Antagonizing Folate Receptor-Alpha," Cancer Immunity 7:6, Cancer Research Institute, United States (2007).
English language Abstract of Chinese Patent Publication No. 101139613A, European Patent Office, espacenet database—Worldwide, (2012).
English language Abstract of Chinese Patent Publication No. 101440130A, European Patent Office, espacenet database—Worldwide, (2012).
F9RS38, UniProtKB/TrEMBL Accession No. F9RS38_9VIBR, Nov. 28, 2012 [online]; [Retrieved on Feb. 3, 2015; http://www.uniprot.org/uniprot/F9RS38.txt?version=5>.
Farrell, C., et al., "Population Pharmacokinetics of Farletuzumab, a Humanized Monoclonal Antibody Against Folate Receptor Alpha, in Epithelial Ovarian Cancer," Cancer Chemotherapy and Pharmacology 70(5):727-734, Springer Verlag, Germany (2012).
Ferrara, N., et al., "The biology of VEGF and its receptors," *Nature Medicine* 9(6)669-676), Nature Publishing Group, England (2003).
Ferrini, S., et al., "Bispecific Monoclonal Antibodies Directed to CD16 and to a Tumor-associated Antigen Induce Target-cell Lysis by Resting NK Cells and by a Subset of NK Clones,"International Journal of Cancer 48(2):227-233, Wiley-Liss, United States (1991).
Ferrini, S., et al., "Retargeting of T-cell-receptor Gamma/delta+ Lymphocytes Against Tumor Cells by Bispecific Monoclonal Antibodies. Induction of Cytolytic Activity and Lymphokine Production," International Journal of Cancer 4:53-55, Wiley-Liss, United States (1989).
Figini, M., et al., "Conversion of Murine Antibodies to Human Antibodies and their Optimization for Ovarian Cancer Therapy Targeted to the Folate Receptor," Cancer Immunology, Immunotherapy 58(4):531-546, Springer Verlag, Germany (2009).
Figini, M., et al., "Panning Phage Antibody Libraries on Cells: Isolation of Human Fab Fragments Against Ovarian Carcinoma Using Guided Selection," Cancer Research 58(5):991-996, American Association for Cancer Research, United States (1998).
Franklin, W.A., et al., "New Anti-lung-cancer Antibody Cluster 12 Reacts with Human Folate Receptors Present on Adenocarcinoma," International Journal of Cancer. Supplement 8:89-95, Wiley-Liss, United States (1994).
Gehl, J.; et al. "combined doxorubicin and paclitaxel in advanced breast cancer: Effective and cardiotoxic," *Annals of Oncology* 7:687-693, Kluwer Academic Publishers, Netherlands (1996).
Gould, H.J., et al., "Comparison of IgE and IgG Antibody-dependent Cytotoxicity in Vitro and in a SCID Mouse Xenograft Model of Ovarian Carcinoma," European Journal of Immunology 29(11):3527-3537, Wiley-VCH, Germany (1999).
Green, B. and Duffull, S.B., "What is the Best Size Descriptor to Use for Pharmacokinetic Studies in the Obese?," British Journal of Clinical Pharmacology 58(2):119-133, Blackwell Publishing Ltd., England (2004).
H0DED6, UniProtKB/TrEMBL Accession No. H0DED6_9STAP, Nov. 28, 2012 [online]. [Retrieved on Feb. 3, 2015]; http://www.uniprot.org/uniprot/H0DED6.txt?version=5>.
Hartmann, L.C., et al., "Folate Receptor Overexpression is Associated with Poor Outcome in Breast Cancer," International Journal of Cancer 121(5):938-942, Wiley-Liss, United States (2007).
Hoeben, A., et al., "Vascular Endothelial Growth Factor and Angiogenesis," *Pharmacological Reviews* 56(4):549-580, The American Society for Pharmacology and Experimental Therapeutics, Unites States (2004).
Hofland, P., "Refined Dosing Strategy for IMGN853 Achieves Objective," ADC Review, Apr. 8, 2014, Retrieved from the internet at URL: https://adcreview.com/editorial/refined-dosing-strategy-imgn853-achieves-objective/.
Holash, J.; et al., "VEGF-Trap: A VEGF blocker with potent antitumor effects," *PNAS* 99(17):11393-11398, National Academy of Sciences, Unites States (2002).

Huang, J.; et al., "HMG-domain proteins specifically inhibit the repair of the major DNA adduct of the anticancer drug cisplatin by human excision nuclease," *Proc. Natl. Acad. Sci.*91:10394-10398, National Academy of Sciences, United States (1994).
Jones, M.B., et al., "Rationale for Folate Receptor Alpha Targeted Therapy in "High Risk" Endometrial Carcinomas," International Journal of Cancer 123(7):1699-1703, Wiley-Liss, United States (2008).
Kalli, K.R., et al., "Folate Receptor Alpha as a Tumor Target in Epithelial Ovarian Cancer," Gynecologic Oncology 108(3):619-626, Academic Press, United States (2008).
Karagiannis, S.N., et al., "IgE-antibody-dependent Immunotherapy of Solid Tumors: Cytotoxic and Phagocytic Mechanisms of Eradication of Ovarian Cancer Cells," Journal of immunology 179(5):2832-2843, American Association of Immunologists, United States (2007).
Keleman, L.E., "The role of folate receptor $\alpha$ in cancer development, progression and treatement: Cause, consequences or innocent bystander?" *Int. J. Cancer* 119:243-250, Wiley-Liss, United States (2006).
Konner, J.A., et al., "Farletuzumab, a Humanized Monoclonal Antibody against Folate Receptor Alpha, in Epithelial Ovarian Cancer: A Phase I Study," Clinical Cancer Research 16(21):5288-5295, The Association, United States (2010).
Ladd, S., et al., "Folate Receptor 1 Immunohistochemistry Repeatability and Stored Slide Antigen Stability," 38th Annual NSH Symposium—Vancouver, BC Canada (Sep. 28-Oct. 3, 2012), Abstract, 1 page, National Society for Histotechnology, Canada (2012).
Ladd, S., et al., "Folate Receptor 1 Immunohistochemistry Repeatability and Stored Slide Antigen Stability," 38th Annual NSH Symposium—Vancouver, BC Canada (Sep. 28-Oct. 3, 2012), Poster P-38, National Society for Histotechnology, Canada (Sep. 28, 2012).
Lawson, N. and Scorer, P., "Evaluation of Antibody to Folate Receptor-alpha (FR-alpha)," published online on May 31, 2010, accessed at http://www.leicabiosystems.com/pathologyleaders/evaluation-of-antibody-to-folate-receptor-alpha-fr-%CE%B1/, accessed on Oct. 27, 2014 (1 page).
Leung, F., et al., "Folate-receptor 1 (FOLR1) protein is elevated in the serum of ovarian cancer patients," *Clin. Biochem.*46(15):1462-1468, Elsevier, Netherlands (2013).
Lim, J., et al., "C5A929 (C5A929_BURGB) Unreviewed, UniProtKB/TrEMBL", UniProt, 4 pages, last modified Apr. 18, 2012, accessed at http://www.uniprot.org/uniprot/C5A929>.
Lokich, J.; et al., "Carboplatin versus cisplatin in solid tumors: An analysis of the literature," *Annals of Oncology* 9:13-21, Kluwer Academic Publishers, Netherlands (1998).
Lu, Y. and Low, P.S., "Immunotherapy of Folate Receptor-expressing Tumors: Review of Recent Advances and Future Prospects," Journal of Controlled Release 91(1-2):17-29, Elsevier Science Publishers, Netherlands (2003).
Mantovani, L.T., et al., "Folate Binding Protein Distribution in Normal Tissues and Biological Fluids from Ovarian Carcinoma Patients as Detected by the Monoclonal Antibodies MOv18 and MOv19," European Journal of Cancer 30A(3):363-369, Pergamon Press, England (1994).
Melani, C., et al., "Targeting of Interleukin 2 to Human Ovarian Carcinoma by Fusion with a Single-chain Fv of Antifolate Receptor Antibody," Cancer Research 58(18):4146-4154, American Association for Cancer Research, United States (1998).
Mezzanzanica, D., et al., "Human Ovarian Carcinoma Lysis by Cytotoxic T Ccells Targeted by Bispecific Monoclonal Antibodies: Analysis of the Antibody Components," International Journal of Cancer 41(4):609-615, Wiley-Liss, United States (1988).
"Mirvetuximab Soravtansine," Press Release on Apr. 24, 2015, Immunogen Inc. Accessed at http://www.immunogen.com/pipeline/mirvetuximab-soravtansine accessed on Jan. 12, 2018, 1 Page.
Miotti, S., et al., "Characterization of Human Ovarian Carcinoma-associated Antigens Defined by Novel Monoclonal Antibodies with Tumor-restricted Specificity," International Journal of Cancer 39(3):297-303, Wiley-Liss, United States (1987).
NCL-L-FRalpha, "Novocastra Liquid Mouse Monoclonal Antibody Folate Receptor Alpha: Product Code: NCL-L-FRalpha," 40 Pages, Leica Biosystems Newcastle Ltd, England (2009).

(56) References Cited

OTHER PUBLICATIONS

Nikolinakos, P., et al., "The Tyrosine Kinase Inhibitor Cediranib for Non-small cell lung cancer and other thoracic malignancies," *J Thorac Oncol.*3(6)S131-S134, Elsevier, Netherlands (2008).
Nishiyama, T., et al., "A9SZW6 (A9SZW6_PHYPA) Unreviewed, UniProtKB/TrEMBL," UniProt, 3 pages, last modified Sep. 21, 2011, accessed at http://www.uniprot.org/uniprot/A9SZW6>.
Nutt, J.E., et al., "The Role of Folate Receptor Alpha (FRalpha) in the Response of Malignant Pleural Mesothelioma to Pemetrexed-containing Chemotherapy," British Journal of Cancer 102(3):553-560, Nature Publishing Group, England (2010).
Obasaju, C.K., et al., "Evaluation of Carboplatin Pharmacokinetics in the Absence and Presence of Paclitaxel," *Clin. Cancer Res.*2:549-552, American Association for Cancer Research, United States (1996).
O'Shannessy, D.J., et al., "Characterization of the Human Folate Receptor Alpha via Novel Antibody-based Probes," Oncotarget 2(12):1227-1243, Impact Journals, United States (2011).
Paganelli, G., et al., "Two-step Tumour Targetting in Ovarian Cancer Patients Using Biotinylated Monoclonal Antibodies and Radioactive Streptavidin," European Journal of Nuclear Medicine 19(5):322-329, Springer Verlag, Germany (1992).
Pasqua, A.J., et. al., "Understanding how the platinum anticancer drug carboplatin works: from the bottle to the cell," *Inorganica Chemica Acta* 389:29-35, Elsevier, Netherlands (2012).
Paul, W.E., "Structure and Function of Immunoglobulins," in *Fundamental Immunology*, Third Edition, pp. 292-295, Raven Press, New York, United States (1993).
Portolano, S., et al., "Lack of Promiscuity in Autoantigen-Specific H and L Chain Combinations as Revealed by Human H and L Chain 'Roulette'," The Journal of Immunology 150(3):880-887, The American Association of Immunologists, United States (1993).
Presta, L.G., et al., "Humanization of an Anti-vascular Endothelial Growth Factor Monoclonal Antibody for the therapy of solid tumors and other disorders," *Cancer Research* 57:4593-4599, American Association for Cancer Research, United States (1997).
R5I4W9, UniProtKB/TrEMBL Accession No. R5I4W9_9FIRM, Jul. 24, 2013 [online]. [Retrieved on Feb. 3, 2015]: http://www.uniprot.org/uniprot/R5I4W9.txt?version=1>.
Roberts. S.J., et al., "Role of Individual N-linked Glycosylation Sites in the Function and Intracellular Transport of the Human Alpha Folate Receptor," Archives of Biochemistry and Biophysics 351(2):227-235, Academic Press, United States (1998).
Rudikoff, S., et al., "Single Amino Acid Substitution Altering Antigen-Binding Specificity," Proceedings of the National Academy of Sciences 79(6):1979-1983, The National Academy of Sciences, United States (1982).
Sandler, A., et al., "Paclitaxel-carboplatin alone or with Bevacizumab for Non-Small-Cell Lung Cancer," *N Engl J Med* 355:2542-2550, Massachusetts Medical Society, United States (2006).
Scorer, P., et al., "A Full Immunohistochemical Evaluation of a Novel Monoclonal Antibody to Folate Receptor—alpha (FR-alpha)," reAGENTS 3:8-12, Leica Biosystems Newcastle Ltd., England (2010).
Search Report and Written Opinion for Singaporean Patent Application No. 2013070040, Intellectual Property Office of Singapore, Singapore, dated Dec. 30, 2014, 17 pages.
Singh, R. and Erickson, H.K., "Antibody-cytotoxic Agent Conjugates: Preparation and Characterization," Methods in Molecular Biology 525:445-467, Humana Press, United States (2009).
Smith, A.E., et al., "A Novel Monoclonal Antibody for Detection of Folate Receptor Alpha in Paraffin-embedded Tissues," Hybridoma 26(5):281-288, Mary Ann Liebert, Inc., United States (2007).
Smith-Jones, P.M., et al., "Preclinical Radioimmunotargeting of Folate Receptor Alpha Using the Monoclonal Antibody Conjugate DOTA-MORAb-003," Nuclear Medicine and Biology 35(3):343-351, Elsevier, United States (2008).
Stewart, M.W., "Aflibercept (VEGF Trap-eye): the newest anti-VEGF drug," *J Ophthalmol* 96(9)1157-1158, Elsevier, Netherlands (2012).

Supplementary European Search Report and European Search Opinion for EP Application No. EP11748067, The Hague, Netherlands, dated Jun. 26, 2013.
Supplementary Partial European Search Report for EP Application No. EP12764885, The Hague, Netherlands, dated Nov. 21, 2014.
Tacar, O., et al., "Doxorubicin: an update on anticancer molecular action, toxicity and novel drug delivery systems," *Journal of Pharmacy and Pharmacology*65:157-170, Wiley-Blackwell, United States (2013).
Testa, N., et al., "A Method for Quantifying Soluble Folate Receptor 1 in IMGN853 0401 Clinical Trial Patients," 2013 AACR Annual Meeting—Washington, DC (Apr. 6-10, 2013), Abstract #3503 Poster, American Association of Cancer Research, United States (Apr. 6, 2013).
Testa, N., et al., "A Method for Quantifying Soluble Folate Receptor 1 in IMGN8530401 Clinical Trial Patients," 2013 AACR Annual Meeting—Washington, DC (Apr. 6-10, 2013), Abstract #3503, 1 Page, American Association of Cancer Research, United States (submitted Nov. 15, 2012).
Tolcher, A., et al., "A Novel Dosing Strategy on Plasma Levels of CanAg in a Phase II Study of IMGN242 (huC242-DM4) in Gastric Cancer," 20th EORTC-NCI-AACR Symposium: Abstract #514, Oct. 21-24, 2008, Geneva, Switzerland (2008).
"Types of Solid Tumors," St. Jude Children's Research Hospital, accessed at https://www.stjude.org/disease/solid-tumors.html accessed on Jan. 12, 2018, 2 pages.
Vajdos, F.F., et al., "Comprehensive Functional Maps of the Antigen-Binding Site of an Anti-ErbB2 Antibody obtained with Shotgun Scanning Mutagenesis," *Journal of Molecular Biology* 320(2):415-428, Elsevier Science, United States (2002).
Van Dam, G.M., et al., "Intraoperative Tumor-specific Fluorescence Imaging in Ovarian Cancer by Folate Receptor-alpha Targeting: First in-human Results," *Nature Medicine* 17(10):1315-1319, Nature Publishing Company, United States (2011).
White, A.J., et al., "Efficacy and safety of farletuzumab, a humanized monoclonal antibody to folate receptor alpha, in platinum-sensitive relapsed ovarian cancer subjects: Final data from a multicenter phase II study," *Journal of Clinical Oncology* 28(15), Supp. SUPPL. 1. Abstract Number: 5001(1 page), American Society of Clinical Oncology, United States (2010).
Whiteman, K.R., et al., "Anti-tumor Activity and Pharmacokinetics of the Anti-FOLR-1-maytansinoid Conjugate IMGN853 is Maintained Over a Wide Range of Maytansinoid-to-antibody Ratios," 103rd Annual AACR Meeting—Chicago, IL (Mar. 31-Apr. 4, 2012), Abstract #4628, 1 page, American Association for Cancer Research, United States (2012).
Whiteman, K.R., et al., "Anti-tumor Activity and Pharmacokinetics of the Anti-FOLR-1-maytansinoid Conjugate IMGN853 is Maintained Over a Wide Range of Maytansinoid-to-antibody Ratios," 103rd Annual AACR Meeting—Chicago, IL (Mar. 31-Apr. 4, 2012), Abstract #4628 Poster, American Association for Cancer Research, United States (Mar. 31, 2012).
Whiteman, K.R., et al., "Preclinical Evaluation of IMGN853, An Anti-FOLR1 Antibody-maytansinoid Conjugate, as a Potential Therapeutic for Ovarian Cancer," 102nd Annual AACR Meeting—Orlando, FL (Apr. 2-6, 2011), Abstract 1760, 1 Page, American Association for Cancer Research, United States (distributed in print Mar. 8, 2011; available online Feb. 25, 2011).
Whiteman, K.R., et al., "Preclinical Evaluation of IMGN853, An Anti-FOLR1 Antibody-maytansinoid Conjugate, as a Potential Therapeutic for Ovarian Cancer," 102nd Annual AACR Meeting—Orlando, FL (Apr. 2-6, 2011), Abstract 1760 Poster, American Association for Cancer Research, United States (Apr. 2, 2011).
Widdison, W.C., et al., "Semisynthetic Maytansine Analogues for the Targeted Treatment of Cancer," Journal of Medicinal Chemistry 49(14):4392-4408, American Chemical Society, United States (2006).
Wu, J., et al., "Assessing Cytotoxic Treatment Effects in Preclinical Tumor Xenograph Models," *J Biopharm Stat.* 19(5):755-762, Taylor & Francis, England (2009).
Yan, Kunimasa, et al., "N-Linked Glycosylation Is Critical for the Plasma Membrane Localization of Nephrin," Journal of the American Society of Nephrology 13: 1385-1389, American Society of Nephrology, United States (2002).

(56) References Cited

OTHER PUBLICATIONS

Yuan, Y., et al., "Expression of the Folate Receptor Genes FOLR1 and FOLR3 Differentiates Ovarian Carcinoma from Breast Carcinoma and Malignant Mesothelioma in Serous Effusions," Human Pathology 40(10):1453-1460, W B Saunders, United States (2009).
Zacchetti, A., et al., "(177)Lu- Labeled MOv18 as Compared to (131)I- or (90)Y-labeled MOv18 has the Better Therapeutic Effect in Eradication of Alpha Folate Receptor-expressing Tumor Xenografts," Nuclear Medicine and Biology 36(7):759-770, Elsevier, United States (2009).
Zwicke, G.L., et al., "Utilizing the folate receptor for actice targeting of cancer nanotherapeutics," *Nano Reviews* 3:18496-18507, Co-action publishing, Sweden (2012).
NCT01609556, "A Phase 1, First-in-Human Study to Evaluate the Safety, Tolerability, Pharmacokinetics and Pharmacodynamics of IMGN853 in Adults with Ovarian Cancer and Other FOLR1-Positive Solid Tumors" (2012), ClinicalTrials.gov archive, accessed at https://clinicaltrials.gov/archive/NCT01609556/2012_05_31, on Feb. 12, 2016, 6 pages.
NCT01609556, "First-in-Human Study to Evaluate the Safety, Tolerability, Pharmacokinetics and Pharmacodynamics of IMGN853 in Adults with Ovarian Cancer and Other FOLR1-Positive Solid Tumors (IMGN-0401)" (2012), accessed at https://clinicaltrials.gov/ct2/show/NCT01609556?term=IMGN853&rank=3, on Feb. 12, 2016, 4 pages.
NCT02631876, "PH2 Study of IMGC853 vs Investigator's Choice of Chemo in Adults with Fra+ Adv. EOC, Primary Peritoneal or Primary Fallopian Tube Cancer" (Dec. 10, 2015), accessed at https://clinicaltrials.gov/ct2/show/study/NCT02631876?term=mirvetuximab+soravtansine, on Feb. 12, 2016, 3 pages.
Kurkjian, C., et al., "A phase I, first-in-human study to evaluate the safety, pharmacokinetics (PK), and pharmacodynamics (PD) of IMGN853 in patients (Pts) with epithelial ovarian cancer (EOC) and other FOLR1-positive solid tumors," 2013 ASCO Annual Meeting, Poster, 4 pages (Jun. 2013).
Kurkjian, C., et al., "A phase I, first-in-human study to evaluate the safety, pharmacokinetics (PK), and pharmacodynamics (PD) of IMGN853 in patients (Pts) with epithelial ovarian cancer (EOC) and other FOLR1-positive solid tumors," Journal of Clinical Oncology 31:SUPPL. Abstract 2573, 2 pages, American Society of Clinical Oncology, United States (2013).
Moore, K.N., et al., "Relationship of pharmacokinetics (PK), toxicity, and initial evidence of clinical activity with IMGN853, a folate receptor alpha (Fra) targeting antibody drug conjugate in patients (Pts) with epithelial ovarian cancer (EOC) and other Fra-positive solid tumors," 2014 ASCO Annual Meeting, Abstract 5571, 3 pages (2014).
Moore, K.N., et al., "Relationship of pharmacokinetics (PK), toxicity, and initial evidence of clinical activity with IMGN853, a folate receptor alpha (Fra) targeting antibody drug conjugate in patients (Pts) with epithelial ovarian cancer (EOC) and other Fra-positive solid tumors," 2014 ASCO Annual Meeting, Poster, 5 pages (2014).
Ponte, J.F., et al., "Development of Modified Dosing Approaches to Achieve Specific Pharmacokinetic (PK) Objectives in the First-in-Human Phase I Clinical Trial of IMGN853, a Folate Receptor alpha-Targeting Antibody Drug Conjugate," 2014 AACD Annual Meeting, Poster, 5 pages (2014).
Ponte, J.F., et al., "Incorporation of Modified Dosing Approaches Based on Pharmacokinetic Analysis in a First in Human Phase I Clinical Trial of IMGN853, a Folate Receptor α-Targeting Antibody Drug Conjugate," 2014 AACR Annual Meeting, 2 pages (2014).
Gershoni, J.M., et al., "Epitop Mapping the First Step in Developing Epitope-Based Vaccines," *Biodrugs* 21(3):145-156, Adis Data Information BV, Israel (2007).
Winkler, K., et al., "Changing the Antigen Binding Specificity by Single Point Mutations of an Anti-p24 (HIV-1) Antibody," *Journal of Immunology* 165:4505-4514, American Association of Immunologists, United States (2000).
"Representative Clinical Trials of Immunoconjugates as Anti-Solid Tumor Agents," Timeline created Mar. 16, 2000.

Casalini, P., et al. "Use of combination of monoclonal antibodies directed against three distinct epitopes of a tumor-associated antigen: Analysis of cell binding and internalization." *International Journal of Cancer*, 48:2, Germany (1991).
Weitman, S.D., et al., "Distribution of the Folate Receptor GP38 in Normal and Malignant Cell Lines and Tissues," *Canc. Res.* 52:3396-3401, American Association for Cancer Research, USA (1992).
P15328, UniProtKB/TrEMBL Accession No. P15328, Jan. 16, 2018 [online]. [Retrieved on Jan. 16, 2018]: http://www.uniprot.org/uniprot/P15328.
P15692, UniProtKB/TrEMBL Accession No. P15692, Jan. 16, 2018 [online]. [Retrieved on Jan. 16, 2018]: http://www.uniprot.org/uniprot/P15692.
Meadows, K.L. and Hurwitz, H.I., et al., "Anti-VEGF Therapies in the Clinic," *Cold Spring Harbor Perspectives in Medicine* 2:a006577, Cold Spring Harbor Laboratory Press, USA (2012).
International Search Report & Written Opinion for International Application No. PCT/US2016/052231, ISA/US, Alexandria, Virginia, United States, dated Dec. 20, 2016, 14 pages.
Garcia, A. et al., "Bevacizumab and Ovarian Cancer" *Therapeutic Advances in Medical Oncology*, 5:2; 133-141 United States (Mar. 2013).
Takahashi, S., "Vascular Endothelial Growth Factor (VEGF), VEGF Receptors and Their Inhibitors for Antiangiogneic Tumor Therapy," *Biological and Pharmaceutical Bulletin*; 34:12; 1785-1788; United States (2011).
Lam, S.W. et al. "Paclitaxel and Bevaclzumab With or Without Capecltablne as First-Line 101 Treatment for HER2-NegatIve Locally Recurrent or Metastatic Breast Cancer: A MuitIcentre, Open-Label, Randomised Phase 2 Trial," *European Journal of Cancer*, 50: 18; 3077-3088, England (Dec. 2014).
Chintagumpala, M. et al. "Phase I and PharmacokInetic Study of Thalidomide With Carboplatin in Children With Cancer," *Journal of Clinical Oncology*, 22: 21; 4394-4400, United States (2004).
Rose, P.G. "Pegylated Liposomal Doxorubicin: Optimizing the Dosing Schedule in Ovarian Cancer," *Oncologist*, 10:3; 205-214; United States (2005).
Ekhart, C., et al., "Carboplatin dosing in overweight and obese patients with normal renal function, does weight matter?," *Cancer Chemother Pharmcol.* 64:115-122, Springer Science+Business Media, Germany (2008).
Runnebaum I.B., and Bruning, A., "Glucocorticoids Inhibit Cell Death in Ovarian Cancer and Up-regulate Caspase Inhibitor cIAP2," *Clinical Cancer Research* 17:6325-6333, American Association for Cancer Research, United States (2005).
Arjaans, M., et al., "Bevacizumab-induced normalization of blood vessels in tumors hampers antibody uptake," *Cancer Research*, 73:3347-3355, United States (2013).
Heskamp, S., et al., "Bevacizumab reduces tumor targeting of antiepidermal growth factor and anti-insulin-like growth factor 1 receptor antibodies," *International Journal of Cancer*, 133: 307-315, Germany (2013).
Arjaans, M., et al., "Bevacizumab-Induced Vessel Nomalization Hampers Tumor Uptake of Antibodies—Response," *Cancer Research*, 73: 7147-7148, United States (2013).
Hecht, J.R., et al., "A randomized phase IIIB trial of chemotherapy, bevacizumab, and panitumumab compared with chemotherapy and bevacizumab for metastatic colorectal cancer," *Journal of Clinical Oncology*, 27: 672-680, United States (2009).
O'Malley, D.M., et al., "Safety findings from Forward II: a Phase 1b study evaluating the folate receptor alpha (FRα)-targeting antibody-drug conjugate (ADC) mirvetuximab soravtansine (IMGN853) in combination with bevacizumab, carboplatin, pegylated liposomal doxorubicin (PLD), or pembrolizumab in patients with ovarian cancer " ASCO Annual Meeting Jun. 2-6, 2017, 1 page, United States (Jun. 2-6, 2017).
"Bevacizumab", A description of the drug and its effects, EMEA (2005).
Cis-Diammineplatinum(II) dichloride, "Cisplatin is a platinum containing, broad activity antineoplastic and alkylating agent effective against various types of solid tumors," Sigma Aldrich, 2 pages (2007).

(56) References Cited

OTHER PUBLICATIONS

Cisplatin Injection Disclaimer and Description, WG Critical Care, LLC. 11 pages (Feb. 2015).
Platinol Injection label, Bristol-Myers Squibb Company, 15 pages (2009).
U.S. Appl. No. 16/002,364, Ab, O., et al., filed Jun. 7, 2018 (Not Published).
Non-Final Office Action dated Aug. 27, 2015, in U.S. Appl. No. 14/509,809, Lutz, R.J., et al., filed Oct. 8, 2014.
Final Office Action dated Dec. 9, 2015, in U.S. Appl. No. 14/509,809, Lutz, R.J., et al., filed Oct. 8, 2014.
Non-Final Office Action dated Mar. 18, 2016, in U.S. Appl. No. 14/509,809, Lutz, R.J., et al., filed Oct. 8, 2014.
Non-Final Office Action dated Aug. 3, 2016, in U.S. Appl. No. 14/509,809, Lutz, R.J., et al., filed Oct. 8, 2014.
Final Office Action dated May 8, 2017, in U.S. Appl. No. 14/509,809, Lutz, R.J., et al., filed Oct. 8, 2014.
O'Malley, D.M., et al., "Mirvetuximab soravtansine, a folate receptor alpha (FRα)-targeting antibody-drug conjugate (ADC), in combination with bevacizumab in patients (pts) with platinum-resistant ovarian cancer: maturing safety and activity profile from the Forward II Phase 1b study," ASCO Annual Meeting Jun. 1-5, 2018, 11 pages, United States (Jun. 1-5, 2018).

\* cited by examiner

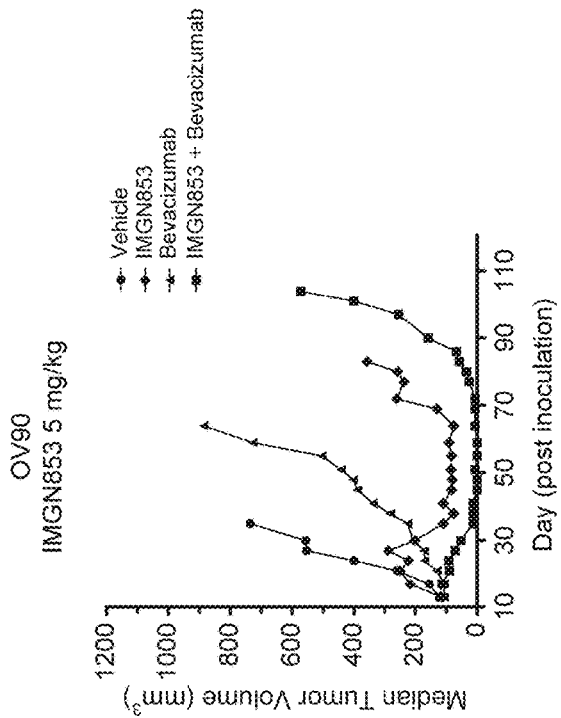
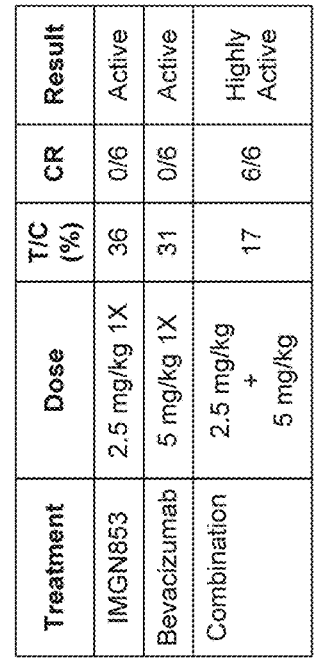
FIG. 2A
FIG. 2B

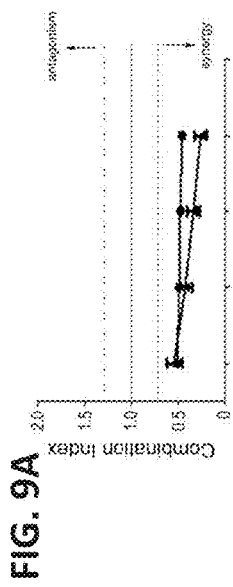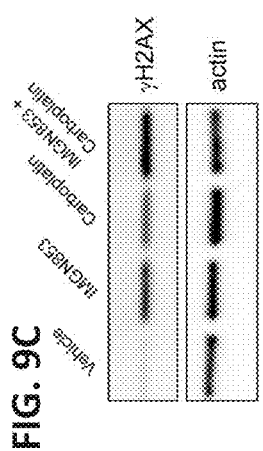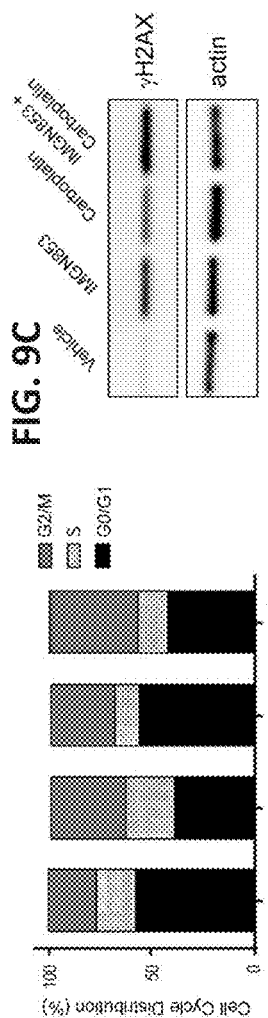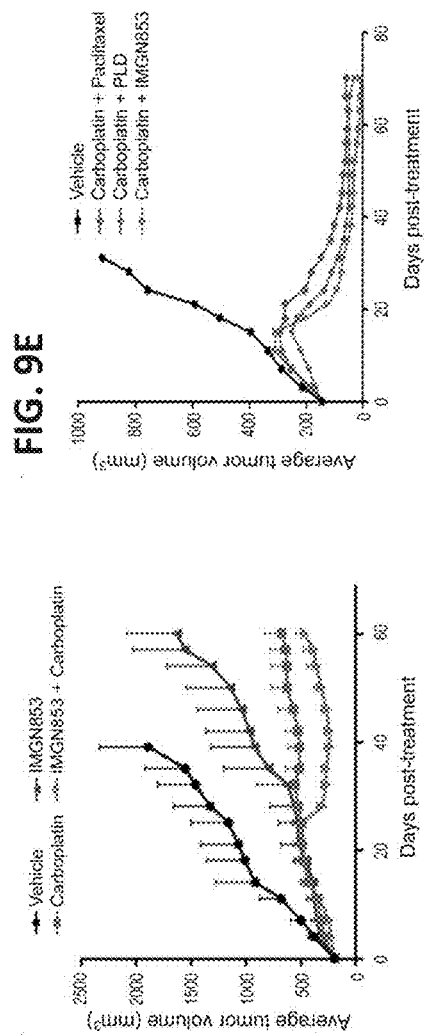
FIG. 9A
FIG. 9C
FIG. 9E
FIG. 9B
FIG. 9D

SEQUENCE LISTING

<160> NUMBER OF SEQ ID NOS: 19

<210> SEQ ID NO 1
<211> LENGTH: 257
<212> TYPE: PRT
<213> ORGANISM: Homo sapiens

<400> SEQUENCE: 1

Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

```
Leu Tyr Arg Phe Asn Trp Asn His Cys Gly Glu Met Ala Pro Ala Cys
                 85                  90                  95
Lys Arg His Phe Ile Gln Asp Thr Cys Leu Tyr Glu Cys Ser Pro Asn
            100                 105                 110
Leu Gly Pro Trp Ile Gln Gln Val Asp Gln Ser Trp Arg Lys Glu Arg
        115                 120                 125
Val Leu Asn Val Pro Leu Cys Lys Glu Asp Cys Glu Gln Trp Trp Glu
    130                 135                 140
Asp Cys Arg Thr Ser Tyr Thr Cys Lys Ser Asn Trp His Lys Gly Trp
145                 150                 155                 160
Asn Trp Thr Ser Gly Phe Asn Lys Cys Ala Val Gly Ala Ala Cys Gln
                165                 170                 175
Pro Phe His Phe Tyr Phe Pro Thr Pro Thr Val Leu Cys Asn Glu Ile
            180                 185                 190
Trp Thr His Ser Tyr Lys Val Ser Asn Tyr Ser Arg Gly Ser Gly Arg
        195                 200                 205
Cys Ile Gln Met Trp Phe Asp Pro Ala Gln Gly Asn Pro Asn Glu Glu
    210                 215                 220
Val Ala Arg Phe Tyr Ala Ala Ala Met Ser Gly Ala Gly Pro Trp Ala
225                 230                 235                 240
Ala Trp Pro Phe Leu Leu Ser Leu Ala Leu Met Leu Leu Trp Leu Leu
                245                 250                 255
Ser

<210> SEQ ID NO 2
<211> LENGTH: 771
<212> TYPE: DNA
<213> ORGANISM: Homo sapiens

<400> SEQUENCE: 2
atggctcagc ggatgacaac acagctgctg ctccttctag tgtgggtggc tgtagtaggg       60
gaggctcaga caaggattgc atgggccagg actgagcttc tcaatgtctg catgaacgcc      120
aagcaccaca ggaaaagcc aggccccgag acaagttgc atgagcagtg tcgaccctgg        180
aggaagaatg cctgctgttc taccaacacc agccaggaag cccataagga tgtttcctac      240
ctatatagat tcaactggaa ccactgtgga gagatggcac ctgcctgcaa acggcatttc      300
atccaggaca cctgcctcta cgagtgctcc cccaacttgg ggccctggat ccagcaggtg      360
gatcagagct ggcgcaaaga gcgggtactg aacgtgcccc tgtgcaaaga ggactgtgag      420
caatggtggg aagattgtcg cacctcctac acctgcaaga gcaactggca caagggctgg      480
aactggactt cagggtttaa caagtgcgca gtgggagctg cctgccaacc tttccatttc      540
tacttcccca cacccactgt tctgtgcaat gaaatctgga ctcactccta caaggtcagc      600
aactacagcc gagggagtgg ccgctgcatc cagatgtggt tcgacccagc ccagggcaac      660
cccaatgagg aggtggcgag gttctatgct gcagccatga gtggggctgg gccctgggca      720
gcctggcctt tcctgcttag cctggcccta atgctgctgt ggctgctcag c               771

<210> SEQ ID NO 3
<211> LENGTH: 118
<212> TYPE: PRT
<213> ORGANISM: Artificial Sequence
<220> FEATURE:
<223> OTHER INFORMATION: FOLR1 Antibody huMov19 - VH

<400> SEQUENCE: 3
```

```
Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
            115

<210> SEQ ID NO 4
<211> LENGTH: 112
<212> TYPE: PRT
<213> ORGANISM: Artificial Sequence
<220> FEATURE:
<223> OTHER INFORMATION: FOLR1 Antibody huMov19 - VL version 1.00

<400> SEQUENCE: 4

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
            35                  40                  45

Arg Leu Leu Ile Tyr Arg Ala Ser Asn Leu Glu Ala Gly Val Pro Asp
        50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 5
<211> LENGTH: 112
<212> TYPE: PRT
<213> ORGANISM: Artificial Sequence
<220> FEATURE:
<223> OTHER INFORMATION: FOLR1 Antibody huMov19 - VL version 1.60

<400> SEQUENCE: 5

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr Gln Gln Lys Pro Gly Gln Gln Pro
            35                  40                  45

Arg Leu Leu Ile Tyr Arg Ala Ser Asn Leu Glu Ala Gly Val Pro Asp
        50                  55                  60

Arg Phe Ser Gly Ser Gly Ser Lys Thr Asp Phe Thr Leu Thr Ile Ser
```

```
                65                  70                  75                  80
Pro Val Glu Ala Glu Asp Ala Ala Thr Tyr Tyr Cys Gln Gln Ser Arg
                    85                  90                  95
Glu Tyr Pro Tyr Thr Phe Gly Gly Gly Thr Lys Leu Glu Ile Lys Arg
            100                 105                 110

<210> SEQ ID NO 6
<211> LENGTH: 15
<212> TYPE: PRT
<213> ORGANISM: Artificial Sequence
<220> FEATURE:
<223> OTHER INFORMATION: huMov19 (M9346A) VL-CDR1

<400> SEQUENCE: 6

Lys Ala Ser Gln Ser Val Ser Phe Ala Gly Thr Ser Leu Met His
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: huMov19 (M9346A) VL-CDR2

<400> SEQUENCE: 7

Arg Ala Ser Asn Leu Glu Ala
1               5

<210> SEQ ID NO 8
<211> LENGTH: 9
<212> TYPE: PRT
<213> ORGANISM: Artificial Sequence
<220> FEATURE:
<223> OTHER INFORMATION: huMov19 (M9346A) VL-CDR3

<400> SEQUENCE: 8

Gln Gln Ser Arg Glu Tyr Pro Tyr Thr
1               5

<210> SEQ ID NO 9
<211> LENGTH: 5
<212> TYPE: PRT
<213> ORGANISM: Artificial Sequence
<220> FEATURE:
<223> OTHER INFORMATION: huMov19 (M9346A) Kabat Defined VH-CDR1

<400> SEQUENCE: 9

Gly Tyr Phe Met Asn
1               5

<210> SEQ ID NO 10
<211> LENGTH: 17
<212> TYPE: PRT
<213> ORGANISM: Artificial Sequence
<220> FEATURE:
<223> OTHER INFORMATION: huMov19 (M9346A) Kabat Defined VH-CDR2

<400> SEQUENCE: 10

Arg Ile His Pro Tyr Asp Gly Asp Thr Phe Tyr Asn Gln Lys Phe Gln
1               5                   10                  15
Gly

<210> SEQ ID NO 11
<211> LENGTH: 10
<212> TYPE: PRT
```

-continued

<213> ORGANISM: Artificial Sequence
<220> FEATURE:
<223> OTHER INFORMATION: huMov19 (M9346A) AbM Defined VH-CDR2

<400> SEQUENCE: 11

Arg Ile His Pro Tyr Asp Gly Asp Thr Phe
1               5                   10

<210> SEQ ID NO 12
<211> LENGTH: 9
<212> TYPE: PRT
<213> ORGANISM: Artificial Sequence
<220> FEATURE:
<223> OTHER INFORMATION: huMov19 (M9346A) Kabat and AbM Defined VH-CDR3

<400> SEQUENCE: 12

Tyr Asp Gly Ser Arg Ala Met Asp Tyr
1               5

<210> SEQ ID NO 13
<211> LENGTH: 448
<212> TYPE: PRT
<213> ORGANISM: Artificial Sequence
<220> FEATURE:
<223> OTHER INFORMATION: huMov19 - Heavy full-length amino acid sequence

<400> SEQUENCE: 13

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

```
Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 14
<211> LENGTH: 218
<212> TYPE: PRT
<213> ORGANISM: Artificial Sequence
<220> FEATURE:
<223> OTHER INFORMATION: huMov19 - Light version 1.00 full-length amino
      acid sequence

<400> SEQUENCE: 14

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
```

165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 15
<211> LENGTH: 218
<212> TYPE: PRT
<213> ORGANISM: Artificial Sequence
<220> FEATURE:
<223> OTHER INFORMATION: huMov19 - Light version 1.60 full-length amino
      acid sequence

<400> SEQUENCE: 15

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 16
<211> LENGTH: 17
<212> TYPE: PRT
<213> ORGANISM: Artificial Sequence
<220> FEATURE:
<223> OTHER INFORMATION: muMOV19 Kabat Defined VH-CDR2

<400> SEQUENCE: 16

Arg Ile His Pro Tyr Asp Gly Asp Thr Phe Tyr Asn Gln Asn Phe Lys
1               5                   10                  15

Asp

-continued

<210> SEQ ID NO 17
<211> LENGTH: 232
<212> TYPE: PRT
<213> ORGANISM: Homo sapiens

<400> SEQUENCE: 17

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230

<210> SEQ ID NO 18
<211> LENGTH: 26
<212> TYPE: PRT
<213> ORGANISM: Artificial Sequence
<220> FEATURE:
<223> OTHER INFORMATION: Human VEGF-A signal sequence

<400> SEQUENCE: 18

Met Asn Phe Leu Leu Ser Trp Val His Trp Ser Leu Ala Leu Leu Leu
1               5                   10                  15

Tyr Leu His His Ala Lys Trp Ser Gln Ala
            20                  25

<210> SEQ ID NO 19
<211> LENGTH: 10
<212> TYPE: PRT
<213> ORGANISM: Artificial Sequence
<220> FEATURE:
<223> OTHER INFORMATION: huMov19 (M9346A) AbM Defined VH-CDR1

<400> SEQUENCE: 19

```
Gly Tyr Thr Phe Thr Gly Tyr Phe Met Asn
1               5                   10
```

THERAPEUTIC COMBINATIONS COMPRISING ANTI-FOLR1 IMMUNOCONJUGATES

CROSS REFERENCE TO RELATED APPLICATIONS

This application claims priority to U.S. Provisional Application No. 62/220,028, filed Sep. 17, 2015; U.S. Provisional Application No. 62/242,669, filed Oct. 16, 2015; and U.S. Provisional Application No. 62/250,756, filed Nov. 4, 2015, each of which is herein incorporated by reference in its entirety.

REFERENCE TO A SEQUENCE LISTING SUBMITTED ELECTRONICALLY VIA EFS-WEB

The content of the electronically submitted sequence listing (Name: 2921_0770003_SL.txt, Size: 19,451 bytes, and Date of Creation: Sep. 13, 2016) is herein incorporated by reference in its entirety.

FIELD OF THE INVENTION

The field of the invention generally relates to combinations of an anti-FOLR1 immunoconjugate with an anti-VEGF agent, a platinum-based agent, and/or doxorubicin as well as the use of the combinations in the treatment of cancers, e.g., ovarian cancers.

BACKGROUND

Cancer is one of the leading causes of death in the developed world, with over one million people diagnosed with cancer and 500,000 deaths per year in the United States alone. Overall it is estimated that more than 1 in 3 people will develop some form of cancer during their lifetime.

Folate Receptor 1 (FOLR1), also known as Folate Receptor-alpha (FRα), or Folate Binding Protein, is a glycosyl-phosphatidylinositol (GPI)-anchored glycoprotein with a strong binding affinity for folic acid and reduced folic acid derivatives (see Leung et al., *Clin. Biochem.* 46:1462-1468 (2013)). FOLR1 mediates delivery of the physiological folate, 5-methyltetrahydrofolate, to the interior of cells. Expression of FOLR1 on normal tissues is restricted to the apical membrane of epithelial cells in the kidney proximal tubules, alveolar pneumocytes of the lung, bladder, testes, choroid plexus, and thyroid (Weitman S D, et al., *Cancer Res.* 52:3396-3401 (1992); Antony A C, *Ann. Rev. Nutr.* 16:501-521 (1996); Kalli K R, et al., *Gynecol. Oncol.* 108:619-626 (2008)). FOLR1 is overexpressed in epithelial-derived tumors including ovarian, uterine, breast, endometrial, pancreatic, renal, lung, colorectal, and brain tumors. This expression pattern of FOLR1 makes it a desirable target for FOLR1-directed cancer therapy.

Vascular endothelial growth factor-A (VEGF), also known as vascular permeability factor (VPF), is the prototype member of the VEGF family of proteins and a key regulator of angiogenesis (Hoeben et al., *Pharmacol. Rev.* 56:549-580 (2004); Ferrara et al., *Nat. Med.* 9:669-676 (2003)). Angiogenesis is the process of new blood vessel development from pre-existing vasculature and is important for at least wound healing, organ regeneration, and the female reproductive system (Hoeben et al., supra; Ferrara et al., supra). Angiogenesis is also important for several pathological processes including tumor development, growth, and metastasis (Hoeben et al., supra; Ferrara et al., supra). VEGF is a proangiogenic factor highly expressed in normal lung, kidney, heart, adrenal gland, liver, spleen, and gastric mucosa tissues and highly expressed in many human tumors (Hoeben et al., supra). Its elevation or misexpression in tumors and proangiogenic function make VEGF a desirable target for targeted cancer therapy.

Cisplatin and carboplatin, which are platinum analogues and alkylating chemotherapeutic agents, have been used alone or in combination with other agents for the treatment of a variety of solid tumors for decades (Lokich et al., *Annals. Of Oncology* 9:13-21 (1998)). Carboplatin has been reported as having reduced gastrointestinal effects as compared to cisplatin (Lokich et al.). However, carboplatin causes the negative side effect of suppressing bone marrow (Lokich et al.). Thus, improved efficacy and tolerability of treatments with cisplatin and carboplatin are desirable.

Doxorubicin, an anthracycline antibiotic chemotherapy agent, has also been used as a treatment for a variety of cancers alone or in combination with other chemotherapeutic agents such as paclitaxel (a mitotic inhibiting chemotherapeutic agent referred to as TAXOL® (Bristol Myers Squibb), see also Gehl et al., *Annals of Oncology*, 7:687-639 (1996)). The utility of doxorubicin as a cancer treatment is limited by its toxicity, in particular, doxorubicin's cardiotoxicity (see Tacar et al., *J. of Pharmacy & Pharmacology*, 65: 157-170 (2013)). Thus, improved efficacy and tolerability of treatments with doxorubicin are also desirable. A liposome-encapsulated form of the hydrochloride (HCL) salt of the doxorubicin has also been developed. Liposomal delivery of doxorubicin HCL improves drug penetration into tumors and decreases drug clearance, thereby increasing the duration of therapeutic drug effects. A liposomal formulation of doxorubicin also modulates toxicity, specifically the cardiac effects commonly seen with anthracycline antitumor drugs.

The United States Food and Drug Administration (FDA) approved the combination treatment of bevacizumab (an anti-VEGF antibody referred to as AVASTIN® (GENENTECH, INC.)) with carboplatin and paclitaxel as a first-line treatment of advanced, recurrent nonsquamous non-small cell lung cancer (NSCLC) (see Cohen et al., *Oncologist* 12:713-718 (2007)). The combination of carboplatin and paclitaxel (CP therapy) was the previous first-line treatment of NSCLC (Sandler et al., *N. Engl. J. of Medicine* 355:2542-2550 (2006)). But while the addition of bevacizumab to the CP therapy increased patient survival benefit, this triple-combination (BV/CP) therapy resulted in increased treatment-related deaths and a higher incidence of both nonhematologic and hematologic adverse events (Cohen et al., supra at Tables 4-5). More recently, bevacizumab has also been approved in combination with chemotherapeutic agents for the treatment of cervical cancer, platinum-resistant recurrent epithelial ovarian cancer, fallopian tube cancer, and primary peritoneal cancer.

There remains an unmet medical need for more effective therapies, e.g., combination therapies targeting FOLR1 expressing tumor cells, for the treatment of cancers.

BRIEF SUMMARY OF THE INVENTION

Combinations of an anti-FOLR1 immunoconjugate (e.g. IMGN853) with an anti-VEGF agent, a platinum-based agent, and/or doxorubicin are provided herein. Also provided herein are methods of treating a patient with cancer using such a combination. As described in more detail below, use of an anti-FOLR1 immunoconjugate (e.g.

IMGN853) in combination with an anti-VEGF agent, a platinum-based agent, and/or doxorubicin can result in synergistic efficacy against tumors. For example, the anti-VEGF agent, platinum-based agent, and/or doxorubicin can potentiate the efficacy of the anti-FOLR1 immunoconjugate (e.g. IMGN853) and/or the anti-FOLR1 immunoconjugate (e.g. IMGN853) can potentiate the efficacy of the anti-VEGF agent, a platinum-based agent, and/or doxorubicin. By using the combination of an anti-FOLR1 immunoconjugate (e.g. IMGN853) and an anti-VEGF agent, a platinum-based agent, and/or doxorubicin, the sum of their efficacy can be achieved even while using smaller and/or less frequent doses of the anti-FOLR1 immunoconjugate (e.g. IMGN853) and/or the anti-VEGF agent, platinum-based agent, and/or doxorubicin. Moreover, the combination can produce no more toxicity than the anti-VEGF agent, platinum-based agent, and/or doxorubicin alone, the anti-FOLR1 immunoconjugate (e.g. IMGN853) alone, and/or either the anti-VEGF agent, platinum-based agent, and/or doxorubicin or the anti-FOLR1 immunoconjugate (e.g. IMGN853).

In one instance, a method for treating a patient having a cancer comprises administering to the patient in need thereof an immunoconjugate that binds to FOLR1, wherein the immunoconjugate comprises an antibody or antigen-binding fragment thereof comprising a heavy chain variable region (VH) complementary determining region (CDR)1 sequence of SEQ ID NO:9, a VH CDR2 sequence of SEQ ID NO:10, and a VH CDR3 sequence of SEQ ID NO:12, and a light chain variable region (VL) CDR1 sequence of SEQ ID NO:6, a VL CDR2 sequence of SEQ ID NO:7, and a VL CDR3 sequence of SEQ ID NO: 8, and an anti-VEGF agent, a platinum-based agent, doxorubicin, or a combination thereof.

In one instance, a method for treating a patient having a cancer comprises administering to the patient in need thereof an immunoconjugate that binds to FOLR1, wherein the immunoconjugate comprises an antibody or antigen-binding fragment thereof comprising a VH CDR1 sequence of SEQ ID NO:19, a VH CDR2 sequence of SEQ ID NO:11, and a VH CDR3 sequence of SEQ ID NO:12, and a light chain variable region (VL) CDR1 sequence of SEQ ID NO:6, a VL CDR2 sequence of SEQ ID NO:7, and a VL CDR3 sequence of SEQ ID NO:8, and an anti-VEGF agent, a platinum-based agent, doxorubicin, or a combination thereof.

In one instance, the immunoconjugate (e.g. IMGN853) is administered in combination with the anti-VEGF agent (e.g., bevacizumab). In one instance, the immunoconjugate (e.g. IMGN853) is administered in combination with the platinum-based agent. In one instance, the immunoconjugate is administered in combination with doxorubicin.

In one instance, the immunoconjugate (e.g. IMGN853) is administered in combination with the anti-VEGF agent and the platinum-based agent. In one instance, the immunoconjugate (e.g. IMGN853) is administered in combination with the anti-VEGF agent and doxorubicin. In one instance, the immunoconjugate (e.g. IMGN853) is administered in combination with the platinum-based agent and doxorubicin.

In one instance, the immunoconjugate that binds to FOLR1 comprises an antibody or antigen-binding fragment thereof that comprises a VH comprising the sequence of SEQ ID NO:3 and a VL comprising the sequence of SEQ ID NO:5. In one instance, the antibody or antigen-binding fragment is huMov19.

In one instance, the immunoconjugate (e.g. IMGN853) comprises a cytotoxin, wherein the cytotoxin is a maytansinoid. In one instance, the maytansinoid is DM4.

In one instance, the immunoconjugate (e.g. IMGN853) comprises a linker, wherein the linker is sulfo-SPDB.

In one instance, the immunoconjugate is IMGN853.

In one instance, the administration is a first-line therapy. In one instance, the administration is a second-line therapy. In one instance, the administration is a third-line therapy.

In one instance, the immunoconjugate (e.g. IMGN853) is administered intravenously or intraperitoneally.

In one instance, administration of the immunoconjugate (e.g. IMGN853) with the anti-VEGF agent, the platinum-based agent, doxorubicin, or a combination thereof produces a synergistic effect.

In one instance, administration of the immunoconjugate (e.g. IMGN853) and the anti-VEGF agent does not produce more toxicity than administration of the immunoconjugate alone or the anti-VEGF agent alone. In one instance, administration of the immunoconjugate (e.g. IMGN853) and the platinum-based agent does not produce more toxicity than administration of the immunoconjugate alone or the platinum-based agent alone. In one instance, administration of the immunoconjugate (e.g. IMGN853) and the doxorubicin does not produce more toxicity than administration of the immunoconjugate alone or the doxorubicin alone. In one instance, administration of the immunoconjugate (e.g. IMGN853), the anti-VEGF agent, and the platinum-based agent does not produce more toxicity than the administration of a taxol, the anti-VEGF agent, or the platinum-based agent wherein the platinum-based agent is carboplatin or cisplatin.

In one instance, the immunoconjugate (e.g. IMGN853) is administered once every three weeks or once every four weeks. In one instance, the immunoconjugate (e.g. IMGN853) is administered at a dose of about 4 mg/kg adjusted ideal body weight (AIBW), at a dose of about 5 mg/kg AIBW, or at a dose of about 6 mg/kg AIBW.

In one instance, the immunoconjugate (e.g. IMGN853) is administered weekly. In one instance, the immunoconjugate (e.g. IMGN853) is administered at a dose of about 1.1 mg/kg AIBW, about 1.8 mg/kg AIBW, about 2.0 mg/kg AIBW, or about 2.5 mg/kg AIBW.

In one instance, the immunoconjugate (e.g. IMGN853) is administered once every two weeks. In one instance, the immunoconjugate (e.g. IMGN853) is administered at a dose of about 2.0 mg/kg AIBW, about 2.5 mg/kg AIBW, about 3.0 mg/kg AIBW, about 3.5 mg/kg AIBW, or about 4.0 mg/kg AIBW.

In one instance, the anti-VEGF agent comprises an antibody or antigen-binding fragment thereof that binds to VEGF or a VEGF receptor. In one instance, the antibody or antigen-binding fragment thereof that binds to VEGF is bevacizumab. In one instance, the antibody or antigen-binding fragment thereof that binds to VEGF is highly similar to bevacizumab and has no clinically meaningful differences with respect to safety and effectiveness as compared to bevacizumab (e.g., ABP 215 (Amgen), BCD-021 (Biocad)).

In one instance, the anti-VEGF agent comprises a tyrosine kinase inhibitor. In one instance, the tyrosine kinase inhibitor is selected from the group consisting of cediranib, pazopanib, axitinib, vatalanib, semaxanib, sunitinib, sorafenib, ramucirumab, and aflibercept.

In one instance, the anti-VEGF agent comprises a soluble VEGF receptor. In one instance, the soluble VEGF receptor is VEGF-TRAP.

In one instance, the anti-VEGF agent is administered once every 3 weeks or once every 2 weeks. In one instance, the anti-VEFG agent is administered at a dose of about 15 mg/kg, about 10 mg/kg, or about 7.5 mg/kg.

In one instance, the bevacizumab is administered once every 3 weeks at a dose of 15 mg/kg. In one instance, the bevacizumab is administered once every 2 weeks at a dose of 10 mg/kg.

In one instance, the platinum-based agent is carboplatin. In one instance, the carboplatin is administered once every three weeks. In one instance, the carboplatin is administered at a dose to obtain an area under the curve (AUC) of 4 mg/ml·min, 5 mg/ml min, 6 mg/ml min, or 7 mg/ml min.

In one instance, the platinum-based agent is cisplatin. In one instance, cisplatin is administered every three weeks or once every four weeks. In one instance, the cisplatin is administered at a dose of about 50-70 mg/m2, about 75-100 mg/m$^2$, or about 100 mg/m$^2$.

In one instance, the doxorubicin is pegylated doxorubicin, liposomal doxorubicin, or pegylated liposomal doxorubicin. In one instance, the doxorubicin is administered once every four weeks. In one instance, the doxorubicin is administered at a dose of 30 mg/m$^2$, 35 mg/m$^2$, 40 mg/m$^2$, 45 mg/m$^2$, or 50 mg/m$^2$.

In one instance, the anti-VEGF agent is bevacizumab, the bevacizumab is administered once every three weeks at a dose of 15 mg/kg, and the immunoconjugate (e.g. IMGN853) is administered once every three weeks at a dose of 4 mg/kg AIBW. In one instance, the anti-VEGF agent is bevacizumab, the bevacizumab is administered once every three weeks at a dose of 15 mg/kg, and the immunoconjugate (e.g. IMGN853) is administered once every three weeks at a dose of 5 mg/kg AIBW. In one instance, the anti-VEGF agent is bevacizumab, the bevacizumab is administered once every three weeks at a dose of 15 mg/kg, and the immunoconjugate (e.g. IMGN853) is administered once every three weeks at a dose of 6 mg/kg AIBW.

In one instance, the anti-VEGF agent is bevacizumab, the bevacizumab is administered once every two weeks at a dose of 10 mg/kg, and the immunoconjugate (e.g. IMGN853) is administered once every four weeks at a dose of 4 mg/kg AIBW. In one instance, the anti-VEGF agent is bevacizumab, the bevacizumab is administered once every two weeks at a dose of 10 mg/kg, and the immunoconjugate (e.g. IMGN853) is administered once every four weeks at a dose of 5 mg/kg AIBW. In one instance, the anti-VEGF agent is bevacizumab, the bevacizumab is administered once every two weeks at a dose of 10 mg/kg, and the immunoconjugate (e.g. IMGN853) is administered once every four weeks at a dose of 6 mg/kg AIBW.

In one instance, carboplatin is administered with the bevacizuamb and the immunoconjugate (e.g. IMGN853). In one instance, carboplatin is administered once every three weeks. In one instance, carboplatin is administered at a dose to obtain an area under the curve (AUC) of 4 mg/ml·min, 5 mg/ml min, 6 mg/ml min, or 7 mg/ml min.

In one instance, the platinum-based agent is carboplatin, the carboplatin is administered once every three weeks to obtain an AUC of 4 mg/ml·min, and the immunoconjugate (e.g. IMGN853) is administered once every three weeks at a dose of 4 mg/kg AIBW.

In one instance, the platinum-based agent is carboplatin, the carboplatin is administered once every three weeks to obtain an AUC of 4 mg/ml·min, and the immunoconjugate (e.g. IMGN853) is administered once every three weeks at a dose of 5 mg/kg AIBW.

In one instance, the platinum-based agent is carboplatin, the carboplatin is administered once every three weeks to obtain an AUC of 5 mg/ml·min, and the immunoconjugate (e.g. IMGN853) is administered once every three weeks at a dose of 5 mg/kg AIBW.

In one instance, the platinum-based agent is carboplatin, the carboplatin is administered once every three weeks to obtain an AUC of 5 mg/ml·min, and the immunoconjugate (e.g. IMGN853) is administered once every three weeks at a dose of 6 mg/kg AIBW.

In one instance, the doxorubicin is pegylated liposomal doxorubicin (PLD), the PLD is administered once every four weeks at a dose of about 30 mg/m$^2$, and the immunoconjugate (e.g. IMGN853) is administered once every four weeks at a dose of 4 mg/kg AIBW.

In one instance, the doxorubicin is PLD, the PLD is administered once every four weeks at a dose of about 30 mg/m$^2$, and the immunoconjugate (e.g. IMGN853) is administered once every four weeks at a dose of 5 mg/kg AIBW.

In one instance, the doxorubicin is PLD, the PLD is administered once every four weeks at a dose of about 40 mg/m$^2$, and the immunoconjugate (e.g. IMGN853) is administered once every four weeks at a dose of 5 mg/kg AIBW.

In one instance, the doxorubicin is PLD, the PLD is administered once every four weeks at a dose of about 40 mg/m$^2$, and the immunoconjugate (e.g. IMGN853) is administered once every four weeks at a dose of 6 mg/kg AIBW.

In one instance, the cancer is ovarian, peritoneal, fallopian, endometrial, or lung cancer.

In one instance, the cancer is ovarian cancer. In one instance, the ovarian cancer is epithelial ovarian cancer. In one instance, the ovarian cancer is platinum resistant, relapsed, or refractory.

In one instance, the cancer is platinum refractory. In one instance, the cancer is primary platinum refractory. In one instance, the cancer is platinum sensitive.

In one instance, the cancer is platinum-resistant recurrent epithelial ovarian, fallopian tube, or primary peritoneal cancer.

In one instance, the cancer is ovarian cancer and the administration results in a decrease in CA125. In one instance, the peritoneal cancer is primary peritoneal cancer. In one instance, the endometrial cancer is serous endometrial cancer. In one instance, the lung cancer is selected from the group consisting of non-small cell lung cancer (NSCLC), adenocarcinoma, and bronchioloalveolar carcinoma.

In one instance the cancer has previously been treated with bevacuzimab. In one instance, the cancer has not previously been treated with bevacuzimab (i.e., the patient is "bevacuzimab naive").

In one instance, the cancer is metastatic or advanced.

In one instance, the cancer expresses FOLR1. In one instance, the FOLR1 expression is measured by immunohistochemistry (IHC). In one instance, the IHC has a staining score of at least 1 hetero, at least 1 homo, at least 2 hetero, at least 2 homo, or at least 3 hetero. In one instance, at least 25%, at least 33%, at least 50%, at least 66%, or at least 75% of cells in a sample obtained from the patient have an IHC staining score of at least 2 (moderate). In one instance, at least 25%, at least 33%, at least 50%, at least 66%, or at least 75% of cells in a sample obtained from the patient have an IHC staining score of at least 3.

In one instance, the method further comprises administering a steroid to the patient. In one instance, the steroid is dexamethasone. In one instance, a steroid is administered in an eye drop. In one instance, the eye drop is a preservative-free, lubricating eye drop.

In one instance, the immunoconjugate (e.g. IMGN853) and the anti-VEGF agent, platinum-based agent, doxorubicin, or a combination thereof are administered in separate pharmaceutical compositions.

Also provided herein are kits. In one instance, a kit comprises an immunoconjugate that binds to FOLR1, wherein the immunoconjugate comprises an antibody or antigen binding fragment thereof comprising a VH CDR1 sequence of SEQ ID NO:9, a VH CDR2 sequence of SEQ ID NO:10, and a VH CDR3 sequence of SEQ ID NO:12, and a VL CDR1 sequence of SEQ ID NO:6, a VL CDR2 sequence of SEQ ID NO:7, and a VL CDR3 sequence of SEQ ID NO:8; and an anti-VEGF agent, a platinum-based agent, or doxorubicin; and instructions to administer the immunoconjugate with the anti-VEGF agent, the platinum-based agent, or doxorubicin. In one instance, the anti-VEGF agent is an anti-VEGF antibody. In one instance, the anti-VEGF antibody is bevacizumab. In one instance, the anti-VEGF agent is a tyrosine kinase inhibitor. In one instance, the tyrosine kinase inhibitor is selected from the group consisting of cediranib, pazopanib, axitinib, vatalanib, semaxanib, sunitinib, sorafenib, ramucirumab, and aflibercept. In one instance, the anti-VEGF agent is a soluble VEGF receptor. In one instance, the soluble VEGF receptor is VEGF-TRAP. In one instance, the platinum-based agent is carboplatin or cisplatin. In one instance, the doxorubicin is pegylated liposomal doxorubicin. In one instance, the immunoconjugate is IMGN853.

Also provided herein are methods of instructing a human subject with cancer. In one instance, the method comprises providing instructions to receive cancer treatment with an immunoconjugate (e.g. IMGN853) that binds to FOLR1 and an anti-VEGF agent, a platinum-based agent, doxorubicin, or a combination thereof. In one instance, the anti-VEGF agent is an anti-VEGF antibody. In one instance, the anti-VEGF antibody is bevacizumab. In one instance, the anti-VEGF agent is a tyrosine kinase inhibitor. In one instance, the tyrosine kinase inhibitor is selected from the group consisting of cediranib, pazopanib, axitinib, vatalanib, semaxanib, sunitinib, sorafenib, ramucirumab, and aflibercept. In one instance, the anti-VEGF agent is a soluble VEGF receptor. In one instance, the soluble VEGF receptor is VEGF-TRAP. In one instance, the platinum-based agent is carboplatin or cisplatin. In one instance, the doxorubicin is pegylated liposomal doxorubicin. In one instance, the immunoconjugate is IMGN853.

BRIEF DESCRIPTION OF THE FIGURES

FIG. 2A shows the antitumor activity of IMGN853 (5 mg/kg), bevacizumab (5 mg/kg), and IMGN853+bevacizumab combination therapy in a serous ovarian cancer tumor model.

FIG. 2B shows the antitumor activity of IMGN853 (2.5 mg/kg), bevacizumab (5 mg/kg), and IMGN853+bevacizumab combination therapy in a serous ovarian cancer tumor model.

FIG. 9A shows IGROV-1 cells treated with graded concentrations of IMGN853, carboplatin, or both and the effects on proliferation. The Combination Index (CI) was calculated using Median Effect analysis. Data from two independent experiments are shown, determined for a range of drug concentrations and a fractional effect (Fa) of 0.4 to 0.7. Data points below the dotted line represent synergy between the drug pairs.

FIG. 9B shows IGROV-1 cells treated with carboplatin (20 µM) or IMGN853 (8 nM), both alone and in combination, for 6 hours. Cells were washed, and cell cycle distribution determined following 24 hour culture in drug-free medium.

FIG. 9C shows IGROV-1 cells exposed to carboplatin (40 µM) or IMGN853 (16 nM), alone or in combination, for 6 hours followed by incubation in drug-free medium for an additional 18 hours. Cellular extracts were immunoblotted for γH2AX or actin (loading control) as indicated.

FIG. 9D shows the antitumor activity of IMGN853 (2.5 mg/kg) or carboplatin (80 mg/kg), alone and in combination (n=7 mice/group) in platinum-sensitive ovarian cancer patient derived xenografts (PDXs) established in SCID mice. Data are expressed as mean and standard error of the mean (SEM) for each time point.

FIG. 9E shows the antitumor activity of two consecutive weekly doses of vehicle, carboplatin (80 mg/kg, i.p.) plus paclitaxel (10 mg/kg), carboplatin plus PLD (4 mg/kg), or carboplatin plus IMGN853 (5 mg/kg) in mice bearing platinum-sensitive PDX tumors (n=7 mice/group).

DETAILED DESCRIPTION OF THE INVENTION

Figure 1:
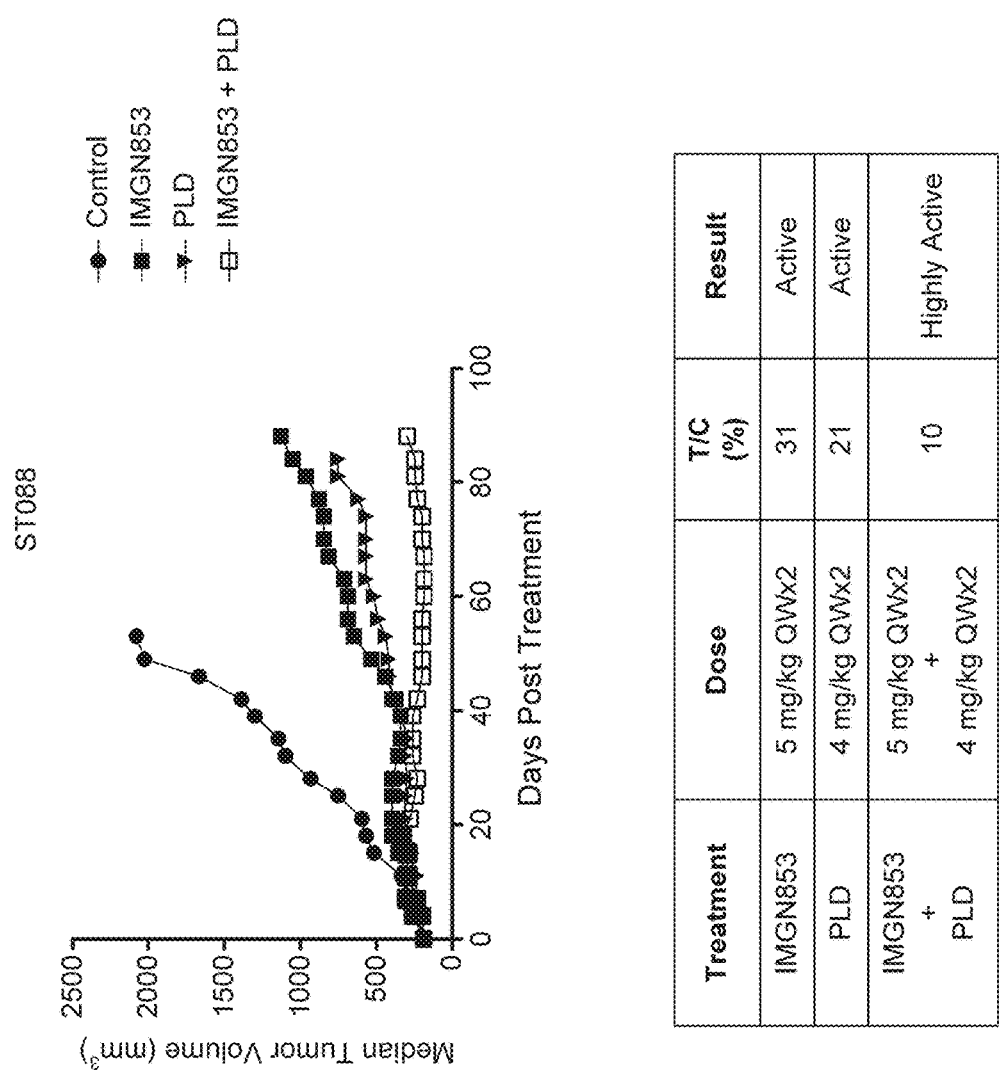
FIG. 1 shows the antitumor activity of IMGN853 (5 mg/kg), pegylated liposomal doxorubicin (PLD) (4 mg/kg), and IMGN853+PLD combination therapy in an epithelial ovarian cancer tumor model.

The present invention provides combinations of an anti-FOLR1 immunoconjugate with an anti-VEGF agent, a platinum-based agent, doxorubicin, or a combination thereof and the use of the combinations in the treatment of cancer.

I. Definitions

To facilitate an understanding of the present invention, a number of terms and phrases are defined below.

The term "FOLR1" as used herein refers to any native human FOLR1 polypeptide, unless otherwise indicated. FOLR1 is also referred to as "human folate receptor 1." "folate receptor alpha (FR-α)," and "FRα". The term "FOLR1" encompasses "full-length," unprocessed FOLR1 polypeptide as well as any form of FOLR1 polypeptide that results from processing within the cell. The term also encompasses naturally occurring variants of FOLR1, e.g., those encoded by splice variants and allelic variants. The FOLR1 polypeptides described herein can be isolated from a variety of sources, such as from human tissue types or from another source, or prepared by recombinant or synthetic methods. Where specifically indicated, "FOLR1" can be used to refer to a nucleic acid that encodes a FOLR1 polypeptide. Human FOLR1 sequences are known and include, for example, the sequences publically available at UniProtKB Accession No. P15328 (including isoforms). As used herein, the term "human FOLR1" refers to FOLR1 comprising the sequence of SEQ ID NO:1.

The term "VEGF" as used herein, refers to any native human VEGF polypeptide, unless otherwise indicated. VEGF is also referred to as Vascular Endothelial Growth Factor-A, VEGF-A, Vascular Permeability Factor, and VPF. The term "VEGF" encompasses "full-length," unprocessed VEGF polypeptide as well as any form of VEGF polypeptide that results from processing in the cell. The term also encompasses naturally occurring variants of VEGF, e.g., those encoded by splice variants and allelic variants. The VEGF polypeptides described herein can be isolated from a variety of sources, such as from human tissue types or from another source, or prepared by recombinant or synthetic methods. Where specifically indicated, "VEGF" can be used to refer to a nucleic acid that encodes a VEGF polypeptide. Human VEGF sequences are known and include, for example, the sequences publically available at UniProtKB Accession No. P15692 (including isoforms).

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" refers to a portion of an intact antibody. An "antigen-binding fragment" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, and single chain antibodies.

A "blocking" antibody or an "antagonist" antibody is one which inhibits or reduces biological activity of the antigen it binds, such as FOLR1 or VEGF. In some embodiments, blocking antibodies or antagonist antibodies substantially or completely inhibit the biological activity of the antigen. The biological activity can be reduced by 10%, 20%, 30%, 50%, 70%, 80%, 90%, 95%, or even 100%.

The term "anti-FOLR1 antibody" or "an antibody that binds to FOLR1" refers to an antibody that is capable of binding FOLR1 with sufficient affinity such that the antibody is useful as a diagnostic and/or therapeutic agent in targeting FOLR1 (e.g., the huMov19 (M9346A) antibody). The extent of binding of an anti-FOLR1 antibody to an unrelated, non-FOLR1 protein can be less than about 10% of the binding of the antibody to FOLR1 as measured, e.g., by a radioimmunoassay (RIA).

The term "anti-VEGF agent" refers to agents that are capable of inhibiting the VEGF pathway. Anti-VEGF agents include, for example, anti-VEGF antibodies (e.g., Bevacizumab, ABP 215 (Amgen), BCD-021 (Biocad), etc.) or anti-VEGFR antibodies (e.g., ramucirumab), tyrosine Kinase Inhibitors (TKIs) (e.g., Cediranib or RECENTIN® (IPR Pharmaceuticals Inc.), see Nikolinakos et al., *J. Thoracic Oncology* 3(6) Suppl. 2: S131-S134 (2008)), and soluble VEGF receptors (e.g., VEGF-Trap; see, e.g., Holash et al., *PNAS* 99(17) 11393-11398 (2002)).

The term "anti-VEGF antibody" or "an antibody that binds to VEGF" refers to an antibody that is capable of binding VEGF with sufficient affinity such that the antibody is useful as a therapeutic agent in targeting VEGF (e.g., bevacizumab). The extent of binding of an anti-VEGF antibody to an unrelated, non-VEGF protein can be less than about 10% of the binding of the antibody to VEGF as measured, e.g., by a radioimmunoassay (RIA). In certain embodiments, an antibody that binds to VEGF has a dissociation constant (Kd) of ≤1 µM, ≤100 nM, ≤10 nM, ≤1 nM, or ≤0.1 nM. In certain embodiments, the antibody or antigen-binding fragment thereof that binds to VEGF is bevacizumab. In certain embodiments, the antibody or antigen-binding fragment thereof that binds to VEGF is highly similar to bevacizumab and has no clinically meaningful differences with respect to safety and effectiveness as compared to bevacizumab (e.g., ABP 215 (Amgen), BCD-021 (Biocad)).

The term "Bevacizumab" refers to a specific anti-VEGF antibody. Bevacizumab is a recombinant humanized monoclonal IgG$_1$ antibody that comprises antigen-binding complementarity-determining regions derived from the murine anti-VEGF monoclonal antibody A.4.6.1 (see Presta et al., *Cancer Res.* 57:4593-4599 (1997); U.S. Pat. No. 6,054,297; U.S. Pat. No. 7,365,166; U.S. Pat. No. 7,622,115; U.S. Pat. No. 8,778,340). Bevacizumab is the active ingredient in Avastin® (Genentech, Inc.) (Id.).

The term "paclitaxel" or "PAC" refers to the compound associated with CAS Registry Number 33069-62-4. Paclitaxel is the active ingredient in TAXOL® (Bristol-Myers Squibb Company), Onxol, and ABRAXANE® (Abraxis Bioscience, LLC). Paclitaxel is believed to be a mitotic inhibiting chemotherapy agent that binds tubulin and inhibits the disassembly of microtubules to prevent cell division and induce apoptosis.

The term "platinum-based agent" refers to platinum-based chemotherapeutic agents. Platinum-based agents include cisplatin, carboplatin, and oxaliplatin.

The term "cisplatin" refers to the compound associated with CAS Registry Number for 15663-27-1. Cisplatin is the active ingredient in PLATINOL® (Bristol-Myers Company), and cisplatin is also referred to as "cisplatinum." Cisplatin is believed to be a platinum-containing, alkylating chemotherapy agent that binds to nucleophilic groups in DNA and causes intrastrand and interstrand DNA crosslinks, as well as DNA-protein crosslinks, that result in apoptosis and cell growth inhibition.

The term "carboplatin" or "Carbo" refers to the compound associated with CAS Registry Number 41575-94-4. Carboplatin is the active ingredient in PARAPLATIN® (Bristol-Myers Squibb Co., Corp.). Carboplatin contains a platinum atom complexed with two ammonia groups and a cyclobutane-dicarboxyl residue. This agent is activated intracellularly to form reactive platinum complexes that bind to nucleophilic groups such as GC-rich sites in DNA, thereby inducing intrastrand and interstrand DNA cross-links, as well as DNA-protein cross-links. These carboplatin-induced DNA and protein effects result in apoptosis and cell growth inhibition. This agent possesses tumoricidal activity similar to that of its parent compound, cisplatin, but is more stable and less toxic.

The term "doxorubicin" refers to the compound associated with CAS Registry Number 23214-92-8. Doxorubicin is also referred to as "hydroxydaunorubicin" or "doxorubicin hydrochloride." Doxorubicin is the active ingredient in "Adriamycin" and "Rubex." Liposomal doxorubicin (i.e., doxorubicin encapsulated in a lipid sphere or liposome) is the active ingredient in MYOCET® (Cephalon UK, Ltd.). Pegylated liposomal doxorubicin (PLD) (liposomal doxorubicin to which polyethylene glycol polymers have been attached) is the active ingredient in DOXIL® (Liposom Technology, Inc.) and "Caelyx® (Janssen)." Doxorubicin is believed to be an anthracycline antibiotic chemotherapy agent that intercalates between base pairs in the DNA helix to prevent DNA replication. Additionally, doxorubicin inhibits topoisomerase II which results in an increased and stabilized cleavable enzyme-DNA linked complex during DNA replication and subsequently prevents the ligation of the nucleotide strand after double-strand breakage. Doxorubicin also forms oxygen free radicals resulting in cytotoxicity secondary to lipid peroxidation of cell membrane lipids.

The terms "line of treatment" or "line of therapy" refer to a therapeutic regimen that can include but is not limited to surgery, radiation therapy, chemotherapy, differentiating therapy, biotherapy, immune therapy, or the administration of one or more anti-cancer agents (e.g., a cytotoxic agent, an anti-proliferative compound, and/or an angiogenesis inhibitor).

The terms "first-line treatment," "first-line therapy," and "front-line therapy" refer to the preferred and standard initial treatment for a particular condition, e.g., a given type and stage of cancer. These treatments differ from "second-line" therapies, which are tried when a first-line therapy does not work adequately. "Third-line" therapies are tried when a first-line therapy and a second-line therapy do not work adequately.

For example, the combination of an anti-FOLR1 immunoconjugate (e.g. IMGN853) with an anti-VEGF agent, a platinum-based agent, and/or doxorubicin provided herein can be given as a first-line therapy, a second-line therapy (e.g., in patients with platinum sensitive or platinum resistant epithelial ovarian, fallopian tube, or primary peritoneal cancer), or a third-line therapy (e.g., in patients with platinum sensitive or platinum resistant epithelial ovarian, fallopian tube, or primary peritoneal cancer). The combination of a FOLR1 immunoconjugate (e.g. IMGN853) with an anti-VEGF agent, a platinum-based agent, and/or doxorubicin provided herein can be given as a line of therapy in patients having received 0, 1, 2, 3, 4, 5, 6, or more lines of therapy prior to treatment with the combination of a FOLR1 immunoconjugate (e.g. IMGN853) and an anti-VEGF agent, a platinum-based agent, and/or doxorubicin provided herein. The combination of a FOLR1 immunoconjugate (e.g. IMGN853) with an anti-VEGF agent, a platinum-based agent, and/or doxorubicin provided herein can be given as a line of therapy in patients having received at least 1, at least 2, or at least 3 lines of therapy prior to treatment with the combination of a FOLR1 immunoconjugate (e.g. IMGN853) and an anti-VEGF agent, a platinum-based agent, and/or doxorubicin provided herein. In some embodiments, the combination of a FOLR1 immunoconjugate (e.g. IMGN853) and an anti-VEGF agent, a platinum-based agent, and/or doxorubicin provided herein can be given as a line of therapy in patients having received no more than 1, no more than 2, no more than 3, no more than 4, no more than 5, or no more than 6 lines of therapy. In certain embodiments, the combination of a FOLR1 immunoconjugate (e.g. IMGN853) and an anti-VEGF agent, a platinum-based agent, and/or doxorubicin provided herein can be given as an adjuvant therapy or a neoadjuvant therapy.

The term "adjuvant therapy" refers to systemic therapy given after surgery. Adjuvant therapy, in the broadest sense, is treatment given in addition to the primary therapy to kill any cancer cells that may have spread, even if the spread cannot be detected by radiologic or laboratory tests.

The term "neoadjuvant therapy" refers to systemic therapy given prior to surgery.

The term "IMGN853" refers to the immunoconjugate described herein containing the huMov19 (M9346A) antibody, the sulfoSPDB linker, and the DM4 maytansinoid. The huMov19 (M9346A) antibody is an anti-FOLR1 antibody comprising the variable heavy chain sequence SEQ ID NO:3 and the variable light chain sequence SEQ ID NO:5. DM4 refers to N2'-deacetyl-N2'-(4-mercapto-4-methyl-1-oxopentyl) maytansine. "SulfoSPDB" refers to the N-succinimidyl 4-(2-pyridyldithio)-2-sulfobutanoate) linker.

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal" antibody or antigen-binding fragment thereof refers to such antibodies and antigen-binding fragments thereof made in any number of manners including but not limited to by hybridoma, phage selection, recombinant expression, and transgenic animals.

The term "humanized" antibody or antigen-binding fragment thereof refers to forms of non-human (e.g. murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementary determining region (CDR) are replaced by residues from the CDR of a non-human species (e.g. mouse, rat, rabbit, hamster) that have the desired specificity, affinity, and capability ("CDR grafted") (Jones et al., *Nature* 321:522-525 (1986); Riechmann et al., *Nature* 332:323-327 (1988); Verhoeyen et al., *Science* 239:1534-1536 (1988)). In some instances, the Fv framework region (FR) residues of a human immunoglobulin are replaced with the corresponding residues in an antibody or fragment from a non-human species that has the desired specificity, affinity, and capability. The humanized antibody or antigen-binding fragment thereof can be further modified by the substitution of additional residues either in the Fv framework region and/or within the replaced non-human residues to refine and optimize antibody or antigen-binding fragment thereof specificity, affinity, and/or capability. In general, the humanized antibody or antigen-binding fragment thereof will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., *Proc. Natl. Acad. Sci., USA*, 91(3):969-973 (1994), and Roguska et al., *Protein Eng.* 9(10):895-904 (1996). In some embodiments, a "humanized antibody" is a resurfaced antibody.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al., *Sequences of Proteins of Immunological Interest*, (5th ed., 1991, National Institutes of Health, Bethesda Md.), "Kabat"); and (2) an approach based on crystallographic studies of antigen-antibody complexes (Al-lazikani et al, *J. Molec. Biol.* 273:927-948 (1997)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., *Sequences of Immunological Interest*. (5th Ed., 1991, National Institutes of Health, Bethesda, Md.) ("Kabat").

The amino acid position numbering as in Kabat, refers to the numbering system used for heavy chain variable domains or light chain variable domains of the compilation of antibodies in Kabat et al. (*Sequences of Immunological Interest*. (5th Ed., 1991, National Institutes of Health, Bethesda, Md.), "Kabat"). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk, *J. Mol. Biol.* 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |

| Loop | Kabat | AbM | Chothia |
|---|---|---|---|
| H1 | H31-H35B | H26-H35B (Kabat Numbering) | H26-H32 ... 34 |
| H1 | H31-H35 | H26-H35 (Chothia Numbering) | H26-H32 |
| H2 | H50-H65 | H50-H58 | H52-H56 |
| H3 | H95-H102 | H95-H102 | H95-H102 |

The term "human" antibody or antigen-binding fragment thereof means an antibody or antigen-binding fragment thereof produced by a human or an antibody or antigen-binding fragment thereof having an amino acid sequence corresponding to an antibody or antigen-binding fragment thereof produced by a human made using any technique known in the art. This definition of a human antibody or antigen-binding fragment thereof includes intact or full-length antibodies and fragments thereof.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g. mouse, rat, rabbit, etc.) with the desired specificity, affinity, and capability while the constant regions are homologous to the sequences in antibodies or antigen-binding fragments thereof derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to that epitope or an overlapping epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values can be less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The term "immunoconjugate" or "conjugate" as used herein refers to a compound or a derivative thereof that is linked to a cell binding agent (i.e., an anti-FOLR1 antibody or fragment thereof) and is defined by a generic formula: C-L-A, wherein C=cytotoxin, L=linker, and A=antibody or antigen-binding fragment thereof e.g., an anti-FOLR1 antibody or antibody fragment. Immunoconjugates can also be defined by the generic formula in reverse order: A-L-C.

A "linker" is any chemical moiety that is capable of linking a compound, usually a drug (such as a maytansinoid), to a cell-binding agent (such as an anti FOLR1 antibody or a fragment thereof) in a stable, covalent manner. Linkers can be susceptible to or be substantially resistant to, e.g., disulfide bond cleavage, at conditions under which the compound or the antibody remains active. Suitable linkers are well known in the art and include, for example, disulfide groups and thioether groups.

The terms "cancer" and "cancerous" refer to or describe the physiological condition in mammals in which a population of cells are characterized by unregulated cell growth. Examples of cancer include, but are not limited to, carcinoma, blastoma, and sarcoma. More particular examples of such cancers include squamous cell cancer, small-cell lung cancer, non-small cell lung cancer, adenocarcinoma of the lung, squamous carcinoma of the lung, peritoneal cancer including primary peritoneal cancer (PPC), hepatocellular cancer, gastrointestinal cancer, pancreatic cancer, glioblastoma, cervical cancer, ovarian cancer (including epithelial ovarian cancer (EOC) and advanced EOC), liver cancer, bladder cancer, hepatoma, breast cancer, colon cancer, colorectal cancer, endometrial cancer (or uterine carcinoma), salivary gland carcinoma, non-clear cell kidney (renal) cancer, prostate cancer, vulval cancer, thyroid cancer, hepatic carcinoma, various types of head and neck cancers, bone, pituitary, testicle, and brain cancers (see, e.g., U.S. Pat. No. 8,709,432); U.S. Pat. No. 8,834,877; Zwicke et al., *Nano Reviews* 3:18496-18506 (2012)). The cancer can be a cancer that expresses FOLR1 ("FOLR1-expressing cancer" or "FRα positive" cancer).

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

An "advanced" cancer is one which has spread outside the site or organ of origin, either by local invasion or metastasis. The term "advanced" cancer includes both locally advanced and metastatic disease.

"Metastatic" cancer refers to cancer that has spread from one part of the body) to another part of the body.

A "refractory" cancer is one that progresses even though an anti-tumor treatment, such as a chemotherapy, is administered to the cancer patient. An example of a refractory cancer is one which is platinum refractory.

A patient is "platinum-refractory" if the patient does not respond to platinum-based therapy and shows progression during the course of therapy or within 4 weeks after the last dose. "Platinum-resistant" patients progress within 6 months of platinum-based therapy. "Partially platinum-sensitive" patients progress between 6 and 12 months of platinum-based therapy. "Platinum-sensitive" patients progress within an interval of more than 12 months.

A "recurrent" cancer is one that has regrown, either at the initial site or at a distant site, after a response to initial therapy.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

A "relapsed" patient is one who has signs or symptoms of cancer after remission. Optionally, the patient has relapsed after adjuvant or neoadjuvant therapy.

Administration "in combination with" one or more further therapeutic agents includes simultaneous (concurrent) or consecutive administration in any order.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered serially, by alternation, or in parallel as separate formulations; or (3) by some other regimen. When delivered in alternation therapy, a synergistic effect can be attained when the compounds are administered or delivered sequentially, e.g., by different injections in separate syringes.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

An "effective amount" of an antibody, immunoconjugate, or other drug as disclosed herein is an amount sufficient to carry out a specifically stated purpose. An "effective amount" can be determined empirically and in a routine manner, in relation to the stated purpose.

The term "therapeutically effective amount" refers to an amount of an antibody, immunoconjugate, or other drug effective to "treat" a disease or disorder in a subject or mammal. In the case of cancer, the therapeutically effective amount of the drug can reduce the number of cancer cells; reduce the tumor size or burden; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; relieve to some extent one or more of the symptoms associated with the cancer; and/or result in a favorable response such as increased progression-free survival (PFS), disease-free survival (DFS), or overall survival (OS), complete response (CR), partial response (PR), or, in some cases, stable disease (SD), a decrease in progressive disease (PD), a reduced time to progression (TTP), a decrease in CA125 in the case of ovarian cancer or any combination thereof. See the definition herein of "treating". To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "respond favorably" generally refers to causing a beneficial state in a subject. With respect to cancer treatment, the term refers to providing a therapeutic effect on the subject. Positive therapeutic effects in cancer can be measured in a number of ways (See, W. A. Weber, *J. Nucl. Med.* 50:1S-10S (2009)). For example, tumor growth inhibition, molecular marker expression, serum marker expression, and molecular imaging techniques can all be used to assess therapeutic efficacy of an anti-cancer therapeutic. $Log_{10}$ Cell Kill (LCK) can be used to quantify the tumor cell kill. $Log_{10}$ cell kill (LCK) is calculated with the formula LCK=(T−C)/$T_d$×3.32, where (T−C) (or tumor growth delay (TGD)) is the median time (in days) for the treatment group and control group tumors to reach a predetermined size (tumor-free survivors excluded). $T_d$ is the tumor doubling time (estimated from nonlinear exponential curve fit of daily median of control tumor growth), and 3.32 is the number of cell doublings per log of cell growth. The ability to reduce tumor volume may be assessed, for example, by measuring a % T/C value, which is the median tumor volume of treated subjects divided by the median tumor volume of the control subjects. With respect to tumor growth inhibition, according to NCI standards, a T/C≤42% is the minimum level of anti-tumor activity. A T/C<10% is considered a high anti-tumor activity level, with T/C (%)=Median tumor volume of the treated/Median tumor volume of the control×100. A favorable response can be assessed, for example, by increased progression-free survival (PFS), disease-free survival (DFS), or overall survival (OS), complete response (CR), partial response (PR), or, in some cases, stable disease (SD), a decrease in progressive disease (PD), a reduced time to progression (TTP), a decrease in CA125 in the case of ovarian cancer, or any combination thereof.

PFS, DFS, and OS can be measured by standards set by the National Cancer Institute and the U.S. Food and Drug Administration for the approval of new drugs. See Johnson et al, *J. Clin. Oncol.* 21(7):1404-1411 (2003).

"Progression free survival" (PFS) refers to the time from enrollment to disease progression or death. PFS is generally measured using the Kaplan-Meier method and Response Evaluation Criteria in Solid Tumors (RECIST) 1.1 standards. Generally, progression free survival refers to the situation wherein a patient remains alive, without the cancer getting worse.

"Time to Tumor Progression" (TTP) is defined as the time from enrollment to disease progression. TTP is generally measured using the RECIST 1.1 criteria.

A "complete response" or "complete remission" or "CR" indicates the disappearance of all signs of tumor or cancer in response to treatment. This does not always mean the cancer has been cured.

A "partial response" or "PR" refers to a decrease in the size or volume of one or more tumors or lesions, or in the extent of cancer in the body, in response to treatment.

"Stable disease" refers to disease without progression or relapse. In stable disease there is neither sufficient tumor shrinkage to qualify for partial response nor sufficient tumor increase to qualify as progressive disease.

"Progressive disease" refers to the appearance of one more new lesions or tumors and/or the unequivocal progression of existing non-target lesions. Progressive disease can also refer to a tumor growth of more than 20% since treatment began, either due to an increases in mass or in spread of the tumor.

"Disease free survival" (DFS) refers to the length of time during and after treatment that the patient remains free of disease.

"Overall Survival" (OS) refers to the time from patient enrollment to death or censored at the date last known alive. OS includes a prolongation in life expectancy as compared to naive or untreated individuals or patients. Overall survival refers to the situation wherein a patient remains alive for a defined period of time, such as one year, five years, etc., e.g., from the time of diagnosis or treatment.

By "extending survival" or "increasing the likelihood of survival" is meant increasing PFS and/or OS in a treated subject relative to an untreated subject or relative to a control treatment protocol, such as those used in the standard of care for a type of cancer.

A "decrease in CA125 levels" can be assessed according to the Gynecologic Cancer Intergroup (GCIG) guidelines. For example, CA125 levels can be measured prior to treatment to establish a baseline CA125 level. CA125 levels can be measured one or more times during or after treatment, and a reduction in the CA125 levels over time as compared to the baseline level is considered a decrease in CA125 levels.

The term "increased expression" or "overexpression" of FOLR1 in a particular tumor, tissue, or cell sample refers to FOLR1 (a FOLR1 polypeptide or a nucleic acid encoding such a polypeptide) that is present at a level higher than that which is present in a healthy or non-diseased (native, wild type) tissue or cells of the same type or origin. Such increased expression or overexpression can be caused, for example, by mutation, gene amplification, increased transcription, increased translation, or increased protein stability.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder. In certain embodiments, a subject is successfully "treated" for cancer according to the methods of the present invention if the patient shows one or more of the following: a reduction in the number of or complete absence of cancer cells; a reduction in the tumor burden; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; increased progression-free survival (PFS), disease-free survival (DFS), or overall survival (OS), complete response (CR), partial response (PR), stable disease (SD), a decrease in progressive disease (PD), a reduced time to progression (TTP), a decrease in CA125 in the case of ovarian cancer, or any combination thereof.

Prophylactic or preventative measures refer to measures that prevent and/or slow the development of a targeted pathological condition or disorder. Thus, those in need of prophylactic or preventative measures include those prone to have the disorder and those in whom the disorder is to be prevented.

The term "instructing" means providing directions for applicable therapy, medication, treatment, treatment regimens, and the like, by any means, for example, in writing, such as in the form of package inserts or other written promotional material.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, *Proc. Natl. Acad. Sci.*, 87:2264-2268 (1990), as modified in Karlin et al., *Proc. Natl. Acad. Sci.*, 90:5873-5877 (1993), and incorporated into the NBLAST and XBLAST programs (Altschul et al., *Nucleic Acids Res.*, 25:3389-3402 (1991)). In certain embodiments, Gapped BLAST can be used as described in Altschul et al., *Nucleic Acids Res.* 25:3389-3402 (1997). BLAST-2, WU-BLAST-2 (Altschul et al., *Methods in Enzymology*, 266:460-480 (1996)), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna. CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48):444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (*CABIOS*, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman (*Advances in Applied Mathematics* 2: 482 489 (1981)) to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value there between, and can be over a longer region than 60-80 residues, for example, at least about 90-100 residues, and in some embodiments, the sequences are substantially identical over the full length of the sequences being compared, such as the coding region of a nucleotide sequence for example.

A "conservative amino acid substitution" is one in which one amino acid residue is replaced with another amino acid residue having a similar side chain Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies of the invention do not abrogate the binding of the polypeptide or antibody containing the amino acid sequence, to the antigen(s), i.e., the FOLR1 or VEGF to which the polypeptide or antibody binds. Methods of identifying nucleotide and amino acid conservative substitutions which do not eliminate antigen binding are well-known in the art (see, e.g., Brummell et al., *Biochem.* 32: 1180-1 187 (1993); Kobayashi et al., *Protein Eng.* 12(10):879-884 (1999); and Burks et al., *Proc. Natl. Acad. Sci. USA* 94:412-417 (1997)).

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Anti-FOLR1 Immunoconjugates

Described herein are methods of administering immunoconjugates that specifically bind FOLR1 (e.g., IMGN853). These agents are referred to herein as "FOLR1-immunoconjugates or anti-FOLR1 immunoconjugates." The amino acid and nucleotide sequences for human FOLR1 are known in the art and are also provided herein as SEQ ID NO:1 and SEQ ID NO:2, respectively.

```
human folate receptor 1
                              SEQ ID NO: 1
MAQRMTTQLLLLLVWVAVVGEAQTRIAWARTELLNVCMNAKHHKE

KPGPEDKLHEQCRPWRKNACCSTNTSQEAHKDVSYLYRFNWNHCG

EMAPACKRHFIQDTCLYECSPNLGPWIQQVDQSWRKERVLNVPLC

KEDCEQWWEDCRTSYTCKSNWHKGWNWTSGFNKCAVGAACQPFEI

FYFPTPTVLCNEIWTHSYKVSNYSRGSGRCIQMWFDPAQGNPNEE

VARFYAAAMSGAGPWAAWPFLLSLALMLLWLLS human folate receptor 1 nucleic acid sequence
                              SEQ ID NO: 2
atggctcagcggatgacaacacagctgctgctccttctagtgtgg gtggctgtagtaggggaggctcagacaaggattgcatgggccagg actgagcttctcaatgtctgcatgaacgccaagcaccacaaggaa aagccaggccccgaggacaagttgcatgagcagtgtcgaccctgg aggaagaatgcctgctgttctaccaacaccagccaggaagcccat aaggatgtttcctacctatatagattcaactggaaccactgtgga gagatggcacctgcctgcaaacggcatttcatccaggacacctgc ctctacgagtgctcccccaacttggggccctggatccagcaggtg gatcagagctggcgcaaagagogggtactgaacgtgcccctgtgc aaagaggactgtgagcaatggtgggaagattgtcgcacctcctac acctgcaagagcaactggcacaagggctggaactggacttcaggg tttaacaagtgcgcagtgggagctgcctgccaacctttccatttc tacttccccacacccactgttctgtgcaatgaaatctggactcac tcctacaaggtcagcaactacagccagggagtggccgctgcatc cagatgtggttcgacccagcccagggcaaccccaatgaggaggtg gcgaggttctatgctgcagccatgagtggggctgggccctgggca gcctggccttcctgttagcctggccctaatgctgctgtggctg ctcagc
```

Anti-FOLR1 immunoconjugates contain a cell binding agent linked to a cytotoxin. The cell binding agents can be anti-FOLR1 antibodies or antigen-binding fragments thereof. Examples of therapeutically effective anti-FOLR1 antibodies can be found in US Appl. Pub. No. US 2012/0009181 which is herein incorporated by reference. An example of a therapeutically effective anti-FOLR1 antibody is huMov19 (M9346A) (comprising the sequences of SEQ ID NO:3 and SEQ ID NO:5). The polypeptides of SEQ ID NOs: 3-5 comprise the variable domain of the heavy chain of huMov19 (M9346A), the variable domain light chain version 1.00, and the variable domain light chain version 1.60 of huMov19, respectively. In certain embodiments, the huMov19 anti-FOLR1 antibody is comprised of a variable domain heavy chain represented by SEQ ID NO:3 and a variable domain light chain represented by SEQ ID NO:5 (version 1.60 of huMov19). In certain embodiments, the huMov19 (M9346A) antibody is encoded by the plasmids deposited with the American Type Culture Collection (ATCC), located at 10801 University Boulevard, Manassas, Va. 20110 on Apr. 7, 2010 under the terms of the Budapest Treaty and having ATCC deposit nos. PTA-10772 and PTA-10773 or 10774.

Amino acid sequences of huMov19 are provided in Tables 1-4 below:

TABLE 1

| | Variable heavy chain CDR amino acid sequences | | |
|---|---|---|---|
| Antibody | VH-CDR1 | VH-CDR2 | VH-CDR3 |
| huMov19 (M9346A) | Kabat Defined: GYFMN (SEQ ID NO: 9) | Kabat Defined: RIHPYDGDTFYNQKFQG (SEQ ID NO: 10) | Kabat Defined: YDGSRAMDY (SEQ ID NO: 12) |
| | AbM Defined: GYTFTGYFMN (SEQ ID NO: 19) | AbM Defined: RIHPYDGDTF (SEQ ID NO: 11) | AbM Defined: YDGSRAMDY (SEQ ID NO: 12) |
| muMOV19 | | Kabat Defined RIHPYDGDTFYNQNFKD (SEQ ID NO: 16) | |

TABLE 2

Variable light chain CDR amino acid sequences

| Antibody | VL-CDR1 | VL-CDR2 | VL-CDR3 |
|---|---|---|---|
| huMov19 (M9346A) | KASQSVSF AGTSLMH (SEQ ID NO: 6) | RASNLEA (SEQ ID NO: 7) | QQSREYP YT (SEQ ID NO: 8) |

TABLE 3

Anti-FOLR1 Variable chain amino acid sequences

| FOLR1 Antibody | Amino Acid Sequence |
|---|---|
| huMov19-VH | QVQLVQSGAEVVKPGASVKISCKASGYTFTGY FMNWVKQSPGQSLEWIGRIHPYDGDTFYNQKF QGKATLTVDKSSNTAHMELLSLTSEDFAVYYC TRYDGSRAMDYWGQGTTVTVSS (SEQ ID NO: 3) |
| huMov19-VL version 1.00 | DIVLTQSPLSLAVSLGQPAIISCKASQSVSFA GTSLMHWYHQKPGQQPRLLIYRASNLEAGVPD RFSGSGSKTDFTLNISPVEAEDAATYYCQQSR EYPYTFGGGTKLEIKR (SEQ ID NO: 4) |
| huMOV19-VL version 1.60 | DIVLTQSPLSLAVSLGQPAIISCKASQSVSFA GTSLMHWYHQKPGQQPRLLIYRASNLEAGVPD RFSGSGSKTDFTLTISPVEAEDAATYYCQQSR EYPYTFGGGTKLEIKR (SEQ ID NO: 5) |

TABLE 4

Full-length heavy and light chain amino acid sequences

| Antibody | Full-Length Amino Acid Sequence |
|---|---|
| huMov19-Heavy | QVQLVQSGAEVVKPGASVKISCKASGYTFTGYF MNWVKQSPGQSLEWIGRIHPYDGDTFYNQKFQG KATLTVDKSSNTAHMELLSLTSEDFAVYYCTRY DGSRAMDYWGQGTTVTVSSASTKGPSVFPLAPS SKSTSGGTAALGCLVKDYFPEPVTVSWNSGALT SGVHTFPAVLQSSGLYSLSSVVTVPSSSLGTQT YICNVNFIKPSNTKVDKKVEPKSCDKTHTCPPC PAPELLGGPSVFLFPPKPKDTLMISRTPEVTCV VVDVSHEDPEVKFNWYVDGVEVHNAKTKPREEQ YNSTYRVVSVLTVLHQDWLNGKEYKCKVSNKAL PAPIEKTISKAKGQPREPQVYTLPPSRDELTKN QVSLTCLVKGFYPSDIAVEWESNGQPENNYKTT PPVLDSDGSFFLYSKLTVDKSRWQQGNVFSCSV MHEALHNHYTQKSLSLSPGK (SEQ ID NO: 13) |
| huMov19-Light version 1.00 | DIVLTQSPLSLAVSLGQPAIISCKASQSVSFAG TSLMHWYHQKPGQQPRLLIYRASNLEAGVPDRF SGSGSKTDFTLNISPVEAEDAATYYCQQSREYP YTFGGGTKLEIKRTVAAPSVFIFPPSDEQLKSG TASVVCLLNNFYPREAKVQWKVDNALQSGNSQE SVTEQDSKDSTYSLSSTLTLSKADYEKHKVYAC EVTHQGLSSPVTKSFNRGEC (SEQ ID NO: 14) |
| huMOV19-Light version 1.60 | DIVLTQSPLSLAVSLGQPAIISCKASQSVSFAG TSLMHWYHQKPGQQPRLLIYRASNLEAGVPDRF SGSGSKTDFTLTISPVEAEDAATYYCQQSREYP YTFGGGTKLEIKRTVAAPSVFIFPPSDEQLKSG TASVVCLLNNFYPREAKVQWKVDNALQSGNSQE SVTEQDSKDSTYSLSSTLTLSKADYEKHKVYAC EVTHQGLSSPVTKSFNRGEC (SEQ ID NO: 15) |

In some embodiments, the anti-FOLR1 immunoconjugates comprise humanized antibodies or antigen-binding fragments thereof. In some embodiments, the humanized antibody or fragment is a resurfaced antibody or antigen-binding fragment thereof. In other embodiments, the anti-FOLR1 immunoconjugates comprises a fully human antibody or antigen-binding fragment thereof.

In certain embodiments, the anti-FOLR1 immunoconjugates have one or more of the following effects: inhibit proliferation of tumor cells, reduce the tumorigenicity of a tumor by reducing the frequency of cancer stem cells in the tumor, inhibit tumor growth, increase patient survival, trigger cell death of tumor cells, differentiate tumorigenic cells to a non-tumorigenic state, or prevent or reduce metastasis of tumor cells.

In certain embodiments, the anti-FOLR1 immunoconjugate comprises an antibody that has antibody-dependent cellular cytotoxicity (ADCC) activity.

In some embodiments, the anti-FOLR1 immunoconjugates are capable of reducing tumor volume. The ability of an anti-FOLR1 immunoconjugate to reduce tumor volume can be assessed, for example, by measuring a % T/C value, which is the median tumor volume of treated subjects divided by the median tumor volume of the control subjects. In certain embodiments, immunoconjugates or other agents that specifically bind human FOLR1 trigger cell death via a cytotoxic agent. For example, in certain embodiments, an antibody to a human FOLR1 antibody is conjugated to a maytansinoid that is activated in tumor cells expressing the FOLR1 by protein internalization. In certain embodiments, the anti-FOLR1 immunoconjugates are capable of inhibiting tumor growth. In certain embodiments, the anti-FOLR1 immunoconjugates are capable of inhibiting tumor growth in vivo (e.g., in a xenograft mouse model and/or in a human having cancer). In certain embodiments, the anti-FOLR1 immunoconjugates are capable of decreasing CA125 in ovarian cancer patients.

The FOLR1 binding molecules can be antibodies or antigen binding fragments that specifically bind to FOLR1 that comprise the CDRs of huMov19 (M9346A) with up to four (i.e. 0, 1, 2, 3, or 4) conservative amino acid substitutions per CDR, e.g., wherein the antibodies or fragments do not comprise the six CDRs of murine Mov19 (i.e., SEQ ID NOs:6-9, 16, and 12). Polypeptides can comprise one of the individual variable light chains or variable heavy chains described herein. Antibodies and polypeptides can also comprise both a variable light chain and a variable heavy chain.

In some embodiments, the FOLR1 binding molecule is an antibody or antigen-binding fragment comprising the sequences of SEQ ID NOs:6-10 and the sequence of SEQ ID NO:12. In some embodiments, the FOLR1 binding molecule is an antibody or antigen-binding fragment comprising the sequences of SEQ ID NOs:6-9 and the sequences of SEQ ID NOs:11 and 12 In some embodiments, the FOLR1 binding molecule is an antibody or antigen-binding fragment thereof comprising the sequences of SEQ ID NOs: 6-8, 19, 11, and 12.

Also provided are polypeptides that comprise a polypeptide having at least about 90% sequence identity to SEQ ID NO:3, SEQ ID NO:4 or SEQ ID NO:5. In certain embodiments, the polypeptide comprises a polypeptide having at least about 95%, at least about 96%, at least about 97%, at least about 98%, or at least about 99% sequence identity to SEQ ID NO:3, SEQ ID NO:4 or SEQ ID NO:5 Thus, in certain embodiments, the polypeptide comprises (a) a polypeptide having at least about 95% sequence identity to SEQ ID NO:3 and/or (b) a polypeptide having at least about 95% sequence identity to SEQ ID NO:4 or SEQ ID NO:5. In certain embodiments, the polypeptide comprises (a) a polypeptide having the amino acid sequence of SEQ ID NO:3; and/or (b) a polypeptide having the amino acid sequence of SEQ ID NO:4 or SEQ ID NO:5. In certain embodiments, the polypeptide is an antibody and/or the polypeptide specifically binds FOLR1. In certain embodiments, the polypeptide is a murine, chimeric, or humanized antibody that specifically binds FOLR1. In certain embodiments, the polypeptide having a certain percentage of sequence identity to SEQ ID NO:3, SEQ ID NO:4 or SEQ ID NO:5 differs from SEQ ID NO:3, SEQ ID NO:4 or SEQ ID NO:5 by conservative amino acid substitutions only.

Polypeptides can comprise one of the individual light chains or heavy chains described herein. Antibodies and polypeptides can also comprise both a light chain and a heavy chain.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against the human FOLR1 is a humanized antibody. In some embodiments, the humanized antibody is a resurfaced antibody. In certain embodiments, such antibodies are used therapeutically to reduce antigenicity and HAMA (human anti-mouse antibody) responses when administered to a human subject. Humanized antibodies can be produced using various techniques known in the art. In certain alternative embodiments, the antibody to FOLR1 is a human antibody.

Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety). Affinity maturation strategies and chain shuffling strategies (Marks et al., 1992, Bio/Technology 10:779-783, incorporated by reference in its entirety) are known in the art and can be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

The polypeptides of the present invention can be recombinant polypeptides, natural polypeptides, or synthetic polypeptides comprising an antibody, or fragment thereof, against a human FOLR1.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, Pa. (2000).

Methods known in the art for purifying antibodies and other proteins also include, for example, those described in U.S. Patent Publication No. 2008/0312425, 2008/0177048, and 2009/0187005, each of which is hereby incorporated by reference herein in its entirety.

Suitable drugs or prodrugs are known in the art. The drugs or prodrugs can be cytotoxic agents. The cytotoxic agent used in the cytotoxic conjugate of the present invention can be any compound that results in the death of a cell, or induces cell death, or in some manner decreases cell viability, and includes, for example, maytansinoids and maytansinoid analogs.

Such conjugates can be prepared by using a linking group in order to link a drug or prodrug to the antibody or functional equivalent. Suitable linking groups are well known in the art and include, for example, disulfide groups, thioether groups, acid labile groups, photolabile groups, peptidase labile groups and esterase labile groups.

The drug or prodrug can, for example, be linked to the anti-FOLR1 antibody or fragment thereof through a disulfide bond. The linker molecule or crosslinking agent comprises a reactive chemical group that can react with the anti-FOLR1 antibody or fragment thereof. The reactive chemical groups for reaction with the cell-binding agent can be N-succinimidyl esters and N-sulfosuccinimidyl esters. Additionally the linker molecule comprises a reactive chemical group, which can be a dithiopyridyl group that can react with the drug to form a disulfide bond. Linker molecules include, for example, N-succinimidyl 3-(2-pyridyldithio) propionate (SPDP) (see, e.g., Carlsson et al., *Biochem*. 1, 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)2-sulfobutanoate (sulfo-SPDB) (see US Publication No. 20090274713), N-succinimidyl 4-(2-pyridyldithio) pentanoate (SPP) (see, e.g., CAS Registry number 341498-08-6), 2-iminothiolane, or acetylsuccinic anhydride. For example, the antibody or cell binding agent can be modified with crosslinking reagents and the antibody or cell binding agent containing free or protected thiol groups thus derived is then reacted with a disulfide- or thiol-containing maytansinoid to produce conjugates. The conjugates can be purified by chromatography, including but not limited to HPLC, size-exclusion, adsorption, ion exchange and affinity capture, dialysis or tangential flow filtration.

In another aspect of the present invention, the anti-FOLR1 antibody is linked to cytotoxic drugs via disulfide bonds and a polyethylene glycol spacer in enhancing the potency, solubility or the efficacy of the immunoconjugate. Such cleavable hydrophilic linkers are described in WO2009/0134976. The additional benefit of this linker design is the desired high monomer ratio and the minimal aggregation of the antibody-drug conjugate. Specifically contemplated in this aspect are conjugates of cell-binding agents and drugs linked via disulfide group (—S—S—) bearing polyethylene glycol spacers ($(CH_2CH_2O)_{n=1-14}$) with a narrow range of drug load of 2-8 are described that show relatively high potent biological activity toward cancer cells and have the desired biochemical properties of high conjugation yield and high monomer ratio with minimal protein aggregation.

Antibody-maytansinoid conjugates with non-cleavable linkers can also be prepared. Such crosslinkers are described in the art (see US Publication No. 20050169933) and include but are not limited to, N-succinimidyl 4-(maleimidomethyl) cyclohexanecarboxylate (SMCC). In some embodiments, the antibody is modified with crosslinking reagents such as succinimidyl 4-(N-maleimidomethyl)-cyclohexane-1-carboxylate (SMCC), sulfo-SMCC, maleimidobenzoyl-N-hydroxysuccinimide ester (MBS), sulfo-MBS or succinimidyl-iodoacetate, as described in the literature, to introduce 1-10 reactive groups (Yoshitake et al, Eur. J. Biochem., 101:395-399 (1979); Hashida et al, J. Applied Biochem., 56-63 (1984); and Liu et al, Biochem., 18:690-697 (1979)). The modified antibody is then reacted with the thiol-containing maytansinoid derivative to produce a conjugate. The conjugate can be purified by gel filtration through a Sephadex G25 column or by dialysis or tangential flow filtration. The modified antibodies are treated with the thiol-containing maytansinoid (1 to 2 molar equivalent/maleimido group) and antibody-maytansinoid conjugates are purified by gel filtration through a Sephadex G-25 column, chromatography on a ceramic hydroxyapatite column, dialysis or tangential flow filtration or a combination of methods thereof. Typically, an average of 1-10 maytansinoids per antibody are linked. One method is to modify antibodies with succinimidyl 4-(N-maleimidomethyl)-cyclohexane-1-carboxylate (SMCC) to introduce maleimido groups followed by reaction of the modified antibody with a thiol-containing maytansinoid to give a thioether-linked conjugate. Again conjugates with 1 to 10 drug molecules per antibody molecule result. Maytansinoid conjugates of antibodies, antibody fragments, and other proteins are made in the same way.

In another aspect of the invention, the FOLR1 antibody is linked to the drug via a non-cleavable bond through the intermediacy of a PEG spacer. Suitable crosslinking reagents comprising hydrophilic PEG chains that form linkers between a drug and the anti-FOLR1 antibody or fragment are also well known in the art, or are commercially available (for example from Quanta Biodesign, Powell, Ohio). Suitable PEG-containing crosslinkers can also be synthesized from commercially available PEGs themselves using standard synthetic chemistry techniques known to one skilled in the art. The drugs can be reacted with bifunctional PEG-containing cross linkers to give compounds of the following formula, $Z-X_1-(-CH_2-CH_2-O-)_n-Y_p-D$, by methods described in detail in US Patent Publication 20090274713 and in WO2009/0134976, which can then react with the cell binding agent to provide a conjugate. Alternatively, the cell binding can be modified with the bifunctional PEG crosslinker to introduce a thiol-reactive group (such as a maleimide or haloacetamide) which can then be treated with a thiol-containing maytansinoid to provide a conjugate. In another method, the cell binding can be modified with the bifunctional PEG crosslinker to introduce a thiol moiety which can then be treated with a thiol-reactive maytansinoid (such as a maytansinoid bearing a maleimide or haloacetamide), to provide a conjugate.

Examples of suitable PEG-containing linkers include linkers having an N-succinimidyl ester or N-sulfosuccinimidyl ester moiety for reaction with the anti-FOLR1 antibody or fragment thereof, as well as a maleimido- or haloacetyl-based moiety for reaction with the compound. A PEG spacer can be incorporated into any crosslinker known in the art by the methods described herein.

In some embodiments, the linker is a linker containing at least one charged group as described, for example, in U.S. Patent Publication No. 2012/0282282, the contents of which are entirely incorporated herein by reference. In some embodiments, the charged or pro-charged crosslinkers are those containing sulfonate, phosphate, carboxyl or quaternary amine substituents that significantly increase the solubility of the modified cell-binding agent and the cell-binding agent-drug conjugates, especially for monoclonal antibody-drug conjugates with 2 to 20 drugs/antibody linked. Conjugates prepared from linkers containing a pro-charged moiety would produce one or more charged moieties after the conjugate is metabolized in a cell. In some embodiments, the linker is selected from the group consisting of: N-succinimidyl 4-(2-pyridyldithio)-2-sulfopentanoate (sulfo-SPP) and N-succinimidyl 4-(2-pyridyldithio)-2-sulfobutanoate (sulfo-SPDB).

Many of the linkers disclosed herein are described in detail in U.S. Patent Publication Nos. 2005/0169933, 2009/0274713, and 2012/0282282, and in WO2009/0134976; the contents of which are entirely incorporated herein by reference.

The present invention includes aspects wherein about 2 to about 8 drug molecules ("drug load"), for example, maytansinoid, are linked to an anti-FOLR1 antibody or fragment thereof "Drug load", as used herein, refers to the number of drug molecules (e.g., a maytansinoid) that can be attached to a cell binding agent (e.g., an anti-FOLR1 antibody or fragment thereof). In one aspect, the number of drug molecules that can be attached to a cell binding agent can average from about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1). N2'-deacetyl-N2'-(3-mercapto-1-oxopropyl)-maytansine (DM1) and N2'-de acetyl-N2'-(4-mercapto-4-methyl-1-oxopentyl) maytansine (DM4) can be used.

Thus, in one aspect, an immunoconjugate comprises 1 maytansinoid per antibody. In another aspect, an immunoconjugate comprises 2 maytansinoids per antibody. In another aspect, an immunoconjugate comprises 3 maytansinoids per antibody. In another aspect, an immunoconjugate comprises 4 maytansinoids per antibody. In another aspect, an immunoconjugate comprises 5 maytansinoids per antibody. In another aspect, an immunoconjugate comprises 6 maytansinoids per antibody. In another aspect, an immunoconjugate comprises 7 maytansinoids per antibody. In another aspect, an immunoconjugate comprises 8 maytansinoids per antibody.

In one aspect, an immunoconjugate (e.g., an immunoconjugate comprising the linker SPDB and the maytansinoid DM4) comprises about 1 to about 8 maytansinoids per antibody. In another aspect, an immunoconjugate (e.g., an immunoconjugate comprising the linker SPDB and the maytansinoid DM4) comprises about 2 to about 7 maytansinoids per antibody. In another aspect, an immunoconjugate (e.g., an immunoconjugate comprising the linker SPDB and the maytansinoid DM4) comprises about 2 to about 6 maytansinoids per antibody. In another aspect, an immunoconjugate (e.g., an immunoconjugate comprising the linker SPDB and the maytansinoid DM4) comprises about 2 to about 5 maytansinoids per antibody. In another aspect, an immunoconjugate (e.g., an immunoconjugate comprising the linker SPDB and the maytansinoid DM4) comprises about 3 to about 5 maytansinoids per antibody. In another aspect, an immunoconjugate (e.g., an immunoconjugate comprising the linker SPDB and the maytansinoid DM4) comprises about 3 to about 4 maytansinoids per antibody.

In one aspect, a composition comprising immunoconjugates has an average of about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1) drug molecules (e.g., maytansinoids) attached per antibody. In one aspect, a composition comprising immunoconjugates has an average of about 1 to about 8 drug molecules (e.g., maytansinoids) per antibody. In one aspect, a composition comprising immunoconjugates has an average of about 2 to about 7 drug molecules (e.g., maytansinoids) per antibody. In one aspect, a composition comprising immunoconjugates has an average of about 2 to about 6 drug molecules (e.g., maytansinoids) per antibody. In one aspect, a composition comprising immunoconjugates has an average of about 2 to about 5 drug molecules (e.g., maytansinoids) per antibody. In one aspect, a composition comprising immunoconjugates has an average of about 3 to about 5 drug molecules (e.g., maytansinoids) per antibody. In one aspect, a composition comprising immunoconjugates has an average of about 3 to about 4 drug molecules (e.g., maytansinoids) per antibody.

In one aspect, a composition comprising immunoconjugates has an average of about $2\pm0.5$, about $3\pm0.5$, about $4\pm0.5$, about $5\pm0.5$, about $6\pm0.5$, about $7\pm0.5$, or about $8\pm0.5$ drug molecules (e.g., maytansinoids) attached per antibody. In one aspect, a composition comprising immunoconjugates has an average of about $3.5\pm0.5$ drug molecules (e.g., maytansinoids) per antibody.

The anti-FOLR1 antibody or fragment thereof can be modified by reacting a bifunctional crosslinking reagent with the anti-FOLR1 antibody or fragment thereof, thereby resulting in the covalent attachment of a linker molecule to the anti-FOLR1 antibody or fragment thereof. As used herein, a "bifunctional crosslinking reagent" is any chemical moiety that covalently links a cell-binding agent to a drug, such as the drugs described herein. In another method, a portion of the linking moiety is provided by the drug. In this respect, the drug comprises a linking moiety that is part of a larger linker molecule that is used to join the cell-binding agent to the drug. For example, to form the maytansinoid DM1, the side chain at the C-3 hydroxyl group of maytansine is modified to have a free sulfhydryl group (SH). This thiolated form of maytansine can react with a modified cell-binding agent to form a conjugate. Therefore, the final linker is assembled from two components, one of which is provided by the crosslinking reagent, while the other is provided by the side chain from DM1.

The drug molecules can also be linked to the antibody molecules through an intermediary carrier molecule such as serum albumin.

As used herein, the expression "linked to a cell-binding agent" or "linked to an anti-FOLR1 antibody or fragment" refers to the conjugate molecule comprising at least one drug derivative bound to a cell-binding agent, anti-FOLR1 antibody, or fragment via a suitable linking group, or a precursor thereof. Exemplary linking groups are SPDB or sulfo-SPDB.

In certain embodiments, cytotoxic agents useful in the present invention are maytansinoids and maytansinoid analogs. Examples of suitable maytansinoids include esters of maytansinol and maytansinol analogs. Included are any drugs that inhibit microtubule formation and that are highly toxic to mammalian cells, as are maytansinol and maytansinol analogs.

Examples of suitable maytansinol esters include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 5,208,020; 5,416,064; 5,475,092; 5,585,499; 5,846,545; 6,333,410; 7,276,497 and 7,473,796.

In a certain embodiment, the immunoconjugates of the invention utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula (I):

(I)

[Structural formula (I)]

In another embodiment, the conjugates of the present invention utilize the thiol-containing maytansinoid $N^{2'}$-deacetyl-$N^{2'}$(4-methyl-4-mercapto-1-oxopentyl)-maytansine (e.g., DM4) as the cytotoxic agent. DM4 is represented by the following structural formula (II):

(II)

[Structural formula (II)]

Another maytansinoid comprising a side chain that contains a sterically hindered thiol bond is $N^{2'}$-deacetyl-$N^{2'}$(4-mercapto-1-oxopentyl)-maytansine (termed DM3), represented by the following structural formula (III):

(III)

[Structural formula (III)]

Each of the maytansinoids taught in U.S. Pat. Nos. 5,208,020 and 7,276,497, can also be used in the conjugate of the present invention. In this regard, the entire disclosure of U.S. Pat. Nos. 5,208,020 and 7,276,697 is incorporated herein by reference.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. In some embodiments, the C-3 position serves as the position to chemically link the linking moiety, and in some particular embodiments, the C-3 position of maytansinol serves as the position to chemically link the linking moiety.

Structural representations of some conjugates are shown below:

(IV)

[Structural formula (IV)]

Ab= Antibody

Ab-SPDB-DM4

-continued
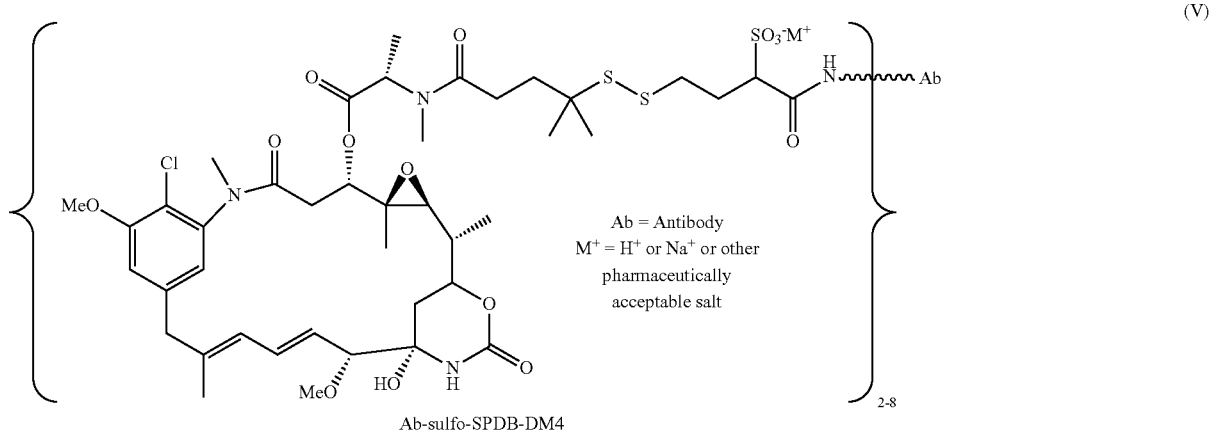
Ab-sulfo-SPDB-DM4
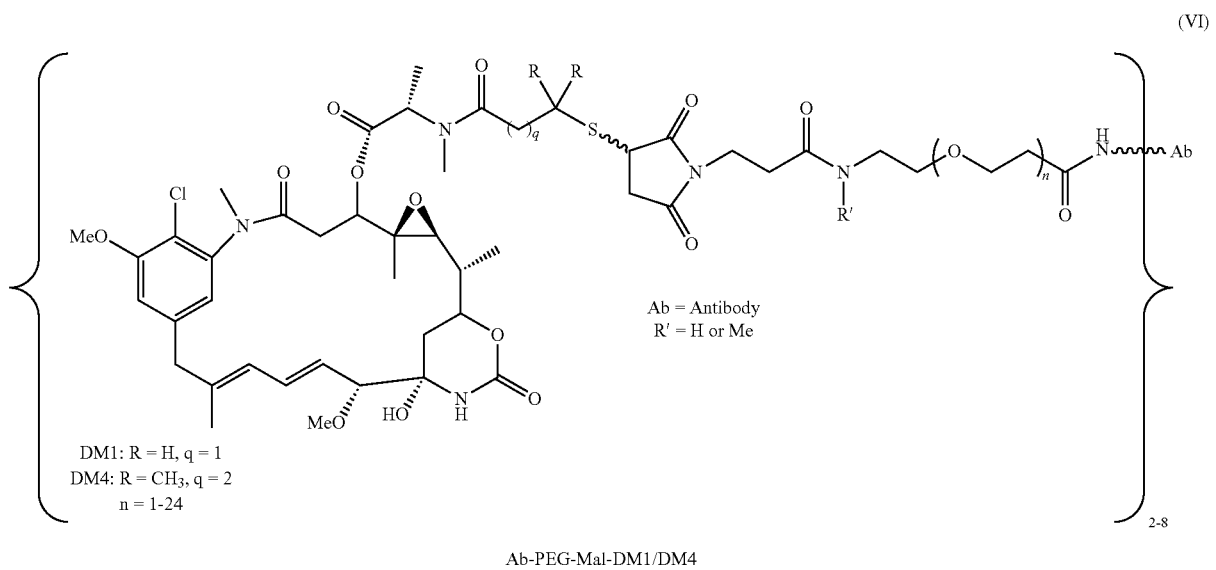
DM1: R = H, q = 1
DM4: R = CH₃, q = 2
n = 1-24
Ab-PEG-Mal-DM1/DM4
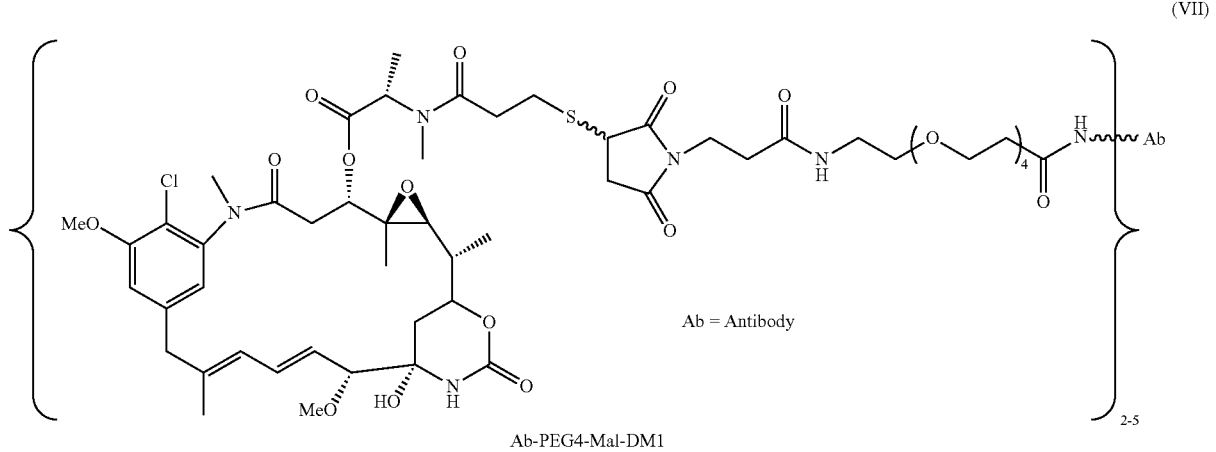
Ab-PEG4-Mal-DM1

-continued
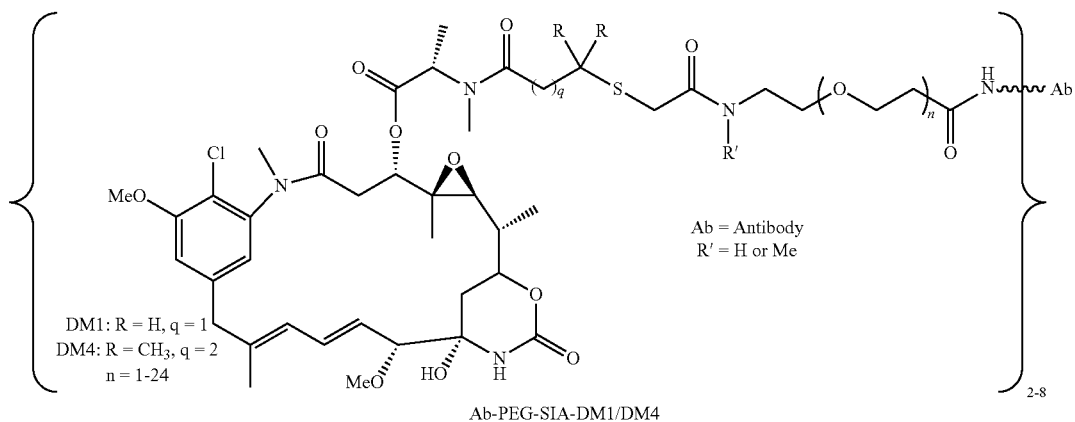
Ab-PEG-SIA-DM1/DM4 (VIII)
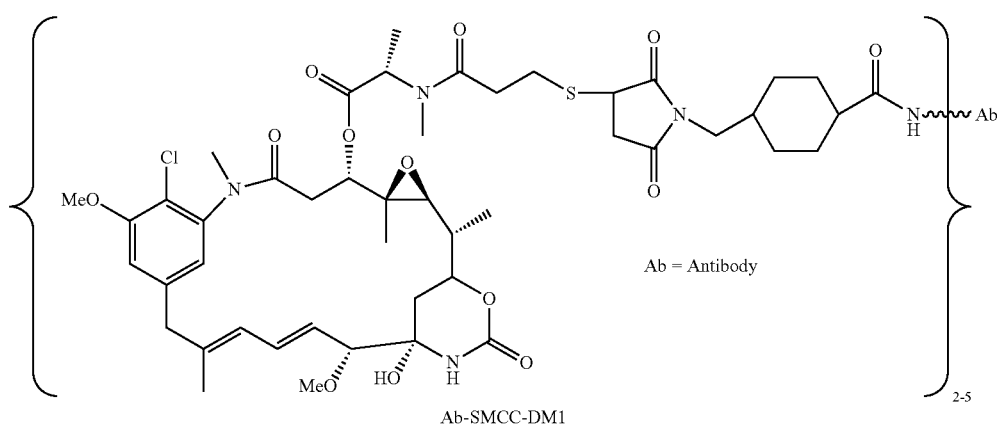
Ab-SMCC-DM1 (IX)
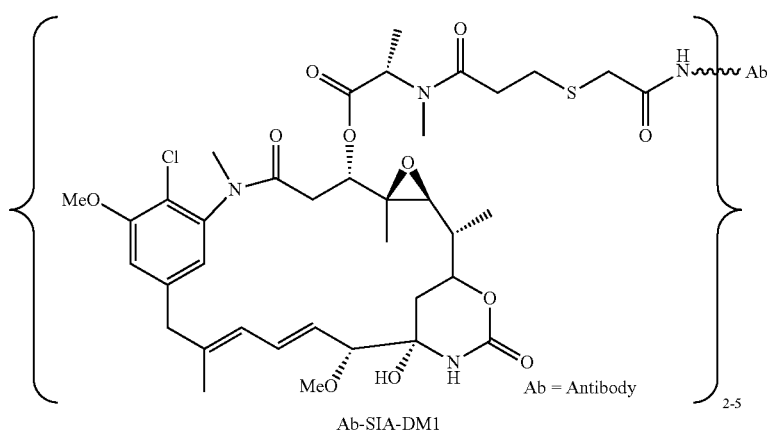
Ab-SIA-DM1 (X)

(XI)

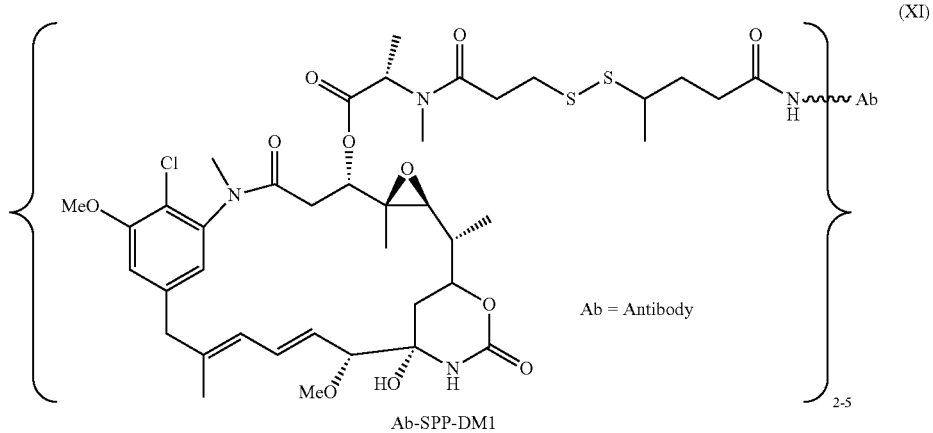

Ab-SPP-DM1

Ab = Antibody

Also included in the present invention are any stereoisomers and mixtures thereof for any compounds or conjugates depicted by any structures above.

Several descriptions for producing such antibody-maytansinoid conjugates are provided in U.S. Pat. Nos. 6,333,410, 6,441,163, 6,716,821, and 7,368,565, each of which is incorporated herein in its entirety.

In general, a solution of an antibody in aqueous buffer can be incubated with a molar excess of maytansinoids having a disulfide moiety that bears a reactive group. The reaction mixture can be quenched by addition of excess amine (such as ethanolamine, taurine, etc.). The maytansinoid-antibody conjugate can then be purified by gel filtration.

The number of maytansinoid molecules bound per antibody molecule can be determined by measuring spectrophotometrically the ratio of the absorbance at 252 nm and 280 nm. The average number of maytansinoid molecules/antibody can be, for example, 1-10 or 2-5. The average number of maytansinoid molecules/antibody can be, for example about 3 to about 4. The average number of maytansinoid molecules/antibody can be about 3.5.

Conjugates of antibodies with maytansinoid or other drugs can be evaluated for their ability to suppress proliferation of various unwanted cell lines in vitro. For example, cell lines such as the human lymphoma cell line Daudi and the human lymphoma cell line Ramos, can easily be used for the assessment of cytotoxicity of these compounds. Cells to be evaluated can be exposed to the compounds for 4 to 5 days and the surviving fractions of cells measured in direct assays by known methods. $IC_{50}$ values can then be calculated from the results of the assays.

The immunoconjugates can, according to some embodiments described herein, be internalized into cells. The immunoconjugate, therefore, can exert a therapeutic effect when it is taken up by, or internalized, by an FOLR1-expressing cell. In some particular embodiments, the immunoconjugate comprises an antibody, antibody fragment, or polypeptide, linked to a cytotoxic agent by a cleavable linker, and the cytotoxic agent is cleaved from the antibody, antibody fragment, or polypeptide, wherein it is internalized by an FOLR1-expressing cell.

In some embodiments, the immunoconjugates are capable of reducing tumor volume. For example, in some embodiments, treatment with an immunoconjugate results in a % T/C value that is less than about 50%, less than about 45%, less than about 40%, less than about 35%, less than about 30%, less than about 25%, less than about 20%, less than about 15%, less than about 10%, or less than about 5%. In some particular embodiments, the immunoconjugates can reduce tumor size in a KB, OVCAR-3, IGROV-1, and/or OV-90 xenograft model. In some embodiments, the immunoconjugates are capable of inhibiting metastases.

III. Anti-VEGF Agents

Described herein are methods of administering anti-FOLR1 immunoconjugates such as IMGN853 in combination with agents that specifically bind VEGF (e.g., Bevacizumab) or a VEGF receptor. Anti-VEGF agents include, for example, anti-VEGF or anti-VEGFR antibodies (e.g., Bevacizumab), Tyrosine Kinase Inhibitors (TKIs) (e.g., Cediranib), and soluble VEGF receptors (e.g., VEGF-Trap). Anti-VEGF agents are known in the art, and certain examples are provided in Meadows and Hurwitz, *Cold Spring Harbor Perspectives in Medicine* 2:a006577 (2012), which is herein incorporated by reference in its entirety.

In certain embodiments, the anti-VEGF agents are capable of inhibiting tumor growth. In certain embodiments, the anti-VEGF agents are capable of inhibiting tumor growth in vivo (e.g., in a xenograft mouse model and/or in a human having cancer). In certain embodiments, the anti-VEGF agents are capable of inhibiting angiogenesis.

In certain embodiments, the anti-VEGF agents are anti-VEGF or anti-VEGFR antibodies or antigen-binding fragments thereof.

A full-length amino acid sequences for human VEGF-A is provided at UniProtKB Accession No. P15692 and herein as SEQ ID NO:17:

(SEQ ID NO: 17)
MNFLLSWVHWSLALLLYLHHAKWSQAAPMAEGGGQNFIHEVVKFMDVYQ

RSYCHPIETLVDIFQEYPDEIEYIFKPSCVPLMRCGGCCNDEGLECVPT

EESNITMQIMRIKPHQGQHIGEMSFLQHNKCECRPKKDRARQEKKSVRG

KGKGQKRKRKKSRYKSWSVYVGARCCLMPWSLPGPHPCGPCSERRKHLF

VQDPQTCKCSCKNTDSRCKARQLELNERTCRCDKPRR, the signal sequence of which is
(SEQ ID NO: 18)
MNFLLSWVHWSLALLLYLHHAKWSQA.

Thus, in some embodiments, an anti-VEGF antibody or antigen-binding fragment thereof binds to an epitope in SEQ ID NO:17 or to an epitope in the mature version of SEQ ID NO:17 (i.e., SEQ ID NO:17 lacking the signal sequence.)

Anti-VEGF antibodies and antigen-binding fragments thereof can comprise polypeptides comprising the variable light chains or variable heavy chains described herein. Anti-VEGF antibodies and polypeptides can also comprise both a variable light chain and a variable heavy chain. Anti-VEGF antibodies, and the variable light chains and variable heavy chains thereof, are described in at least U.S. Pat. No. 6,884,879; U.S. Pat. No. 6,054,297; U.S. Pat. No. 7,169,901; U.S. Pat. No. 7,365,166; U.S. Pat. No. 7,060,269; U.S. Pat. No. 7,622,115; U.S. Pat. No. 8,778,340; and U.S. Pat. No. 7,297,334, all of which are incorporated herein by reference in its entirety.

In some embodiments, an anti-VEGF antibody is bevacizuamb, ABP 215 (Amgen), BCD-021 (Biocad), or ranibizumab. In some embodiments, an anti-VEGF antibody is bevacizuamb, ABP 215 (Amgen) or BCD-021 (Biocad). In some embodiments, an anti-VEGF antibody is bevacizuamb.

In some embodiments, an anti-VEGF receptor antibody or antigen-binding fragment thereof binds to VEGFR1, VEGFR2, or VEGFR3. In some embodiments, an anti-VEGF receptor antibody or antigen-binding fragment thereof binds to VEGFR2. In some embodiments, an anti-VEGF receptor antibody is ramucirumab.

In certain embodiments, the anti-VEGF agents are tyrosine kinase inhibitors. The tyrosine kinase inhibitor can inhibit, e.g., VEGFR1, VEGFR2, and/or VEGFR3. In some embodiments, the tyrosine kinase inhibitor is cediranib. In some embodiments, the tyrosine kinase inhibitor is pazopanib. In some embodiments, the tyrosine kinase inhibitor is axitinib. In some embodiments, the tyrosine kinase inhibitor is vatalanib. In some embodiments, the tyrosine kinase inhibitor is semaxanib. In some embodiments, the tyrosine kinase inhibitor is sunitinib. In some embodiments, the tyrosine kinase inhibitor is sorafenib. In some embodiments, the tyrosine kinase inhibitor is ramucirumab. In some embodiments, the tyrosine kinase inhibitor is aflibercept.

In certain embodiments, the anti-VEGF agents are soluble VEGF receptor proteins. Soluble VEGF receptor proteins can include the extracellular ligand-binding domain of VEGFR1. Soluble VEGF receptor proteins can include the extracellular ligand-binding domain of VEGFR2. Soluble VEGF receptor proteins can include the extracellular ligand-binding domain of VEGFR1 and VEGFR2. In some embodiments, the soluble VEGF receptor is VEGF-Trap (Aflibercept), a fusion protein combining the Fc portion of human IgG$_1$ with the principal extracellular ligand-binding domains of human VEGFR1 and VEGFR2.

IV. Platinum-Based Agents

Described herein are methods of administering anti-FOLR1 immunoconjugates such as IMGN853 in combination with platinum based agents, e.g., cisplatin, carboplatin, or oxaliplatin.

Cisplatin is a platinum-based, alkylating chemotherapy agent that produces DNA adducts and, therefore, is cytotoxic to cells deficient in excision repair (see Huang et al., *PNAS* 91:10394-10398 (1994)). Cisplatin is the parent compound of carboplatin. Like cisplatin, carboplatin produces DNA adducts that are cytotoxic to a cell deficient in excision repair. Exemplary cisplatins include Platinol and Platinol-AQ.

Carboplatin is considered a therapeutic equivalent to cisplatin (showing efficacy in the same and additional tissues as compared to cisplatin) but with a much different (better) toxicity profile (Lokich et al., *Annals. Of Oncology* 9:13-21 (1998)). Exemplary carboplatins include paraplatin.

Oxaliplatin is a third-generation platinum drug. Exemplary oxaplatins include Eloxatin®.

Administration of a platinum-based agent in combination with an anti-FOLR1 immunoconjugate (e.g., IMGN853) can reduce the amount and/or frequency of platinum-based agent required to achieve the same efficacy, thereby reducing the toxicity of the therapy. Administration of platinum-based agent in combination with an anti-FOLR1 immunoconjugate (e.g., IMGN853) can also increase the efficacy of the therapy.

In some embodiments, the platinum-based agent is cisplatin, carboplatin, or oxaliplatin. In some embodiments, the platinum-based agent is cispatin or carboplatin. In some embodiments, the platinum-based agent is cisplatin. In some embodiments, the platinum-based agent is carboplatin.

V. Doxorubicin

Described herein are methods of administering anti-FOLR1 immunoconjugates such as IMGN853 in combination with doxorubicin.

Doxorubicin is an anthracycline antibiotic chemotherapy agent that binds DNA-associated enzymes such as topoisomerases and can intercalate the base pairs of DNA, thereby producing a range of cytotoxic effects and eventual apoptosis of a cell (Tacar et al., *J. of Pharmacy & Pharmacology*, 65: 157-170 (2013)).

In some embodiments, doxorubicin is pegylated. In some embodiments, doxorubicin is not peglylated.

In some embodiments, doxorubicin is liposomal. In some embodiments, doxorubicin is not liposomal.

In some embodiments, doxorubicin is pegylated, liposomal doxorubicin.

Exemplary doxorubicins include MYOCET® (Cephalon UK, Ltd.)), DOX-NP (Avanti Polar Lipids, Inc.), CAELYX® (Janssen), and DOXIL® (Liposom Technology, Inc.).

Administration of doxorubicin in combination with an anti-FOLR1 immunoconjugate (e.g., IMGN853) can reduce the amount and/or frequency of doxorubicin required to achieve the same efficacy, thereby reducing the toxicity of the therapy. Administration of doxorubicin in combination with an anti-FOLR1 immunoconjugate (e.g., IMGN853) can also increase the efficacy of the therapy.

VI. Pharmaceutical Compositions and Kits

As provided herein, anti-FOLR1 immunoconjugates (e.g., IMGN853) can be used in combination with anti-VEGF agents (e.g., bevacizumab), a platinum-based agent, and/or doxorubicin to treat cancer.

In some embodiments, an anti-FOLR1 immunoconjugate (e.g., IMGN853) and an anti-VEGF agent (e.g., bevacizumab) are contained within the same pharmaceutical composition. In some embodiments, an anti-FOLR1 immunoconjugate (e.g., IMGN853) and an anti-VEGF agent (e.g., bevacizumab) are contained within two separate pharmaceutical compositions within a single kit. In other embodiments, a kit comprises an anti-FOLR1 immunoconjugate (e.g., IMGN853) and instructions to administer the anti-FOLR1 immunoconjugate (e.g., IMGN853) and an anti-VEGF agent (e.g., bevacizumab). In other embodiments, a kit comprises an anti-VEGF agent (e.g., bevacizumab) and instructions to administer the anti-VEGF agent (e.g., bevacizumab) and an anti-FOLR1 immunoconjugate (e.g., IMGN853).

In some embodiments, an anti-FOLR1 immunoconjugate (e.g., IMGN853) and a platinum-based agent are contained within the same pharmaceutical composition. In some embodiments, an anti-FOLR1 immunoconjugate (e.g., IMGN853) and a platinum-based agent are contained within two separate pharmaceutical compositions within a single kit. In other embodiments, a kit comprises an anti-FOLR1 immunoconjugate (e.g., IMGN853) and instructions to administer the anti-FOLR1 immunoconjugate (e.g., IMGN853) and a platinum-based agent. In other embodiments, a kit comprises a platinum-based agent and instructions to administer the platinum-based agent and an anti-FOLR1 immunoconjugate (e.g., IMGN853).

In some embodiments, an anti-FOLR1 immunoconjugate (e.g., IMGN853) and doxorubicin are contained within the same pharmaceutical composition. In some embodiments, an anti-FOLR1 immunoconjugate (e.g., IMGN853) and doxorubicin are contained within two separate pharmaceutical compositions within a single kit. In other embodiments, a kit comprises an anti-FOLR1 immunoconjugate (e.g., IMGN853) and instructions to administer the anti-FOLR1 immunoconjugate (e.g., IMGN853) and doxorubicin. In other embodiments, a kit comprises doxorubicin and instructions to administer the platinum-based agent and an anti-FOLR1 immunoconjugate (e.g., IMGN853).

In some embodiments, an anti-FOLR1 immunoconjugate (e.g., IMGN853), an anti-VEGF agent (e.g., bevacizumab), and a platinum-based agent are contained within the same pharmaceutical composition. In some embodiments, an anti-FOLR1 immunoconjugate (e.g., IMGN853), an anti-VEGF agent (e.g., bevacizumab), and a platinum-based agent are contained within two or three separate pharmaceutical compositions within a single kit.

In other embodiments, a kit comprises an anti-FOLR1 immunoconjugate (e.g., IMGN853) and instructions to administer the anti-FOLR1 immunoconjugate (e.g., IMGN853), an anti-VEGF agent (e.g., bevacizumab), and a platinum-based agent. In other embodiments, a kit comprises an anti-VEGF agent (e.g., bevacizumab) and instructions to administer the anti-VEGF agent (e.g., bevacizumab), an anti-FOLR1 immunoconjugate (e.g., IMGN853), and a platinum-based agent. In other embodiments, a kit comprises a platinum-based agent and instructions to administer the platinum-based agent, an anti-VEGF agent (e.g., bevacizumab), and an anti-FOLR1 immunoconjugate (e.g., IMGN853).

In other embodiments, a kit comprises an anti-FOLR1 immunoconjugate (e.g., IMGN853) and an anti-VEGF agent (e.g., bevacizumab) and instructions to administer the anti-FOLR1 immunoconjugate (e.g., IMGN853), the anti-VEGF agent (e.g., bevacizumab), and a platinum-based agent. In other embodiments, a kit comprises an anti-FOLR1 immunoconjugate (e.g., IMGN853) and a platinum-based agent and instructions to administer the anti-FOLR1 immunoconjugate (e.g., IMGN853), the platinum-based agent, and an anti-VEGF agent (e.g., bevacizumab). In other embodiments, a kit comprises an anti-VEGF agent (e.g., bevacizumab) and a platinum-based agent and instructions to administer the anti-VEGF agent (e.g., bevacizumab), the platinum-based agent, and an anti-FOLR1 immunoconjugate (e.g., IMGN853).

In other embodiments, a kit comprises an anti-FOLR1 immunoconjugate (e.g., IMGN853) and instructions to administer the anti-FOLR1 immunoconjugate (e.g., IMGN853), an anti-VEGF agent (e.g., bevacizumab), and doxorubicin. In other embodiments, a kit comprises an anti-VEGF agent (e.g., bevacizumab) and instructions to administer the anti-VEGF agent (e.g., bevacizumab), an anti-FOLR1 immunoconjugate (e.g., IMGN853), and doxorubicin. In other embodiments, a kit comprises doxorubicin and instructions to administer the doxorubicin, an anti-VEGF agent (e.g., bevacizumab), and an anti-FOLR1 immunoconjugate (e.g., IMGN853).

In other embodiments, a kit comprises an anti-FOLR1 immunoconjugate (e.g., IMGN853) and an anti-VEGF agent (e.g., bevacizumab) and instructions to administer the anti-FOLR1 immunoconjugate (e.g., IMGN853), the anti-VEGF agent (e.g., bevacizumab), and doxorubicin. In other embodiments, a kit comprises an anti-FOLR1 immunoconjugate (e.g., IMGN853) and doxorubicin and instructions to administer the anti-FOLR1 immunoconjugate (e.g., IMGN853), the doxorubicin, and an anti-VEGF agent (e.g., bevacizumab). In other embodiments, a kit comprises an anti-VEGF agent (e.g., bevacizumab) and doxorubicin and instructions to administer the anti-VEGF agent (e.g., bevacizumab), the doxorubicin, and an anti-FOLR1 immunoconjugate (e.g., IMGN853).

In other embodiments, a kit comprises an anti-FOLR1 immunoconjugate (e.g., IMGN853) and instructions to administer the anti-FOLR1 immunoconjugate (e.g., IMGN853), a platinum-based agent, and doxorubicin. In other embodiments, a kit comprises a platinum-based agent and instructions to administer the platinum-based agent, an anti-FOLR1 immunoconjugate (e.g., IMGN853), and doxorubicin. In other embodiments, a kit comprises doxorubicin and instructions to administer the doxorubicin, the platinum-based agent, and an anti-FOLR1 immunoconjugate (e.g., IMGN853).

In other embodiments, a kit comprises an anti-FOLR1 immunoconjugate (e.g., IMGN853) and a platinum-based agent and instructions to administer the anti-FOLR1 immunoconjugate (e.g., IMGN853), the platinum-based agent, and doxorubicin. In other embodiments, a kit comprises an anti-FOLR1 immunoconjugate (e.g., IMGN853) and doxorubicin and instructions to administer the anti-FOLR1 immunoconjugate (e.g., IMGN853), the doxorubicin, and the platinum-based agent. In other embodiments, a kit comprises a platinum-based agent and doxorubicin and instructions to administer the platinum-based agent, the doxorubicin, and an anti-FOLR1 immunoconjugate (e.g., IMGN853).

In certain embodiments, the pharmaceutical compositions provided herein comprise an anti-FOLR1 immunoconjugates (e.g., IMGN853), an anti-VEGF agent (e.g., bevacizumab), a platinum-based agent, and/or doxorubicin and a pharmaceutically acceptable vehicle. In certain embodiments, the pharmaceutical compositions further comprise a preservative. These pharmaceutical compositions find use in inhibiting tumor growth and treating cancer in human patients.

The pharmaceutical compositions for use as provided herein can be administered in any number of ways for either local or systemic treatment. Administration can be topical such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration. In some embodiments, the pharmaceutical composition is formulated for intravenous (i.v.) administration. In some embodiments, the pharmaceutical composition is formulated for intraperitoneal (i.p.) administration.

VII. Methods of Use

As provided herein, anti-FOLR1 immunoconjugates (e.g., IMGN853) can be used in combination with anti-VEGF agents (e.g., bevacizumab), platinum-based agents, and/or doxorubicin to treat cancer.

VII. A. Cancer Selection

Cancers that can be treated by the methods include, but are not limited to, neoplasms, tumors, metastases, or any disease or disorder characterized by uncontrolled cell growth. The cancer can be a primary or metastatic cancer. Specific examples of cancers that can be treated by the methods encompassed by the invention include, but are not limited to ovarian cancer, peritoneal cancer, fallopian tube cancer, lung cancer, colorectal cancer, pancreatic cancer, liver cancer, breast cancer, brain cancer, uterine cancer, non-clear cell kidney (renal) cancer, prostate cancer, gastrointestinal cancer, melanoma, cervical cancer, bladder cancer, glioblastoma, endometrial cancer, and head and neck cancer. More particular examples of such cancers include ovarian cancer, epithelial ovarian cancer, ovarian primary peritoneal cancer, or ovarian fallopian tube cancer. In some embodiments, the subject has previously untreated ovarian cancer. In some embodiment, the subject has newly diagnosed, previously untreated ovarian cancer (e.g., previously untreated with an anti-VEGF antibody, e.g., bevacizumab ("bevacizumab naive")). In other embodiments, the subject has previously treated ovarian cancer (e.g., previously treated with an anti-VEGF antibody, e.g., bevacizumab). In some embodiments, the subject has newly diagnosed, previously untreated (e.g., previously untreated with an anti-VEGF antibody, e.g., bevacizumab ("bevacizumab naive")), stage III (sub-optimally and macroscopic optimally debulked) and IV epithelial ovarian primary peritoneal or fallopian tube cancer. In other embodiments, the subject has previously treated (e.g., previously treated with an anti-VEGF antibody, e.g., bevacizumab) stage III (sub optimally and macroscopic optimally debulked) and IV epithelial ovarian primary peritoneal or fallopian tube cancer. In some embodiments, the subject has platinum sensitive recurrent epithelial ovarian, primary peritoneal, or fallopian tube cancer. In other embodiments, the subject has platinum resistant recurrent epithelial ovarian, primary peritoneal, or fallopian tube cancer.

In certain embodiments, the combination of a FOLR1 immunoconjugate (e.g., IMGN853) and an anti-VEGF agent, a platinum-based agent, and/or doxorubicin is given to a patient diagnosed with or having ovarian cancer, epithelial ovarian cancer, ovarian primary peritoneal cancer, or ovarian fallopian tube cancer who has not received prior treatment with an anti-VEGF antibody, e.g., bevacizumab, ("bevacizumab naive"). In other embodiments, the combination of a FOLR1 immunoconjugate (e.g., IMGN853) and an anti-VEGF agent, a platinum-based agent, and/or doxorubicin is given to a patient diagnosed with or having ovarian cancer, epithelial ovarian cancer, ovarian primary peritoneal cancer, or ovarian fallopian tube cancer who has received treatment with an anti-VEGF antibody, e.g., bevacizumab. In certain aspects of the above embodiments, the cancer is platinum-resistant, platinum-sensitive, platinum sensitive recurrent, platinum resistant recurrent, platinum refractory, primary platinum refractory, or relapsed.

The combination of a FOLR1 immunoconjugate (e.g., IMGN853) and an anti-VEGF agent, a platinum-based agent, and/or doxorubicin can be administered to a patient that has previously been treated with bevacizumab. In some embodiments, the bevacizumab was administered as a single agent in the previous treatment. In some embodiments, the bevacuzimab was administered as part of a combination therapy in the previous treatment.

The combination of a FOLR1 immunoconjugate (e.g., IMGN853) and an anti-VEGF agent, a platinum-based agent, and/or doxorubicin can be administered to a patient that has not previously been treated with bevacizumab (i.e., the patient is "bevacizumab naive").

In certain embodiments, the cancer is ovarian, peritoneal, fallopian tube, endometrial, or lung cancer. The combination of an anti-FOLR1 immunoconjugates (e.g., IMGN853) and an anti-VEGF agent (e.g., bevacizumab), a platinum-based agent, and/or doxorubicin can be administered to an ovarian, peritoneal, fallopian tube, endometrial, or lung cancer as a first-line therapy, a second-line therapy, a third-line therapy, or a fourth or later-line therapy. The combination of an anti-FOLR1 immunoconjugates (e.g., IMGN853) and an anti-VEGF agent (e.g., bevacizumab), a platinum-based agent, and/or doxorubicin can be administered to an ovarian, peritoneal, fallopian tube, endometrial, or lung cancer as an adjuvant therapy or neoadjuvant therapy.

In certain embodiments, the cancer is ovarian cancer. In certain embodiments, the ovarian cancer is epithelial ovarian cancer (EOC). In certain embodiments, the ovarian cancer (e.g., an EOC) is platinum resistant, relapsed, or refractory. The combination of an anti-FOLR1 immunoconjugates (e.g., IMGN853) and an anti-VEGF agent (e.g., bevacizumab), a platinum-based agent, and/or doxorubicin can be administered to an EOC, e.g., an EOC that is platinum resistant, relapsed, or refractory as a first-line therapy, a second-line therapy, a third-line therapy, or a fourth or later-line therapy. The combination of an anti-FOLR1 immunoconjugates (e.g., IMGN853) and an anti-VEGF agent (e.g., bevacizumab), a platinum-based agent, and/or doxorubicin can be administered to an EOC, e.g., an EOC that is platinum resistant, relapsed, or refractory as an adjuvant therapy or a neoadjuvant therapy.

In certain embodiments, the cancer is peritoneal cancer. In certain embodiments, the peritoneal cancer is primary peritoneal cancer. The combination of an anti-FOLR1 immunoconjugates (e.g., IMGN853) and an anti-VEGF agent (e.g., bevacizumab), a platinum-based agent, and/or doxorubicin can be administered to a primary peritoneal cancer as a first-line therapy, a second-line therapy, a third-line therapy, or a fourth or later-line therapy. The combination of an anti-FOLR1 immunoconjugates (e.g., IMGN853) and an anti-VEGF agent (e.g., bevacizumab), a platinum-based agent, and/or doxorubicin can be administered to a primary peritoneal cancer as an adjuvant therapy or a neoadjuvant therapy.

In certain embodiments, the cancer is endometrial cancer. In certain embodiments, the endometrial cancer is serous endometrial cancer. The combination of an anti-FOLR1 immunoconjugates (e.g., IMGN853) and an anti-VEGF agent (e.g., bevacizumab), a platinum-based agent, and/or doxorubicin can be administered to a serous endometrial cancer as a first-line therapy, a second-line therapy, a third-line therapy, or a fourth or later-line therapy. The combination of an anti-FOLR1 immunoconjugates (e.g., IMGN853) and an anti-VEGF agent (e.g., bevacizumab), a platinum-based agent, and/or doxorubicin can be administered to a serous endometrial cancer as an adjuvant therapy or a neoadjuvant therapy.

In certain embodiments, cancer is lung cancer. In certain embodiments, the lung cancer is non-small cell lung cancer (NSCLC). In certain embodiments, the lung cancer is lung cancer is adenocarcinoma or bronchioloalveolar carcinoma. The combination of an anti-FOLR1 immunoconjugates (e.g., IMGN853) and an anti-VEGF agent (e.g., bevacizumab), a platinum-based agent, and/or doxorubicin can be administered to an lung cancer, e.g., a NSCLC, an adenocarcinoma, or a bronchioloalveolar carcinoma as a first-line therapy, a second-line therapy, a third-line therapy, or a fourth or later-line therapy. The combination of an anti-FOLR1 immunoconjugates (e.g., IMGN853) and an anti-VEGF agent (e.g., bevacizumab), a platinum-based agent, and/or doxorubicin can be administered to an lung cancer, e.g., a NSCLC, an adenocarcinoma, or a bronchioloalveolar carcinoma as an adjuvant therapy or a neoadjuvant therapy.

In certain embodiments, the cancer is platinum refractory. In certain embodiments, the cancer is primary platinum refractory. The combination of an anti-FOLR1 immunoconjugates (e.g., IMGN853) and an anti-VEGF agent (e.g., bevacizumab), a platinum-based agent, and/or doxorubicin can be administered to a platinum refractory cancer or a primary platinum refractory cancer as a first-line therapy, a second-line therapy, a third-line therapy, or a fourth or greater-line therapy. The combination of an anti-FOLR1 immunoconjugates (e.g., IMGN853) and an anti-VEGF agent (e.g., bevacizumab), a platinum-based agent, and/or doxorubicin can be administered to a platinum refractory cancer or a primary platinum refractory cancer as an adjuvant therapy or a neoadjuvant therapy.

In certain embodiments, the cancer is platinum sensitive. The combination of an anti-FOLR1 immunoconjugates (e.g., IMGN853) and an anti-VEGF agent (e.g., bevacizumab), a platinum-based agent, and/or doxorubicin can be administered to a platinum sensitive cancer as a first-line therapy, a second-line therapy, a third-line therapy, or a fourth or later-line therapy. The combination of an anti-FOLR1 immunoconjugates (e.g., IMGN853) and an anti-VEGF agent (e.g., bevacizumab), a platinum-based agent, and/or doxorubicin can be administered to a platinum sensitive cancer as an adjuvant therapy or a neoadjuvant therapy.

In certain embodiments, the cancer is a metastatic or advanced cancer. The combination of an anti-FOLR1 immunoconjugates (e.g., IMGN853) and an anti-VEGF agent (e.g., bevacizumab), a platinum-based agent, and/or doxorubicin can be administered to a metastatic or advanced cancer as a first-line therapy, a second-line therapy, a third-line therapy, or a fourth or greater-line therapy. The combination of an anti-FOLR1 immunoconjugates (e.g., IMGN853) and an anti-VEGF agent (e.g., bevacizumab), a platinum-based agent, and/or doxorubicin can be administered to a metastatic or advanced cancer as an adjuvant therapy or a neoadjuvant therapy.

Administration of the combination of an anti-FOLR1 immunoconjugates (e.g., IMGN853) and an anti-VEGF agent (e.g., bevacizumab), a platinum-based agent, and/or doxorubicin as a "second-line" therapy includes administration wherein the first-line therapy was, for example, administration of a single agent, administration of a combination of agents, surgery, radiation, or a combination thereof.

Administration of the combination of an anti-FOLR1 immunoconjugates (e.g., IMGN853) and an anti-VEGF agent (e.g., bevacizumab), a platinum-based agent, and/or doxorubicin as a "third-line" therapy includes administration wherein the first-line therapy was, for example, administration of a single agent, administration of a combination of agents, surgery, radiation, or a combination thereof and wherein the second-line therapy was, for example, administration of a single agent, administration of a combination of agents, surgery, radiation, or a combination thereof. Thus, administration of the combination of an anti-FOLR1 immunoconjugates (e.g., IMGN853) and an anti-VEGF agent (e.g., bevacizumab), a platinum-based agent, and/or doxorubicin as a "third-line" therapy includes for example, administration following a first-line therapy that was administration of a single agent, and a second-line therapy that was administration of a combination of agents. Administration of the combination of an anti-FOLR1 immunoconjugates (e.g., IMGN853) and an anti-VEGF agent (e.g., bevacizumab), a platinum-based agent, and/or doxorubicin as a "third-line" therapy also includes, for example, administration following a first-line therapy that was administration of a combination of agents, and a second-line therapy that was administration of a single agent. Administration of the combination of an anti-FOLR1 immunoconjugates (e.g., IMGN853) and an anti-VEGF agent (e.g., bevacizumab), a platinum-based agent, and/or doxorubicin as a "third-line" therapy includes, for example, administration following a first-line therapy that was administration of a combination of agents, and a second-line therapy that was administration of a combination of agents. Administration of the combination of an anti-FOLR1 immunoconjugates (e.g., IMGN853) and an anti-VEGF agent (e.g., bevacizumab), a platinum-based agent, and/or doxorubicin as a "third-line" therapy also includes, for example, administration following a first-line therapy that was administration of a combination of agents and a surgery, and a second-line therapy that was administration of a combination of agents.

In some embodiments, the cancer is a cancer that expresses FOLR1 (polypeptide or nucleic acid). In some embodiments, the combination of the anti-FOLR1 immunoconjugate (e.g., IMGN853) and the anti-VEGF agent, the platinum-based agent, and/or the doxorubicin is administered to a patient with an increased expression level of FOLR1, for example, as described in U.S. Published Application No. 2012/0282175 or International Published Application No. WO 2012/135675, both of which are incorporated by reference herein in their entireties. Exemplary antibodies, assays, and kits for the detection of FOLR1 are provided in WO 2014/036495 and WO 2015/031815, both of which are incorporated by reference herein in their entireties. Thus, in some embodiments, the FOLR1 protein expression is measured by immunohistochemistry (IHC) and given a staining intensity score and/or a staining uniformity score by comparison to controls (e.g., calibrated controls) exhibiting defined scores (e.g. an intensity score of 3 is given to the test sample if the intensity is comparable to the level 3 calibrated control or an intensity of 2 (moderate) is given to the test sample if the intensity is comparable to the level 2 calibrated control). A staining uniformity that is "heterogeneous" (i.e., at least 25% and less than 75% cells stained) or "homogeneous" (i.e., at least 75% cells stained) instead of "focal" (i.e., greater than 0% and less than 25% cells stained) is also indicative of increased FOLR1 expression. The staining intensity and staining uniformity scores can be used alone or in combination (e.g., 2 homo, 2 hetero, 3 homo, 3 hetero, etc.). In another example, an increase in FOLR1 expression can be determined by detection of an increase of at least 2-fold, at least 3-fold, or at least 5-fold) relative to control values (e.g., expression level in a tissue or cell from a subject without cancer or with a cancer that does not have elevated FOLR1 values). In some embodiments, the staining uniformity score is based on the percent of stained cells.

In some embodiments, the cancer is a cancer that expresses FOLR1 at a level of 1 hetero or higher by IHC. In some embodiments, the cancer is a cancer that expresses FOLR1 at a level of 2 hetero or higher by IHC. In some embodiments, the cancer is a cancer that expresses FOLR1 at a level of 3 hetero or higher by IHC. In some embodiments, the cancer is a lung cancer that expresses FOLR1 at a level of 2 hetero or higher by IHC. In some embodiments, the cancer is a lung cancer that expresses FOLR1 at a level of 3 hetero or higher by IHC. In some embodiments, the cancer is an ovarian cancer that expresses FOLR1 at a level of 2 hetero or higher by IHC. In some embodiments, the cancer is an ovarian cancer that expresses FOLR1 at a level of 3 hetero or higher by IHC. In some embodiments, the cancer is an endometrial cancer that expresses FOLR1 at a level of 2 hetero or higher by IHC. In some embodiments, the cancer is an endometrioid cancer that expresses FOLR1 at a level of 1 hetero or higher by IHC.

In some embodiments, at least one cell in sample obtained from a patient has an FOLR1 score of at least 1. In some embodiments, at least one cell in sample obtained from a patient has an FOLR1 score of at least 2 (moderate). In some embodiments, at least one cell in sample obtained from a patient has an FOLR1 score of at least 3.

In some embodiments, at least 25% of the cells in a sample obtained from a patient have a FOLR1 IHC score of at least 1. In some embodiments, at least 33% of the cells in a sample obtained from a patient have a FOLR1 IHC score of at least 1. In some embodiments, at least 50% of the cells in a sample obtained from a patient have a FOLR1 IHC score of at least 1. In some embodiments, at least 66% of the cells in a sample obtained from a patient have a FOLR1 IHC score of at least 1. In some embodiments, at least 75% of the cells in a sample obtained from a patient have a FOLR1 IHC score of at least 1.

In some embodiments, at least 25% of the cells in a sample obtained from a patient have a FOLR1 IHC score of at least 2 (moderate). In some embodiments, at least 33% of the cells in a sample obtained from a patient have a FOLR1 IHC score of at least 2 (moderate). In some embodiments, 25-75% of the cells in a sample obtained from a patient have a FOLR1 IHC score of at least 2 (moderate). In some embodiments, at least 50% of the cells in a sample obtained from a patient have a FOLR1 IHC score of at least 2 (moderate). In some embodiments, at least 66% of the cells in a sample obtained from a patient have a FOLR1 IHC score of at least 2 (moderate). In some embodiments, at least 75% of the cells in a sample obtained from a patient have a FOLR1 IHC score of at least 2 (moderate).

In some embodiments, at least 25% of the cells in a sample obtained from a patient have a FOLR1 IHC score of at least 3. In some embodiments, at least 33% of the cells in a sample obtained from a patient have a FOLR1 IHC score of at least 3. In some embodiments, at least 50% of the cells in a sample obtained from a patient have a FOLR1 IHC score of at least 3. In some embodiments, at least 66% of the cells in a sample obtained from a patient have a FOLR1 IHC score of at least 3. In some embodiments, at least 75% of the cells in a sample obtained from a patient have a FOLR1 IHC score of at least 3.

In one embodiment, immunological detection (by immunohistochemistry) of FOLR1 is scored using H-scores. H-scores combine staining intensity scores (e.g., a score of 0 to 3, wherein 0 represents no staining, and 3 represents strong staining) with the percentage of cells that are positive for membrane staining (i.e., uniformity). An H-score can be calculated as follows:

$H$ score=[0*(percentage of cells staining at intensity 0)]+[1*(percentage of cells staining at intensity 1)]+[2*(percentage of cells staining at intensity 2)]+[3*(percentage of cells staining at intensity 3)].

Accordingly, an H-score can range from 0 (no cell membranes staining) to 300 (all cell membranes staining at intensity 3).

VII. B. Dosing

As provided herein, an anti-FOLR1 immunoconjugate (e.g., IMGN853) can be administered at a particular dose and/or at particular timing intervals. Administration of anti-FOLR1 immunoconjugates (e.g., IMGN853) can be, for example, intravenous or intraperitoneal. Dosing regiments for anti-FORL1 immunoconjugates (e.g., IMGN853) are provided, for example, in WO 2014/186403, WO 2015/054400, and WO 2015/149018, each of which is herein incorporated by reference in its entirety.

For example, an anti-FOLR1 immunoconjugate (e.g., IMGN853) can be administered at a dose of about 0.15 mg/kg to about 7 mg/kg, wherein the kilograms of body weight are adjusted to ideal body weight (IBW), lean body weight (LBW), body surface area (BSA), or adjusted ideal body weight (AIBW). An anti-FOLR1 immunoconjugate (e.g., IMGN853) can also be administered at a dose of about 1 mg/kg to about 6 mg/kg IBW, LBW, BSA, or AIBW. An anti-FOLR1 immunoconjugate (e.g., IMGN853) can also be administered at a dose of about 3 mg/kg to about 6 mg/kg IBW, LBW, BSA, or AIBW. An anti-FOLR1 immunoconjugate (e.g., IMGN853) can also be administered using fractionated dosing.

An anti-FOLR1 immunoconjugate (e.g., IMGN853) can be administered at a dose of about 0.15 mg/kg to about 7 mg/kg based on total body weight (TBW). An anti-FOLR1 immunoconjugate (e.g., IMGN853) can also be administered at a dose of about 1 mg/kg to about 6 mg/kg TBW. An anti-FOLR1 immunoconjugate (e.g., IMGN853) can also be administered at a dose of about 3 mg/kg to about 6 mg/kg TBW.

In some embodiments, an anti-FOLR1 immunoconjugate (e.g., IMGN853) is administered every three weeks. In some embodiments, an anti-FOLR1 immunoconjugate (e.g., IMGN853) is administered every three weeks at a dose of about 4 mg/kg AIBW. In some embodiments, an anti-FOLR1 immunoconjugate (e.g., IMGN853) is administered every three weeks at a dose of about 5 mg/kg AIBW. In some embodiments, an anti-FOLR1 immunoconjugate (e.g., IMGN853) is administered every three weeks at a dose of about 6 mg/kg AIBW.

In some embodiments, an anti-FOLR1 immunoconjugate (e.g., IMGN853) is administered every four weeks. In some embodiments, an anti-FOLR1 immunoconjugate (e.g., IMGN853) is administered every four weeks at a dose of about 4 mg/kg AIBW. In some embodiments, an anti-FOLR1 immunoconjugate (e.g., IMGN853) is administered every four weeks at a dose of about 5 mg/kg AIBW. In some embodiments, an anti-FOLR1 immunoconjugate (e.g., IMGN853) is administered every four weeks at a dose of about 6 mg/kg AIBW.

In some embodiments, an anti-FOLR1 immunoconjugate (e.g., IMGN853) is administered every two weeks. In some embodiments, an anti-FOLR1 immunoconjugate (e.g., IMGN853) is administered every two weeks at a dose of about 2.0 mg/kg AIBW. In some embodiments, an anti-FOLR1 immunoconjugate (e.g., IMGN853) is administered every two weeks at a dose of about 2.5 mg/kg AIBW. In some embodiments, an anti-FOLR1 immunoconjugate (e.g., IMGN853) is administered every two weeks at a dose of about 3 mg/kg AIBW. In some embodiments, an anti-FOLR1 immunoconjugate (e.g., IMGN853) is administered every two weeks at a dose of about 3.5 mg/kg AIBW. In some embodiments, an anti-FOLR1 immunoconjugate (e.g., IMGN853) is administered every two weeks at a dose of about 4 mg/kg AIBW.

In some embodiments, an anti-FOLR1 immunoconjugate (e.g., IMGN853) is administered weekly. In some embodiments, an anti-FOLR1 immunoconjugate (e.g., IMGN853) is administered every week at a dose of about 1.1 mg/kg AIBW. In some embodiments, an anti-FOLR1 immunoconjugate (e.g., IMGN853) is administered every week at a dose of about 1.8 mg/kg AIBW. In some embodiments, an anti-FOLR1 immunoconjugate (e.g., IMGN853) is administered every week at a dose of about 2.0 mg/kg AIBW. In some embodiments, an anti-FOLR1 immunoconjugate (e.g., IMGN853) is administered every week at a dose of about 2.5 mg/kg AIBW.

In some embodiments, an anti-FOLR1 immunoconjugate (e.g., IMGN853) is administered one a week for three weeks on a four-week schedule (e.g., on days 1, 8, and 15 of a 28-day cycle).

As provided herein, an anti-VEGF agent can be administered at a particular dose and/or at particular timing intervals. An anti-VEGF agent (e.g., bevacizumab) can also be administered using fractionated dosing. Administration of an anti-VEGF agent (e.g., bevacizumab) can be, for example, intravenous.

In some embodiments, an anti-VEGF agent (e.g., bevacizumab) is administered every three weeks. In some embodiments, an anti-VEGF agent (e.g., bevacizumab) is administered every two weeks. In some embodiments, an anti-VEGF agent (e.g., bevacizumab) is administered twice every four weeks (e.g., on days 1 and 15 of a 28-day cycle).

In some embodiments, an anti-VEGF agent (e.g., bevacizumab) is administered at a dose of about 15 mg/kg. In some embodiments, an anti-VEGF agent (e.g., bevacizumab) is administered at a dose of about 10 mg/kg. In some embodiments, an anti-VEGF agent (e.g., bevacizumab) is administered at a dose of about 7.5 mg/kg.

In some embodiments, an anti-VEGF agent (e.g., bevacizumab) is administered every three weeks administered at a dose of about 15 mg/kg. In some embodiments, an anti-VEGF agent (e.g., bevacizumab) is administered every two weeks administered at a dose of about 10 mg/kg. In some embodiments, an anti-VEGF agent (e.g., bevacizumab) is administered twice every four weeks at a dose of about 10 mg/kg each time. In some embodiments, an anti-VEGF agent (e.g., bevacizumab) is administered every two weeks administered at a dose of about 7.5 mg/kg.

In some embodiments, an anti-VEGF agent is a soluble VEGF receptor such as VEGF-TRAP. In some embodiments an anti-VEGF agent such as VEGF-TRAP is administered every two weeks. In some embodiments an anti-VEGF agent such as VEGF-TRAP is administered at a dose of about 4 mg/kg. In some embodiments an anti-VEGF agent such as VEGF-TRAP is administered every two weeks at a dose of about 4 mg/kg.

In some embodiments, an anti-VEGF agent (e.g., bevacizumab) is administered every three weeks administered at a dose of about 15 mg/kg and an anti-FOLR1 immunoconjugate (e.g., IMGN853) is administered every three weeks.

In some embodiments, an anti-VEGF agent (e.g., bevacizumab) is administered every three weeks administered at a dose of about 15 mg/kg and an anti-FOLR1 immunoconjugate (e.g., IMGN853) is administered every three weeks at a dose of about 4 mg/kg AIBW. In some embodiments, an anti-VEGF agent (e.g., bevacizumab) is administered every three weeks administered at a dose of about 15 mg/kg and an anti-FOLR1 immunoconjugate (e.g., IMGN853) is administered every three weeks at a dose of about 5 mg/kg AIBW. In some embodiments, an anti-VEGF agent (e.g., bevacizumab) is administered every three weeks administered at a dose of about 15 mg/kg and an anti-FOLR1 immunoconjugate (e.g., IMGN853) is administered every three weeks at a dose of about 6 mg/kg AIBW.

In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, and an anti-FOLR1 immunoconjugate (e.g., IMGN853) is administered every four weeks. In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, and an anti-FOLR1 immunoconjugate (e.g., IMGN853) is administered every four weeks at a dose of about 4 mg/kg AIBW. In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, and an anti-FOLR1 immunoconjugate (e.g., IMGN853) is administered every four weeks at a dose of about 5 mg/kg AIBW. In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, and an anti-FOLR1 immunoconjugate (e.g., IMGN853) is administered every four weeks at a dose of about 6 mg/kg AIBW.

As provided herein, a platinum-based agent can be administered at a particular dose and/or at particular timing intervals. Administration of the platinum-based agent can be, for example, intravenous. The platinum-based agent can be e.g., carboplatin or cisplatin.

As provided herein, carboplatin can be administered at a particular dose and/or at particular timing intervals. Administration of carboplatin can be, for example, intravenous.

In some embodiments, carboplatin is administered every three weeks.

A formula for calculating dosage, based upon a patient's glomerular filtration rate (GFR in mL/min) and carboplatin injection target area under the concentration versus time curve (AUC in mg/mL·min), can be used: Total Dose (mg)=(target AUC)×(GFR+25).

In some embodiments, carboplatin is administered at a dose that produces an AUC of 4 mg/mL·min. In some embodiments, carboplatin is administered at a dose that produces an AUC of 5 mg/mL·min. In some embodiments, carboplatin is administered at a dose that produces an AUC of 6 mg/mL·min. In some embodiments, carboplatin is administered at a dose that produces an AUC of 7 mg/mL·min.

In some embodiments, carboplatin is administered every three weeks at a dose that produces an AUC of 4 mg/mL·min. In some embodiments, carboplatin is administered every three weeks at a dose that produces an AUC of 5 mg/mL·min. In some embodiments, carboplatin is administered every three weeks at a dose that produces an AUC of 6 mg/mL·min. In some embodiments, carboplatin is administered every three weeks at a dose that produces an AUC of 7 mg/mL·min.

In some embodiments, carboplatin is administered every four weeks.

In some embodiments, carboplatin is administered at a dose of 360 mg/m². In some embodiments, carboplatin is administered at a dose of about 300 mg/m².

In some embodiments, carboplatin is administered every four weeks at a dose of 360 mg/m². In some embodiments, carboplatin is administered every four weeks at a dose of about 300 mg/m².

As provided herein, cisplatin can be administered at a particular dose and/or at particular timing intervals. Administration of cisplatin can be, for example, intravenous.

In some embodiments, cisplatin is administered every four weeks. In some embodiments, cisplatin is administered every three weeks.

In some embodiments, cisplatin is administered at a dose of about 100 mg/m². In some embodiments, cisplatin is administered at a dose of about 75-100 mg/m². In some embodiments, cisplatin is administered at a dose of about 50-70 mg/m². In some embodiments, cisplatin is administered at a dose of about 20 mg/m².

In some embodiments, cisplatin is administered every four weeks at a dose of about 100 mg/m². In some embodiments, cisplatin is administered every four weeks at a dose of about 75-100 mg/m².

In some embodiments, cisplatin is administered every three weeks at a dose of about 50-70 mg/m².

In some embodiments, carboplatin is administered every three weeks administered at a dose that produces an AUC of 4 mg/mL·min and an anti-FOLR1 immunoconjugate (e.g., IMGN853) is administered every three weeks. In some embodiments, carboplatin is administered every three weeks administered at a dose that produces an AUC of 4 mg/mL·min and an anti-FOLR1 immunoconjugate (e.g., IMGN853) is administered every three weeks at a dose of about 4 mg/kg AIBW. In some embodiments, carboplatin is administered every three weeks administered at a dose that produces an AUC of 4 mg/mL·min and an anti-FOLR1 immunoconjugate (e.g., IMGN853) is administered every three weeks at a dose of about 5 mg/kg AIBW. In some embodiments, carboplatin is administered every three weeks administered at a dose that produces an AUC of 4 mg/mL·min and an anti-FOLR1 immunoconjugate (e.g., IMGN853) is administered every three weeks at a dose of about 6 mg/kg AIBW.

In some embodiments, carboplatin is administered every three weeks administered at a dose that produces an AUC of 5 mg/mL·min and an anti-FOLR1 immunoconjugate (e.g., IMGN853) is administered every three weeks. In some embodiments, carboplatin is administered every three weeks administered at a dose that produces an AUC of 5 mg/mL·min and an anti-FOLR1 immunoconjugate (e.g., IMGN853) is administered every three weeks at a dose of about 4 mg/kg AIBW. In some embodiments, carboplatin is administered every three weeks administered at a dose that produces an AUC of 5 mg/mL·min and an anti-FOLR1 immunoconjugate (e.g., IMGN853) is administered every three weeks at a dose of about 5 mg/kg AIBW. In some embodiments, carboplatin is administered every three weeks administered at a dose that produces an AUC of 5 mg/mL·min and an anti-FOLR1 immunoconjugate (e.g., IMGN853) is administered every three weeks at a dose of about 6 mg/kg AIBW.

In some embodiments, carboplatin is administered every three weeks administered at a dose that produces an AUC of 6 mg/mL·min and an anti-FOLR1 immunoconjugate (e.g., IMGN853) is administered every three weeks. In some embodiments, carboplatin is administered every three weeks administered at a dose that produces an AUC of 6 mg/mL·min and an anti-FOLR1 immunoconjugate (e.g., IMGN853) is administered every three weeks at a dose of about 4 mg/kg AIBW. In some embodiments, carboplatin is administered every three weeks administered at a dose that produces an AUC of 6 mg/mL·min and an anti-FOLR1 immunoconjugate (e.g., IMGN853) is administered every three weeks at a dose of about 5 mg/kg AIBW. In some embodiments, carboplatin is administered every three weeks administered at a dose that produces an AUC of 6 mg/mL·min and an anti-FOLR1 immunoconjugate (e.g., IMGN853) is administered every three weeks at a dose of about 6 mg/kg AIBW.

In some embodiments, carboplatin is administered every three weeks administered at a dose that produces an AUC of 7 mg/mL·min and an anti-FOLR1 immunoconjugate (e.g., IMGN853) is administered every three weeks. In some embodiments, carboplatin is administered every three weeks administered at a dose that produces an AUC of 7 mg/mL·min and an anti-FOLR1 immunoconjugate (e.g., IMGN853) is administered every three weeks at a dose of about 4 mg/kg AIBW. In some embodiments, carboplatin is administered every three weeks administered at a dose that produces an AUC of 7 mg/mL·min and an anti-FOLR1 immunoconjugate (e.g., IMGN853) is administered every three weeks at a dose of about 5 mg/kg AIBW. In some embodiments, carboplatin is administered every three weeks administered at a dose that produces an AUC of 7 mg/mL·min and an anti-FOLR1 immunoconjugate (e.g., IMGN853) is administered every three weeks at a dose of about 6 mg/kg AIBW.

In some embodiments, an anti-VEGF agent (e.g., bevacizumab) is administered every three weeks administered at a dose of about 15 mg/kg, carboplatin is administered every three weeks administered at a dose that produces an AUC of 4 mg/mL·min, and an anti-FOLR1 immunoconjugate (e.g., IMGN853) is administered every three weeks. In some embodiments, an anti-VEGF agent (e.g., bevacizumab) is administered every three weeks administered at a dose of about 15 mg/kg, carboplatin is administered every three weeks administered at a dose that produces an AUC of 4 mg/mL·min, and an anti-FOLR1 immunoconjugate (e.g., IMGN853) is administered every three weeks at a dose of about 4 mg/kg AIBW. In some embodiments, an anti-VEGF agent (e.g., bevacizumab) is administered every three weeks administered at a dose of about 15 mg/kg, carboplatin is administered every three weeks administered at a dose that produces an AUC of 4 mg/mL·min, and an anti-FOLR1 immunoconjugate (e.g., IMGN853) is administered every three weeks at a dose of about 5 mg/kg AIBW. In some embodiments, an anti-VEGF agent (e.g., bevacizumab) is administered every three weeks administered at a dose of about 15 mg/kg, carboplatin is administered every three weeks administered at a dose that produces an AUC of 4 mg/mL·min, and an anti-FOLR1 immunoconjugate (e.g., IMGN853) is administered every three weeks at a dose of about 6 mg/kg AIBW.

In some embodiments, an anti-VEGF agent (e.g., bevacizumab) is administered every three weeks administered at a dose of about 15 mg/kg, carboplatin is administered every three weeks administered at a dose that produces an AUC of 5 mg/mL·min, and an anti-FOLR1 immunoconjugate (e.g., IMGN853) is administered every three weeks. In some embodiments, an anti-VEGF agent (e.g., bevacizumab) is administered every three weeks administered at a dose of about 15 mg/kg, carboplatin is administered every three weeks administered at a dose that produces an AUC of 5 mg/mL·min, and an anti-FOLR1 immunoconjugate (e.g., IMGN853) is administered every three weeks at a dose of about 4 mg/kg AIBW. In some embodiments, an anti-VEGF agent (e.g., bevacizumab) is administered every three weeks administered at a dose of about 15 mg/kg, carboplatin is administered every three weeks administered at a dose that produces an AUC of 5 mg/mL·min, and an anti-FOLR1 immunoconjugate (e.g., IMGN853) is administered every three weeks at a dose of about 5 mg/kg AIBW. In some embodiments, an anti-VEGF agent (e.g., bevacizumab) is administered every three weeks administered at a dose of about 15 mg/kg, carboplatin is administered every three weeks administered at a dose that produces an AUC of 5 mg/mL·min, and an anti-FOLR1 immunoconjugate (e.g., IMGN853) is administered every three weeks at a dose of about 6 mg/kg AIBW.

In some embodiments, an anti-VEGF agent (e.g., bevacizumab) is administered every three weeks administered at a dose of about 15 mg/kg, carboplatin is administered every three weeks administered at a dose that produces an AUC of 6 mg/mL·min, and an anti-FOLR1 immunoconjugate (e.g., IMGN853) is administered every three weeks. In some embodiments, an anti-VEGF agent (e.g., bevacizumab) is administered every three weeks administered at a dose of about 15 mg/kg, carboplatin is administered every three weeks administered at a dose that produces an AUC of 6 mg/mL·min, and an anti-FOLR1 immunoconjugate (e.g., IMGN853) is administered every three weeks at a dose of about 4 mg/kg AIBW. In some embodiments, an anti-VEGF agent (e.g., bevacizumab) is administered every three weeks administered at a dose of about 15 mg/kg, carboplatin is administered every three weeks administered at a dose that produces an AUC of 6 mg/mL·min, and an anti-FOLR1 immunoconjugate (e.g., IMGN853) is administered every three weeks at a dose of about 5 mg/kg AIBW. In some embodiments, an anti-VEGF agent (e.g., bevacizumab) is administered every three weeks administered at a dose of about 15 mg/kg, carboplatin is administered every three weeks administered at a dose that produces an AUC of 6 mg/mL·min, and an anti-FOLR1 immunoconjugate (e.g., IMGN853) is administered every three weeks at a dose of about 6 mg/kg AIBW.

In some embodiments, an anti-VEGF agent (e.g., bevacizumab) is administered every three weeks administered at a dose of about 15 mg/kg, carboplatin is administered every three weeks administered at a dose that produces an AUC of 7 mg/mL·min, and an anti-FOLR1 immunoconjugate (e.g., IMGN853) is administered every three weeks. In some embodiments, an anti-VEGF agent (e.g., bevacizumab) is administered every three weeks administered at a dose of about 15 mg/kg, carboplatin is administered every three weeks administered at a dose that produces an AUC of 7 mg/mL·min, and an anti-FOLR1 immunoconjugate (e.g., IMGN853) is administered every three weeks at a dose of about 4 mg/kg AIBW. In some embodiments, an anti-VEGF agent (e.g., bevacizumab) is administered every three weeks administered at a dose of about 15 mg/kg, carboplatin is administered every three weeks administered at a dose that produces an AUC of 7 mg/mL·min, and an anti-FOLR1 immunoconjugate (e.g., IMGN853) is administered every three weeks at a dose of about 5 mg/kg AIBW. In some embodiments, an anti-VEGF agent (e.g., bevacizumab) is administered every three weeks administered at a dose of about 15 mg/kg, carboplatin is administered every three weeks administered at a dose that produces an AUC of 7 mg/mL·min, and an anti-FOLR1 immunoconjugate (e.g., IMGN853) is administered every three weeks at a dose of about 6 mg/kg AIBW.

In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, carboplatin is administered every three weeks administered at a dose that produces an AUC of 4 mg/mL·min, and an anti-FOLR1 immunoconjugate (e.g., IMGN853) is administered every four weeks. In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, and an anti-FOLR1 immunoconjugate (e.g., IMGN853) is administered every four weeks at a dose of about 4 mg/kg AIBW, carboplatin is administered every three weeks administered at a dose that produces an AUC of 4 mg/mL·min. In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, carboplatin is administered every three weeks administered at a dose that produces an AUC of 4 mg/mL·min, and an anti-FOLR1 immunoconjugate (e.g., IMGN853) is administered every four weeks at a dose of about 5 mg/kg AIBW. In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, carboplatin is administered every three weeks administered at a dose that produces an AUC of 4 mg/mL·min, and an anti-FOLR1 immunoconjugate (e.g., IMGN853) is administered every four weeks at a dose of about 6 mg/kg AIBW.

In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, carboplatin is administered every three weeks administered at a dose that produces an AUC of 5 mg/mL·min, and an anti-FOLR1 immunoconjugate (e.g., IMGN853) is administered every four weeks. In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, and an anti-FOLR1 immunoconjugate (e.g., IMGN853) is administered every four weeks at a dose of about 4 mg/kg AIBW, carboplatin is administered every three weeks administered at a dose that produces an AUC of 5 mg/mL·min. In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, carboplatin is administered every three weeks administered at a dose that produces an AUC of 5 mg/mL·min, and an anti-FOLR1 immunoconjugate (e.g., IMGN853) is administered every four weeks at a dose of about 5 mg/kg AIBW. In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, carboplatin is administered every three weeks administered at a dose that produces an AUC of 5 mg/mL·min, and an anti-FOLR1 immunoconjugate (e.g., IMGN853) is administered every four weeks at a dose of about 6 mg/kg AIBW.

In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, carboplatin is administered every three weeks administered at a dose that produces an AUC of 6 mg/mL·min, and an anti-FOLR1 immunoconjugate (e.g., IMGN853) is administered every four weeks. In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, and an anti-FOLR1 immunoconjugate (e.g., IMGN853) is administered every four weeks at a dose of about 4 mg/kg AIBW, carboplatin is administered every three weeks administered at a dose that produces an AUC of 6 mg/mL·min. In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, carboplatin is administered every three weeks administered at a dose that produces an AUC of 6 mg/mL·min, and an anti-FOLR1 immunoconjugate (e.g., IMGN853) is administered every four weeks at a dose of about 5 mg/kg AIBW. In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, carboplatin is administered every three weeks administered at a dose that produces an AUC of 6 mg/mL·min, and an anti-FOLR1 immunoconjugate (e.g., IMGN853) is administered every four weeks at a dose of about 6 mg/kg AIBW.

In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, carboplatin is administered every three weeks administered at a dose that produces an AUC of 7 mg/mL·min, and an anti-FOLR1 immunoconjugate (e.g., IMGN853) is administered every four weeks. In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, and an anti-FOLR1 immunoconjugate (e.g., IMGN853) is administered every four weeks at a dose of about 4 mg/kg AIBW, carboplatin is administered every three weeks administered at a dose that produces an AUC of 7 mg/mL·min. In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, carboplatin is administered every three weeks administered at a dose that produces an AUC of 7 mg/mL·min, and an anti-FOLR1 immunoconjugate (e.g., IMGN853) is administered every four weeks at a dose of about 5 mg/kg AIBW. In some embodiments, an anti-VEGF agent (e.g., bevacizumab) is administered every two weeks administered at a dose of about 10 mg/kg or about 7.5 mg/kg or administered twice every four weeks (e.g., on days 1 and 15 of a 28-day cycle) at a dose of about 10 mg/kg each time, carboplatin is administered every three weeks administered at a dose that produces an AUC of 7 mg/mL·min, and an anti-FOLR1 immunoconjugate (e.g., IMGN853) is administered every four weeks at a dose of about 6 mg/kg AIBW.

As provided herein, doxorubicin can be administered at a particular dose and/or at particular timing intervals. Administration of doxorubicin (e.g., pegylated liposomal doxorubicin (PLD)) can be, for example, intravenous.

In some embodiments, doxorubicin (e.g., PLD) is administered every four weeks.

In some embodiments, doxorubicin (e.g., PLD) is administered at a dose of about 30 mg/m$^2$. In some embodiments, doxorubicin (e.g., PLD) is administered at a dose of about 35 mg/m$^2$. In some embodiments, doxorubicin (e.g., PLD) is administered at a dose of about 40 mg/m$^2$. In some embodiments, doxorubicin (e.g., PLD) is administered at a dose of about 45 mg/m$^2$. In some embodiments, doxorubicin (e.g., PLD) is administered at a dose of about 50 mg/m$^2$.

In some embodiments, doxorubicin (e.g., PLD) is administered every four weeks at a dose of about 30 mg/m$^2$. In some embodiments, doxorubicin (e.g., PLD) is administered every four weeks at a dose of about 35 mg/m$^2$. In some embodiments, doxorubicin (e.g., PLD) is administered every four weeks at a dose of about 40 mg/m$^2$. In some embodiments, doxorubicin (e.g., PLD) is administered every four weeks at a dose of about 45 mg/m$^2$. In some embodiments, doxorubicin (e.g., PLD) is administered every four weeks at a dose of about 50 mg/m$^2$.

In some embodiments, doxorubicin (e.g., PLD) is administered every four weeks at a dose of about 30 mg/m$^2$ and an anti-FOLR1 immunoconjugate (e.g., IMGN853) is administered every four weeks. In some embodiments, doxorubicin (e.g., PLD) is administered every four weeks at a dose of about 30 mg/m$^2$ and an anti-FOLR1 immunoconjugate (e.g., IMGN853) is administered every four weeks at a dose of about 4 mg/kg AIBW. In some embodiments, doxorubicin (e.g., PLD) is administered every four weeks at a dose of about 30 mg/m$^2$ and an anti-FOLR1 immunoconjugate (e.g., IMGN853) is administered every four weeks at a dose of about 5 mg/kg AIBW. In some embodiments, doxorubicin (e.g., PLD) is administered every four weeks at a dose of about 30 mg/m$^2$ and an anti-FOLR1 immunoconjugate (e.g., IMGN853) is administered every four weeks at a dose of about 6 mg/kg AIBW.

In some embodiments, doxorubicin (e.g., PLD) is administered every four weeks at a dose of about 35 mg/m$^2$ and an anti-FOLR1 immunoconjugate (e.g., IMGN853) is administered every four weeks. In some embodiments, doxorubicin (e.g., PLD) is administered every four weeks at a dose of about 35 mg/m$^2$ and an anti-FOLR1 immunoconjugate (e.g., IMGN853) is administered every four weeks at a dose of about 4 mg/kg AIBW. In some embodiments, doxorubicin (e.g., PLD) is administered every four weeks at a dose of about 35 mg/m$^2$ and an anti-FOLR1 immunoconjugate (e.g., IMGN853) is administered every four weeks at a dose of about 5 mg/kg AIBW. In some embodiments, doxorubicin (e.g., PLD) is administered every four weeks at a dose of about 35 mg/m² and an anti-FOLR1 immunoconjugate (e.g., IMGN853) is administered every four weeks at a dose of about 6 mg/kg AIBW.

In some embodiments, doxorubicin (e.g., PLD) is administered every four weeks at a dose of about 40 mg/m² and an anti-FOLR1 immunoconjugate (e.g., IMGN853) is administered every four weeks. In some embodiments, doxorubicin (e.g., PLD) is administered every four weeks at a dose of about 40 mg/m² and an anti-FOLR1 immunoconjugate (e.g., IMGN853) is administered every four weeks at a dose of about 4 mg/kg AIBW. In some embodiments, doxorubicin (e.g., PLD) is administered every four weeks at a dose of about 40 mg/m² and an anti-FOLR1 immunoconjugate (e.g., IMGN853) is administered every four weeks at a dose of about 5 mg/kg AIBW. In some embodiments, doxorubicin (e.g., PLD) is administered every four weeks at a dose of about 40 mg/m² and an anti-FOLR1 immunoconjugate (e.g., IMGN853) is administered every four weeks at a dose of about 6 mg/kg AIBW.

In some embodiments, doxorubicin (e.g., PLD) is administered every four weeks at a dose of about 45 mg/m² and an anti-FOLR1 immunoconjugate (e.g., IMGN853) is administered every four weeks. In some embodiments, doxorubicin (e.g., PLD) is administered every four weeks at a dose of about 45 mg/m² and an anti-FOLR1 immunoconjugate (e.g., IMGN853) is administered every four weeks at a dose of about 4 mg/kg AIBW. In some embodiments, doxorubicin (e.g., PLD) is administered every four weeks at a dose of about 45 mg/m² and an anti-FOLR1 immunoconjugate (e.g., IMGN853) is administered every four weeks at a dose of about 5 mg/kg AIBW. In some embodiments, doxorubicin (e.g., PLD) is administered every four weeks at a dose of about 45 mg/m² and an anti-FOLR1 immunoconjugate (e.g., IMGN853) is administered every four weeks at a dose of about 6 mg/kg AIBW.

In some embodiments, doxorubicin (e.g., PLD) is administered every four weeks at a dose of about 50 mg/m² and an anti-FOLR1 immunoconjugate (e.g., IMGN853) is administered every four weeks. In some embodiments, doxorubicin (e.g., PLD) is administered every four weeks at a dose of about 50 mg/m² and an anti-FOLR1 immunoconjugate (e.g., IMGN853) is administered every four weeks at a dose of about 4 mg/kg AIBW. In some embodiments, doxorubicin (e.g., PLD) is administered every four weeks at a dose of about 50 mg/m² and an anti-FOLR1 immunoconjugate (e.g., IMGN853) is administered every four weeks at a dose of about 5 mg/kg AIBW. In some embodiments, doxorubicin (e.g., PLD) is administered every four weeks at a dose of about 50 mg/m² and an anti-FOLR1 immunoconjugate (e.g., IMGN853) is administered every four weeks at a dose of about 6 mg/kg AIBW.

In one instance, the immunoconjugate that binds to FOLR1 (e.g., IMGN853) and the anti-VEGF agent are administered simultaneously. In one instance, the anti-FOLR1 immunoconjugate (e.g., IMGN853) and the anti-VEGF agent are administered in separate pharmaceutical compositions. In one instance, the anti-FOLR1 immunoconjugate (e.g., IMGN853) and the anti-VEGF agent are administered in the same pharmaceutical composition. In one instance, the anti-FOLR1 immunoconjugate (e.g., IMGN853) and the anti-VEGF agent are administered sequentially. In such instances a platinum-based agent or doxorubicin can optionally be administered simultaneously (in the same pharmaceutical composition or a separate pharmaceutical composition) with the anti-FOLR1 immunoconjugate (e.g., IMGN853). A platinum-based agent or doxorubicin can also optionally be administered simultaneously (in the same pharmaceutical composition or a separate pharmaceutical composition) with the anti-VEGF agent. A platinum-based agent or doxorubicin can also optionally be administered sequentially with the anti-FOLR1 immunoconjugate (e.g., IMGN853) and/or the anti-VEGF agent in any order.

In one instance, the immunoconjugate that binds to FOLR1 (e.g., IMGN853) and the platinum-based agent are administered simultaneously. In one instance, the anti-FOLR1 immunoconjugate (e.g., IMGN853) and the platinum-based agent are administered in separate pharmaceutical compositions. In one instance, the anti-FOLR1 immunoconjugate (e.g., IMGN853) and the platinum-based agent are administered in the same pharmaceutical composition. In one instance, the anti-FOLR1 immunoconjugate (e.g., IMGN853) and the platinum-based agent are administered sequentially. In such instances an anti-VEGF agent or doxorubicin can optionally be administered simultaneously (in the same pharmaceutical composition or a separate pharmaceutical composition) with the anti-FOLR1 immunoconjugate (e.g., IMGN853). An anti-VEGF agent or doxorubicin can also optionally be administered simultaneously (in the same pharmaceutical composition or a separate pharmaceutical composition) with the platinum-based agent. An anti-VEGF agent or doxorubicin can also optionally be administered sequentially with the anti-FOLR1 immunoconjugate (e.g., IMGN853) and/or the platinum-based agent.

In one instance, the immunoconjugate that binds to FOLR1 (e.g., IMGN853) and the doxorubicin are administered simultaneously. In one instance, the anti-FOLR1 immunoconjugate (e.g., IMGN853) and the doxorubicin are administered in separate pharmaceutical compositions. In one instance, the anti-FOLR1 immunoconjugate (e.g., IMGN853) and the doxorubicin are administered in the same pharmaceutical composition. In one instance, the anti-FOLR1 immunoconjugate (e.g., IMGN853) and the doxorubicin are administered sequentially. In such instances an anti-VEGF agent or a platinum-based agent can optionally be administered simultaneously (in the same pharmaceutical composition or a separate pharmaceutical composition) with the anti-FOLR1 immunoconjugate (e.g., IMGN853). An anti-VEGF agent or a platinum-based agent can also optionally be administered simultaneously (in the same pharmaceutical composition or a separate pharmaceutical composition) with the doxorubicin. An anti-VEGF agent or a platinum-based agent can also optionally be administered sequentially with the anti-FOLR1 immunoconjugate (e.g., IMGN853) and/or the doxorubicin.

VII. C. Assessment and Monitoring

In certain embodiments, the combination of the anti-FOLR1 immunoconjugate (e.g., IMGN853) and the anti-VEGF agent, the platinum-based agent, and/or the doxorubicin is useful for inhibiting tumor growth. In certain embodiments, the combination of the anti-FOLR1 immunoconjugate (e.g., IMGN853) and the anti-VEGF agent, the platinum-based agent, and/or the doxorubicin is useful for inducing differentiation of tumor cells. In certain embodiments, the combination of the anti-FOLR1 immunoconjugate (e.g., IMGN853) and the anti-VEGF agent, the platinum-based agent, and/or the doxorubicin is useful for reducing tumor volume.

For example, in some embodiments, treatment with a combination of a FOLR1 immunoconjugate (e.g., IMGN853) and an anti-VEGF agent, a platinum-based agent, and/or doxorubicin results in a % T/C value that is less than about 50%, less than about 45%, less than about 40%, less than about 35%, less than about 30%, less than about 25%, less than about 20%, less than about 15%, less than about 10%, or less than about 5%.

In some particular embodiments, the combination of a FOLR1 immunoconjugate (e.g., IMGN853) and an anti-VEGF agent, a platinum-based agent, and/or doxorubicin can reduce tumor size in an ovarian cancer (e.g., an epithelial ovarian cancer) and/or lung cancer xenograft model. In some particular embodiments, the combination of a FOLR1 immunoconjugate (e.g., IMGN853) and an anti-VEGF agent, a platinum-based agent, and/or doxorubicin can reduce tumor size in an ST088, OV90, and/or IGROV-1 xenograft model. In some particular embodiments, the combination of a FOLR1 immunoconjugate (e.g., IMGN853) and an anti-VEGF agent, a platinum-based agent, and/or doxorubicin can reduce tumor size in an H2110 xenograft model.

In some embodiments, the combination of a FOLR1 immunoconjugate (e.g., IMGN853) and an anti-VEGF agent, a platinum-based agent, and/or doxorubicin is capable of inhibiting metastases. In certain embodiments, the combination of a FOLR1 immunoconjugate (e.g., IMGN853) and an anti-VEGF agent, a platinum-based agent, and/or doxorubicin can reduce the tumorigenicity of a tumor. The methods of use can be in vivo methods.

In certain embodiments, the combination of a FOLR1 immunoconjugate (e.g., IMGN853) and an anti-VEGF agent, a platinum-based agent, and/or doxorubicin produces a synergistic effect. For example, the combination of anti-VEGF agent (e.g., bevacuzimab) and a FOLR1 immunoconjugate (e.g., IMGN853) can be synergistic as a result of the fact that the anti-VEGF agent (e.g., bevacuzimab) increases or potentiates IMGN853 tumor localization or activity. Thus, in some embodiments, the anti-VEGF agent (e.g., bevacuzimab) is administered prior to the administration of the FOLR1 immunoconjugate (e.g., IMGN853).

In certain embodiments, administration of the combination of a FOLR1 immunoconjugate (e.g., IMGN853) and an anti-VEGF agent, a platinum-based agent, and/or doxorubicin does not produce more toxicity than administration of the anti-VEGF agent, platinum-based agent, and/or doxorubicin. In some embodiments, administration of the combination of a FOLR1 immunoconjugate (e.g., IMGN853) and an anti-VEGF agent, a platinum-based agent, and/or doxorubicin does not produce more toxicity than administration of the anti-FOLR1 immunoconjugate. In some embodiments, administration of the combination of a FOLR1 immunoconjugate (e.g., IMGN853) and an anti-VEGF agent, a platinum-based agent, and/or doxorubicin does not produce more toxicity than administration of either the anti-FOLR1 immunoconjugate or the anti-VEGF agent, platinum-based agent, and/or doxorubicin.

Each of the above aspects can further include monitoring the subject for recurrence of the cancer. Monitoring can be accomplished, for example, by evaluating progression free survival (PFS), overall survival (OS), objective response rate (ORR) complete response (CR), partial response (PR). In one embodiment, the PFS is evaluated after initiation of treatment. In some embodiments, PFS is extended about 1 month, 1.2 months, 2 months, 2.9 months, 3 months, 3.8 months, 4 months, 6 months, 7 months, 8 months, 9 months, 1 year, about 2 years, about 3 years, etc., compared to a control. In one embodiment, the PFS is extended about 2.9 months to 3.8 months with the treatment regimen combining a FOLR1 immunoconjugate (e.g., IMGN853) and an anti-VEGF agent, a platinum-based agent, and/or doxorubicin compared to a control. In one embodiment, the PFS is extended at least about 3.8 months with the treatment regimen combining a FOLR1 immunoconjugate (e.g., IMGN853) and an anti-VEGF agent, a platinum-based agent, and/or doxorubicin compared to a control. In another embodiment, the PFS is extended about 2.3 months with the treatment regimen combining a FOLR1 immunoconjugate (e.g., IMGN853) and an anti-VEGF agent, a platinum-based agent, and/or doxorubicin compared to a control. In one embodiment, the PFS is extended about 6 months with the treatment regimen combining a FOLR1 immunoconjugate (e.g., IMGN853) and an anti-VEGF agent, a platinum-based agent, and/or doxorubicin compared to a control.

VII. D. Additional Therapies

A steroid can be administered in addition to the combination of a FOLR1 immunoconjugate (e.g., IMGN853) and an anti-VEGF agent, a platinum-based agent, and/or doxorubicin. In some embodiments, the administration of the steroid in addition to the combination of a FOLR1 immunoconjugate (e.g., IMGN853) and an anti-VEGF agent, a platinum-based agent, and/or doxorubicin results in a reduction of headaches as compared to administration of only the combination of a FOLR1 immunoconjugate (e.g., IMGN853) and an anti-VEGF agent, a platinum-based agent, and/or doxorubicin.

The steroid can be administered at the same time as the immunoconjugate, prior to the administration of the immunoconjugate, and/or after the administration of the immunoconjugate. In some embodiments, the steroid is administered within about a week, about five days, about three days, about two days, or about one day or 24 hours prior to the administration of the immunoconjugate. In some embodiments, the steroid is administered within one day of the administration of the immunoconjugate. In some embodiments, the steroid is administered multiple times. In some embodiments, the steroid is administered about one day prior to the administration of the immunoconjugate and on the same day as the administration of the immunoconjugate. The steroid can be administered via any number of ways, including for example, topical, pulmonary, oral, parenteral, or intracranial administration. In some embodiments, the administration is oral. In some embodiments, the administration is intravenous. In some embodiments, the administration is both oral and intravenous.

In some embodiments, a steroid is administered in an eye drop. In some embodiments, the eye drops are preservative-free, lubricating eye drops.

Another analgesic or other medication to prevent or treat headaches can also be administered in addition to the combination of a FOLR1 immunoconjugate (e.g., IMGN853) and an anti-VEGF agent, a platinum-based agent, and/or doxorubicin. For example, acetaminophin and/or dephenhydramine can be administered in addition to the combination of a FOLR1 immunoconjugate (e.g., IMGN853) and an anti-VEGF agent, a platinum-based agent, and/or doxorubicin. The analgesic can be administered prior to, at the same time, or after the administration of the immunoconjugate and can be via any appropriate administration route. In some embodiments, the analgesic is administered orally.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application

Example 1

Combination IMGN853+PLD Therapy is More Active than IMGN853 Monotherapy and PLD Monotherapy in the ST088 Epithelial Ovarian Cancer Tumor Model The antitumor activity of IMGN853 was evaluated as a monotherapy and in combination with pegylated liposomal doxorubicin (PLD) in female SCID mice bearing ST088 human epithelial ovarian cancer patient derived tumor xenografts. CB17 SCID mice were randomized into groups (n=8 per group) by tumor volume and subsequently dosed. The groups included a control group dosed with IMGN853 formulation buffer (vehicle) ("control" in FIG. 1), an IMGN853 single agent group dosed at 5 mg/kg once every seven days (a week) for two weeks (QWx2) ("IMGN853" in FIG. 1), a PLD single agent group dosed at 4 mg/kg QWx2 ("PLD" in FIG. 1), and an IMGN853+PLD combination group dosed at 5 mg/kg QWx2 dose of IMGN853 in combination with a 4 mg/kg QWx2 dose of PLD ("IMGN853+PLD" in FIG. 1).

Tumor volumes were measured twice weekly in three dimensions using a caliper. Body weights were measured twice per week as an index of test agent toxicity. Activity was assessed as described in Bissery et al., *Cancer Res.* 51:4845-4852 (1991). FIG. 1 depicts the results.

IMGN853 dosed at 5 mg/kg QWx2 was active as a monotherapy (T/C 31%, 0/8 partial responses (PR), and 0/8 complete responses (CR)). Further, IMGN853 monotherapy was well tolerated with no notable body weight loss observed. PLD dosed at 4 mg/kg QWx2 was also active as a monotherapy (T/C 21%, 0/8 PR, and 0/8 CRs). PLD monotherapy resulted in a median 19% body weight loss (BWL) at nadir (Day 15 post dose). The IMGN853+PLD combination was highly active and more active than the IMGN853 and PLD monotherapies (T/C 10%, 0/8 PR, and 0/8 CR). Combination therapy with IMGN853 and PLD resulted in weight loss that was comparable to the PLD monotherapy (16% at nadir). See FIG. 1. Thus, combination therapy with IMGN853 and PLD increased efficacy without increasing toxicity.

Example 2

Combination IMGN853 (5 mg/kg)+Bevacizumab Therapy is More Active than IMGN853 Monotherapy and Anti-Bevacizumab Monotherapy in the OV90 Ovarian Cancer Tumor Model The antitumor activity of IMGN853 was evaluated as a monotherapy and in combination with the anti-VEGF antibody bevacizumab in female SCID mice bearing OV90 serous ovarian tumor xenografts. Mice were randomized into groups (n=6 per group) by tumor volume and subsequently dosed on Day 14 post-inoculation. The groups included a control group that received a single dose (1x) of IMGN853 formulation buffer ("vehicle" in FIG. 2A), an IMGN853 single agent group dosed at 5 mg/kg 1x ("IMGN853" in FIG. 2A), a bevacizumab single agent group dosed at 5 mg/kg 1x ("bevacizumab" in FIG. 2A), and an IMGN853+bevacizumab combination group that received a 5 mg/kg 1x dose of IMGN853 in combination with 5 mg/kg 1x bevacizumab ("IMGN853+bevacizumab" in FIG. 2A).

Tumor volumes were measured one to two times weekly in three dimensions using a caliper. The tumor volume was expressed in mm$^3$ using the formula V=Length×Width×Height×½ (Tomayko and Reynolds, *Cancer Chemother. Pharmacol.* 24:148-54 (1989)) Body weights were measured twice per week as an index of toxicity. Activity was assessed as described in Bissery et al. (1991). FIG. 2A depicts the results.

At 5 mg/kg, single dose IMGN853 was active as a monotherapy (T/C 36%, 1/5 CR, and 0/5 tumor free survivors (TFS)). At 5 mg/kg, single dose bevacizumab was also active as a monotherapy (T/C 37%, 0/6 CRs, and 0/6 TFS). The IMGN853+bevacizumab combination (5 mg/kg of each) was highly active and more active than both the IMGN853 monotherapy and the bevacizumab monotherapy (T/C 9%, 6/6 CRs 1/6 TFS). See FIG. 2A. All treatments were well tolerated with no notable body weight loss observed in any treatment group. Thus, combination therapy with IMGN853 and bevacizumab increased efficacy without increasing toxicity.

Example 3

Combination IMGN853 (2.5 mg/kg)+Bevacizumab Therapy is More Active than IMGN853 Monotherapy and Bevacizumab Monotherapy in the OV90 Ovarian Cancer Tumor Model The antitumor activity of IMGN853 was evaluated as a monotherapy and in combination with the anti-VEGF antibody bevacizumab in female SCID mice bearing OV90 serous ovarian tumor xenografts. Mice were randomized into groups (n=6 per group) by tumor volume and subsequently dosed on Day 14 post-inoculation. The groups included a control group that received a single dose (1x) of IMGN853 formulation buffer ("vehicle" in FIG. 2B), an IMGN853 single agent group dosed at 2.5 mg/kg 1x ("IMGN853" in FIG. 2B), a bevacizumab single agent group dosed at 5 mg/kg 1x ("bevacizumab" in FIG. 2B), and an IMGN853+bevacizumab combination group that received a 2.5 mg/kg 1x dose of IMGN853 in combination with a 5 mg/kg 1x bevacizumab at ("IMGN853+bevacizumab" in FIG. 2B).

Tumor volumes were measured one to two times weekly in three dimensions using a caliper. The tumor volume was expressed in mm$^3$ using the formula V=Length×Width×Height×½ (Tomayko 1989). Body weights were measured twice per week as an index of toxicity. Activity was assessed as described in Bissery et al. (1991). FIG. 2B depicts the results.

Figure 3:
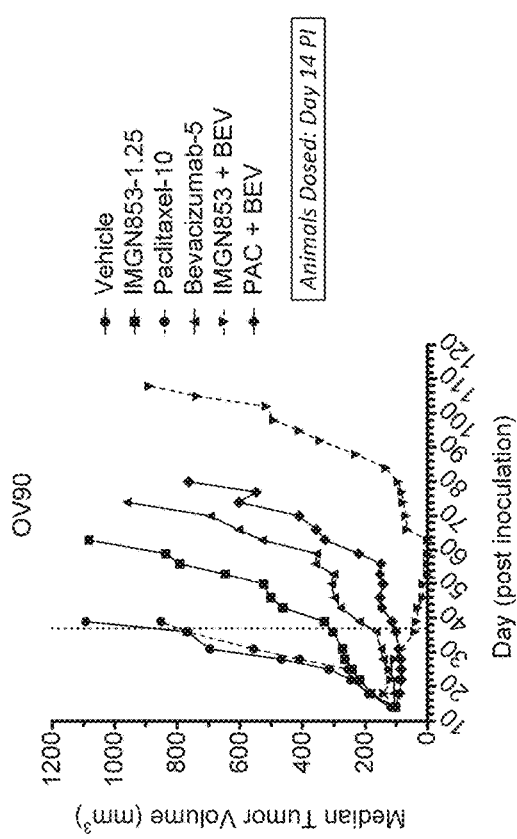
FIG. 3 shows the antitumor activity of IMGN853 (1.25 mg/kg), paclitaxel (10 mg/kg), bevacizumab (5 mg/kg), IMGN853+bevacizumab combination therapy, and paclitaxel+bevacizumab combination therapy in a serous ovarian cancer tumor model.

At 2.5 mg/kg, single dose IMGN853 was active as a monotherapy (T/C 36%, 0/6 CR, and 0/6 TFS). At 5.0 mg/kg, single dose bevacizumab was active (T/C 31%, 0/6 CR, and 0/6 TFS). As a monotherapy, bevacizumab displayed comparable antitumor activity relative to IMGN853 at these dose levels; however neither agent induced sustained tumor growth inhibition or tumor regression. In stark contrast, the combination of IMGN853 plus bevacizumab resulted in robust tumor regression in all animals (FIG. 2B). The IMGN853+bevacizumab combination (2.5 mg/kg IMNG853+5 mg/kg of bevacizumab) was more active than both the IMGN853 monotherapy and the bevacizumab monotherapy (T/C 17%, 6/6 CR, and 0/6 TFS). See FIG. 2B. Notably, a similar combinatorial benefit was achieved when the dose of IMGN853 was further reduced to 1.25 mg/kg (FIG. 3). All treatments were well tolerated with no notable body weight loss observed in any treatment group. Thus, combination therapy with IMGN853 and bevacizumab increased efficacy without increasing toxicity.

Figure 11B:
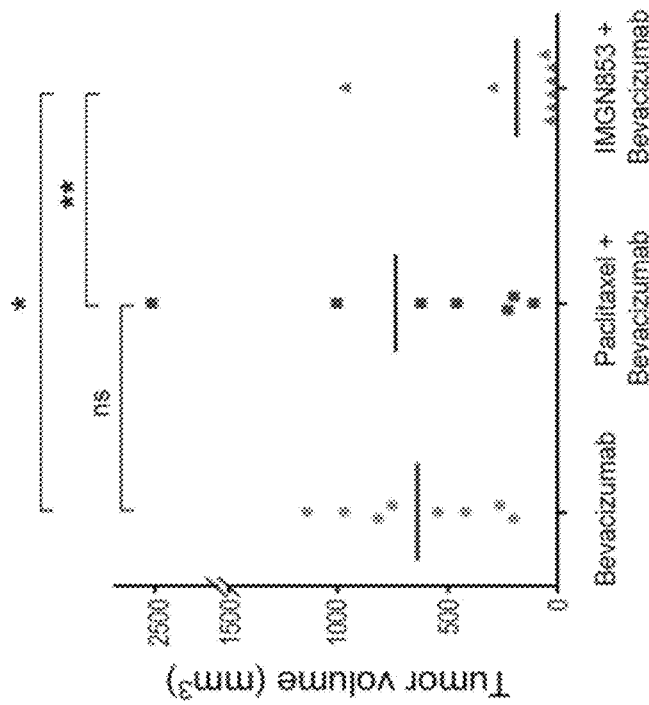
FIG. 11B shows tumor volumes measured at the end of study and individual tumor sizes plotted according to treatment group in mice bearing platinum-resistant ovarian cancer PDXs receiving two consecutive weekly doses of bevacizumab (5 mg/kg), alone or in combination with either paclitaxel (10 mg/kg) or IMGN853 (5 mg/kg). Tumor growth was monitored out to 102 days. * P=0.011; ** P=0.018; ns, not significant (Wilcoxon test, non-adjusted).
Figure 11A:
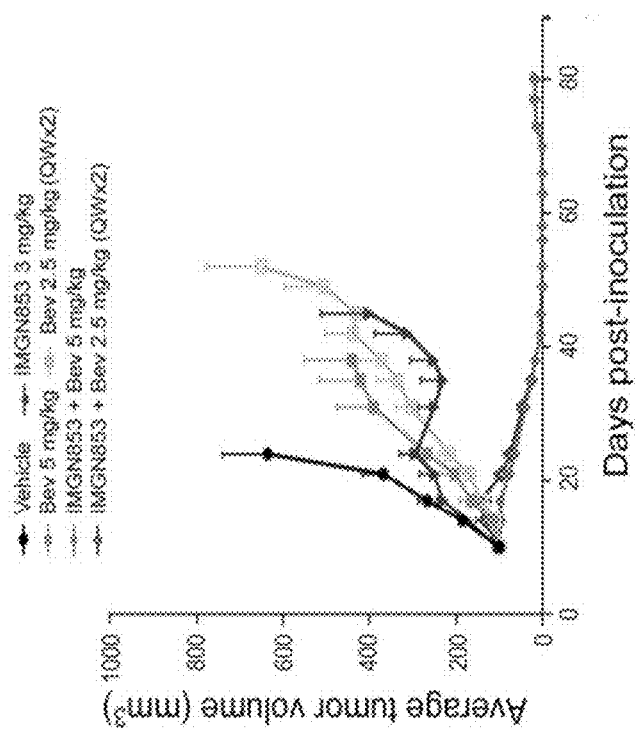
FIG. 11A shows the antitumor activity of IMGN853 (3 mg/kg) alone or in combination with bevacizumab, administered either as a single 5 mg/kg dose, or two consecutive weekly doses of 2.5 mg/kg (QWx2) in mice bearing established OV-90 xenografts (n=7 mice/group).

Next, the effects of fractionated bevacizumab dosing were examined whereby animals were administered bevacizumab as either a single 5 mg/kg dose or two 2.5 mg/kg doses (QWx2), both as monotherapy and in combination with 3 mg/kg IMGN853 (FIG. 11A). Split-dosing had no effect on bevacizumab efficacy, and similar (moderate) growth suppressive effects were seen following treatment with single agent IMGN853. Exposure to both combination regimens resulted in rapid tumor stabilization and dramatic regressions (up to 38% within 10 days of treatment), particularly in the IMGN853 plus 5 mg/kg bevacizumab cohort where doublet therapy was curative for all seven animals (FIG. 11A). Once again, combination IMGN853 and bevacizumab treatments were well tolerated.

Finally, the efficacy of IMGN853 was evaluated in combination with bevacizumab in the same platinum-resistant PDX model shown in FIG. 11B. Unlike the moderate activity seen with IMGN853 monotherapy, single agent bevacizumab exposure (5 mg/kg, dosed QWx2) resulted in prolonged growth control of these aggressive tumors (data not shown), although no CRs were observed over the course of a 102-day study. In agreement with the OV-90 results, the combination of IMGN853 and bevacizumab (both 5 mg/kg, QWx2) outperformed either single agent modality and induced tumor regressions in all mice. CRs were seen in 7/8 animals. Indeed, analysis of end-of-study tumor volumes revealed a significant reduction in tumor burden in the combination-treated group compared to bevacizumab-treated animals alone (FIG. 11B). Moreover, this effect was not recapitulated in animals that were treated with a combination of bevacizumab and paclitaxel (10 mg/kg), suggesting that the therapeutic benefit conferred by the addition of IMGN853 to the antiangiogenic agent is functionally specific for the ADC molecule.

Example 4

Combination IMGN853 (1.25 mg/kg)+Bevacizumab Therapy is More Active than IMGN853 Monotherapy, Bevacizumab Monotherapy, and Combination Bevacizumab+Paclitaxel Therapy in the OV90 Ovarian Cancer Tumor Model The antitumor activity of IMGN853 was evaluated in combination with bevacizumab in female SCID mice bearing OV90 serous ovarian tumor xenografts. Mice were randomized into groups (n=8 per group) by tumor volume and subsequently dosed on Day 14 post-inoculation. All treatments consisted of single doses (1×). The groups included a control group dosed with IMGN853 formulation buffer ("vehicle" in FIG. 3), an IMGN853 single agent group dosed at 1.25 mg/kg 1× ("IMGN853-1.25" in FIG. 3), a paclitaxel single agent group dosed at 10 mg/kg 1× ("Paclitaxel-10" in FIG. 3), a bevacizumab single agent group dosed at 5 mg/kg 1× ("Bevacizumab-5" in FIG. 3), an IMGN853+bevacizumab combination group dosed at 1.25 mg/kg 1× and 5 mg/kg 1×, respectively, ("IMGN853+BEV" in FIG. 3), and a paclitaxel+bevacizumab combination group dosed at 10 mg/kg 1× and 5 mg/kg 1×, respectively, ("PAC+BEV" in FIG. 3).

Tumor volumes were measured one to two times weekly in three dimensions using a caliper. The tumor volume was expressed in mm3 using the formula V=Length×Width×Height×½ (Tomayko 1989). Body weights were measured twice per week as an index of toxicity. Activity was assessed as described in Bissery et al. (1991). FIG. 3 depicts the results.

At 1.25 mg/kg, single dose IMGN853 was active as a monotherapy (T/C 37%, 0/7 CR, and 0/7 TFS). Paclitaxel single agent was inactive (T/C 94%, 0/6 CR, and 0/6 TFS). A single dose of bevacizumab was active (T/C 22%, 0/8 CR, and 0/8 TFS). The paclitaxel+bevacizumab combination was active (T/C 12%, 0/8 CR, and 0/8 TFS). The IMGN853+bevacizumab combination was highly active and more active than all single agent treatments as well as the paclitaxel+bevacizumab combination treatment (T/C 5%, 5/8 CR, and 0/8 TFS). See FIG. 3. All treatments were well tolerated. Thus, the combination of bevacizumab with IMGN853 was more effective than the combination of bevacizumab with another therapy.

Example 5

Combination IMGN853+Bevacizumab Therapy is More Active than IMGN853 Monotherapy and Bevacizumab Monotherapy in the IGROV-1 Epithelial Ovarian Tumor Model The antitumor activity of IMGN853 was evaluated as a monotherapy and in combination with bevacizumab in female SCID mice bearing IGROV-1 ovarian tumor xenografts. Mice were randomized into groups (n=6 per group) by tumor volume and subsequently dosed on Day 14 post-inoculation. All treatments consisted of single doses (1×). The groups included a control group dosed with IMGN853 formulation buffer ("vehicle" in FIG. 4), an IMGN853 single agent group dosed at 5 mg/kg 1× ("IMGN853-5" in FIG. 4), a bevacizumab single agent group dosed at 5 mg/kg 1× ("Bevacizumab-5" in FIG. 4), and an IMGN853+bevacizumab combination group dosed with 5 mg/kg of IMGN853 and 5 mg/kg of bevacizumab ("IMGN853+BEV" in FIG. 4).

Figure 4:
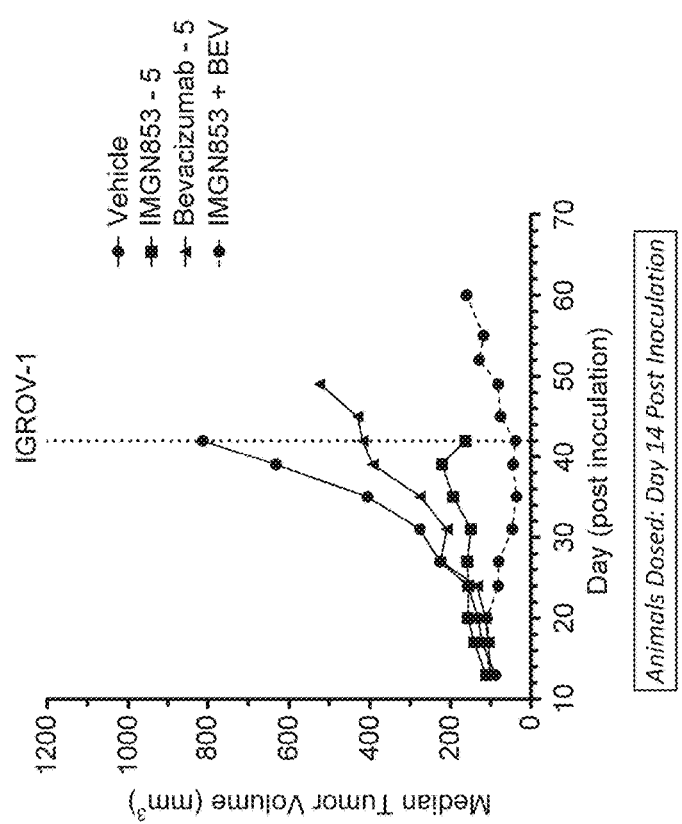
FIG. 4 shows the antitumor activity of IMGN853 (5 mg/kg), bevacizumab (5 mg/kg), and IMGN853+bevacizumab combination therapy in an epithelial ovarian cancer tumor model.

Tumor volumes were measured one to two times weekly in three dimensions using a caliper. The tumor volume was expressed in mm$^3$ using the formula V=Length×Width×Height×½ (Tomayko 1989). Body weights were measured twice per week as an index of toxicity. Activity was assessed as described in Bissery et al. (1991). FIG. 4 depicts the results.

IMGN853 was active as a monotherapy (T/C 20%, 0/4 CR, and 0/4 TFS). Bevacizumab was inactive as a monotherapy (T/C 51%, 0/4 CR, and 0/4 TFS). The IMGN853+bevacizumab combination therapy was highly active and more active than IMGN853 and bevacizumab monotherapies (T/C 5%, 3/6 CR, and 0/6 TFS). See FIG. 4. All treatments were well tolerated with no notable body weight loss observed in any treatment group. Thus, combination therapy with IMGN853 and bevacizumab increased efficacy without increasing toxicity.

Example 6

Combination IMGN853+Bevacizumab Therapy is More Active than IMGN853 Monotherapy, Bevacizumab Monotherapy, and Combination Paclitaxel+Bevacizumab Therapy in the ST088 Epithelial Ovarian Cancer Tumor Model The antitumor activity of IMGN853 was evaluated as a monotherapy and in combination with bevacizumab in female SCID mice bearing ST088 human epithelial ovarian cancer (EOC) patient-derived tumor xenografts. CB17 SCID mice were randomized into groups (n=8 per group) by tumor volume and subsequently dosed. The groups included a control group dosed with IMGN853 formulation buffer (vehicle) ("control" in FIG. 5), an IMGN853 single agent group dosed at 5 mg/kg QWx2 ("IMGN853" in FIG. 5), a bevacizumab single agent group dosed at 5 mg/kg QWx2 ("Bev" in FIG. 5), and an IMGN853+bevacizumab combination group dosed at 5 mg/kg QWx2 of IMGN853 and 5 mg/kg QWx2 of bevacizumab ("IMGN853+Bev" in FIG. 5).

For comparison, another group of mice was dosed with paclitaxel at 10 mg/kg QWx2 and an additional group of mice was dosed with paclitaxel 10 mg/kg QWx2 in combination with bevacizumab at 5 mg/kg QWx2.

Figure 5:
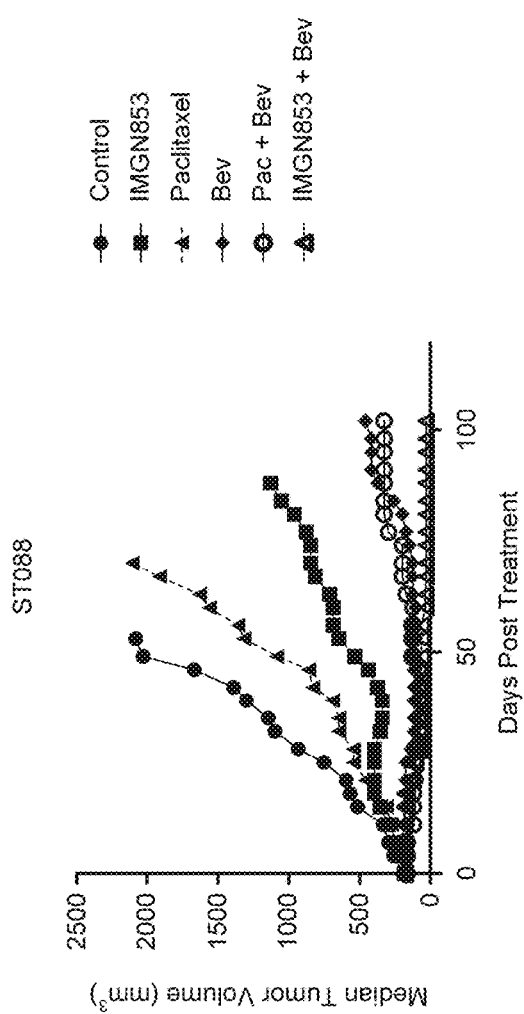
FIG. 5 shows the antitumor activity of IMGN853 (5 mg/kg), paclitaxel (10 mg/kg), bevacizumab (5 mg/kg), paclitaxel+bevacizumab combination therapy, and IMGN853+bevacizumab combination therapy in an epithelial ovarian cancer tumor model.

Tumor volumes were measured twice weekly in three dimensions using a caliper. Body weights were measured twice per week as an index of toxicity. Activity was assessed as described in Bissery et al. (1991). FIG. 5 depicts the results.

IMGN853 dosed at 5 mg/kg QWx2 was active as a monotherapy (T/C 31%) with no regressions (0/8 PR and 0/8 CR). Bevacizumab dosed at 5 mg/kg QWx2 was highly active as a monotherapy (T/C 6%); however, there were no regressions (0/8 PR and 0/8 CR). Paclitaxel dosed at 10 mg/kg QWx2 was inactive (T/C 71%, 0/8 PR, and 0/8 CR). The combination therapy of paclitaxel+bevacizumab was highly active (T/C 6%, 6/8 PR, and 0/8 CR). The combination therapy of IMGN853+bevacizumab was also highly active (T/C 3%, 7/8 PR, and 0/8 CRs). The median tumor volume for the group treated with the combination of IMGN853+bevacizumab was smaller than the median tumor volume for the group treated with the combination of paclitaxel+bevacizumab at the last day of the study (Day 109 post dosing 37 vs. 463 mm$^3$, respectively). See FIG. 5. All treatments were well tolerated with no notable body weight loss observed in any treatment group.

Example 7

Combination IMGN853+Bevacizumab Therapy is More Active than IMGN853 Monotherapy and Bevacizumab Monotherapy in the H2110 Non-Small Cell Lung Cancer Tumor Model The antitumor activity of IMGN853 was evaluated as a monotherapy and in combination with bevacizumab in female SCID mice bearing H2110 non-small cell lung cancer (NSCLC) tumor xenografts. Mice were randomized into groups (n=6-10 per group) by tumor volume and subsequently dosed on Day 7 post-inoculation. All treatments consisted of single doses (1×). The groups included a control group dosed with IMGN853 formulation buffer ("vehicle" in FIG. 6), an IMGN853 single agent group dosed at 3 mg/kg ("IMGN853 3 mg/kg" in FIG. 6), an IMGN853 single agent group dosed at 1.5 mg/kg ("IMGN853 1.5 mg/kg" in FIG. 6), a bevacizumab single agent group dosed at 5 mg/kg ("Bevacizumab 5 mg/kg" in FIG. 6), an IMGN853+bevacizumab combination group dosed at 5 mg/kg of bevacizumab and 3 mg/kg of IMGN853 ("IMGN853 3 mg/kg+Bev 5 mg/kg" in FIG. 6), and an IMGN853+bevacizumab combination group dosed at 5 mg/kg of bevacizumab and 1.5 mg/kg of IMGN853 ("IMGN853 1.5 mg/kg+Bev 5 mg/kg" in FIG. 6).

Figure 6:
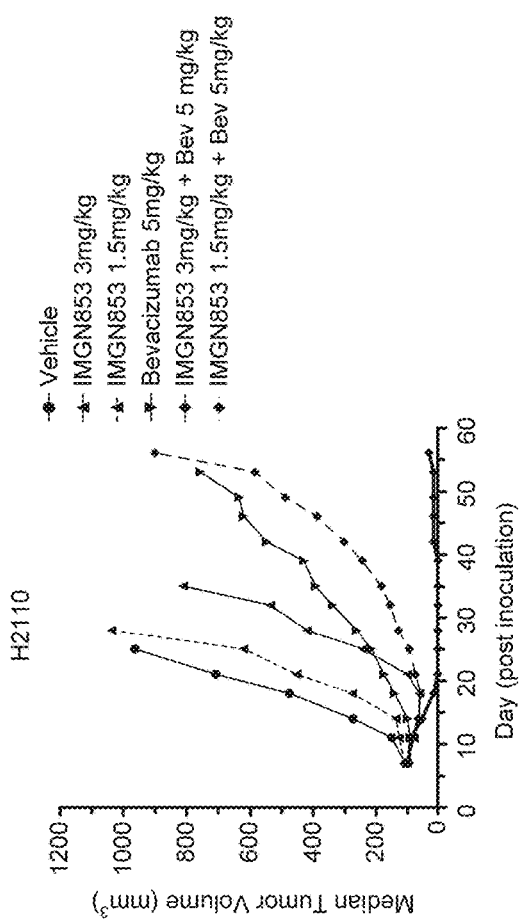
FIG. 6 shows the antitumor activity of IMGN853 (3 mg/kg), IMGN853 (1.5 mg/kg), bevacizumab (5 mg/kg), IMGN853 (3 mg/kg)+bevacizumab combination therapy, and IMGN853 (1.5 mg/kg)+bevacizumab combination therapy in a non-small cell lung cancer tumor model.

Tumor volumes were measured one to two times weekly in three dimensions using a caliper. The tumor volume was expressed in mm$^3$ using the formula V=Length×Width×Height×½ (Tomayko 1989). Body weights were measured twice per week as an index of test agent toxicity. Activity was assessed as described in Bissery et al. (1991). FIG. 6 depicts the results.

IMGN853 was active as a monotherapy at 3 mg/kg 1× (T/C 25%, 2/6 PR, 0/6 CR, and 0/6 TFS), but inactive at 1.5 mg/kg 1× (T/C 64%, 1/6 PR, 0/6 CR, and 0/6 TFS). Single dose bevacizumab at 5 mg/kg 1× was also active as a monotherapy (T/C 22%, 0/6 PR, 0/6 CR, and 0/6 TFS). The combination of IMGN853 at 3 mg/kg 1×+bevacizumab at 5 mg/kg 1× was highly active (T/C 0%, 10/10 PR, 6/10 CR, and 4/10 TFS). The combination of IMGN853 at 1.5 mg/kg 1×+bevacizumab at 5 mg/kg 1× was also highly active (T/C 9%, 3/10 PR, 1/10 CR, and 0/10 TFS). Notable body weight loss was observed. Because the vehicle treated group experienced an 11% drop from baseline weight by Day 25 post-inoculation, it is believed that the body weight loss was disease-associated. The IMGN853 3 mg/kg monotherapy group experienced a 9% body weight loss on Day 42 post-inoculation, while the IMGN853 1.5 mg/kg monotherapy group experienced an 8% body weight loss on Day 25 post-inoculation. The bevacizumab monotherapy group had a 9% body weight loss on Day 49 post-inoculation. See FIG. 6. The IMGN853+bevacizumab combination therapies were well tolerated with no notable body weight loss observed. Thus, combination therapy with IMGN853 and bevacizumab increased efficacy while decreasing toxicity.

Example 8

Combination IMGN853+Carboplatin Therapy is More Active than Combination Paclitaxel+Carboplatin Therapy in the OV90 Ovarian Cancer Tumor Model The antitumor activity of IMGN853 was evaluated as a combination therapy with carboplatin and as a triple-combination therapy with both carboplatin and bevacizumab in female SCID mice bearing OV90 ovarian tumor xenografts. Mice were randomized into groups (n=6 per group) by tumor volume and subsequently dosed on Day 14 post-inoculation. All treatments consisted of single doses (1×). The groups included a control group dosed with IMGN853 formulation buffer ("vehicle" in FIG. 7), an IMGN853+carboplatin combination group dosed at 5 mg/kg 1× and 100 mg/kg 1×, respectively, ("CARBO+IMGN853" in FIG. 7), an IMGN853+carboplatin+bevacizumab triple-combination group dosed at 5 mg/kg 1×, 100 mg/kg 1×, and 5 mg/kg 1×, respectively, ("CARBO+IMGN853+Bev" in FIG. 7), a paclitaxel+carboplatin combination group dosed at 10 mg/kg 1× and 100 mg/kg 1×, respectively, ("CARBO+PAC" in FIG. 7), and a paclitaxel+carboplatin+bevacizumab triple-combination group dosed at 10 mg/kg 1×, 100 mg/kg 1×, and 5 mg/kg 1×, respectively, ("CARBO+PAC+Bev" in FIG. 7).

Figure 7:
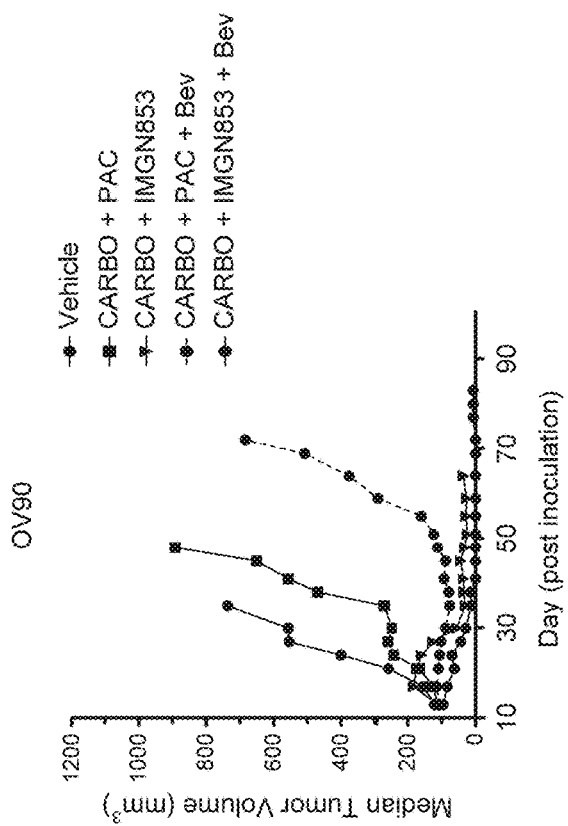
FIG. 7 shows the antitumor activity of IMGN853 (5 mg/kg)+carboplatin (100 mg/kg) combination therapy, IMGN853 (5 mg/kg)+carboplatin (100 mg/kg)+bevacizumab (5 mg/kg) triple-combination therapy, paclitaxel (10 mg/kg)+carboplatin (100 mg/kg) combination therapy, and paclitaxel (100 mg/kg)+carboplatin (100 mg/kg)+bevacizumab (5 mg/kg) triple-combination therapy in a non-small cell lung cancer tumor model.

Tumor volumes were measured one to two times weekly in three dimensions using a caliper. The tumor volume was expressed in mm³ using the formula V=Length×Width×Height×½ (Tomayko 1989). Body weights were measured twice per week as an index of toxicity. Activity was assessed as described in Bissery et al. (1991). FIG. 7 depicts the results.

The combination of IMGN853+carboplatin was highly active (T/C 10%, 3/6 CR, and 0/6 TFS). The combination of paclitaxel+carboplatin was inactive (45% T/C, 0/6 CR, and 0/6 TFS). The triple-combination of IMGN853+carboplatin+bevacizumab was highly active (5% T/C, 6/6 CR, and 0/6 TFS). The triple combination therapy of paclitaxel+carboplatin+bevacizumab was active (16% T/C, 1/6 CR, and 0/6 TFS). The combination therapy of IMGN853+carboplatin and the triple-combination of IMGN853+carboplatin+bevacizumab were more active than their paclitaxel containing equivalent combination regimens (i.e., more active than paclitaxel+carboplatin and than paclitaxel+carboplatin+bevacizumab). See FIG. 7.

The triple-combination of paclitaxel+carboplatin+bevacizumab resulted in appreciably more body weight loss (BWL) at nadir (6.9%) compared to the triple-combination of IMGN853+carboplatin+bevacizumab (2.9% BWL). BWL at nadir of the IMGN853+carboplatin combination (12.9%) was comparable to the BWL at nadir of the paclitaxel+carboplatin treatment (11.1%). Thus, triple-combination therapy with IMGN853, carboplatin and bevacizumab increased efficacy while decreasing toxicity as compared to triple-combination therapy with paclitaxel, carboplatin and bevacizumab.

Example 9

Combination IMGN853+Cediranib Therapy is More Active than IMGN853 Monotherapy and Cediranib Monotherapy in the OV90 Ovarian Tumor Model The antitumor activity of IMGN853 was evaluated in combination with the anti-VEGF agent cediranib in female SCID mice bearing OV90 serous ovarian tumor xenografts. Mice were randomized into groups (n=6 per group) by tumor volume and subsequently dosed on Day 14 post-inoculation. The groups included a control group dosed with IMGN853 formulation buffer ("Vehicle" in FIG. 8), an IMGN853 single agent group dosed at 2.5 mg/kg 1× ("IMGN853 2.5 mg/kg" in FIG. 8), a cediranib single agent group dosed at 1.5 mg/kg once a day for five days (qd×5) ("Cediranib 1.5 mg/kg qd×5" in FIG. 8), and an IMGN853+cediranib combination therapy group dosed at 2.5 mg/kg 1×IMGN853 and 1.5 mg/kg qd×5 cediranib ("IMGN853+Cediranib" in FIG. 8).

Figure 8:
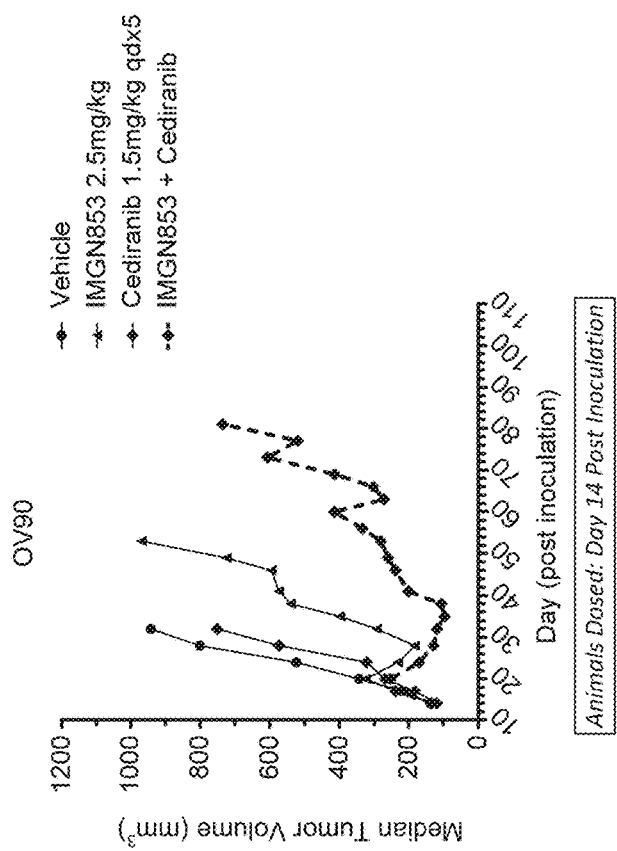
FIG. 8 shows the antitumor activity of IMGN853 (2.5 mg/kg), cediranib (1.5 mg/kg), and IMGN853+cediranib combination therapy in a serous ovarian cancer tumor model.

Tumor volumes were measured one to two times weekly in three dimensions using a caliper. The tumor volume was expressed in mm³ using the formula V=Length×Width×Height×½ (Tomayko 1989). Body weights were measured twice per week as an index of test agent toxicity. Activity was assessed as described in Bissery et al. (1991). FIG. 8 depicts the results.

IMGN853 monotherapy was active (T/C 31%, T–C 13 days, LCK 0.5, and 0/6 PR). Cediranib monotherapy was inactive (T/C 80%, T–C 4 days, LCK 0.1, and 0/6 PR). The combination of IMGN853+cediranib was active (T/C 13% with 1/6 PRs), but the T–C (47) and LCK (1.7) were greater than either IMGN853 or cediranib monotherapies. See FIG. 8. All therapies were well tolerated with minimal body weight loss observed.

Example 10

Clinical Study to Assess Combinations of IMGN853 with Bevacizumab, Carboplatin, and/or Doxorubicin The results from preclinical studies assessing the activity of IMGN853 as a single agent and the activity of IMGN853 in combination with bevacizumab, carboplatin, or PLD in ovarian cancer xenograft models described above indicated that IMGN853 in combination with bevacizumab, carboplatin, and/or PLD are promising regimens to evaluate in clinical trials of epithelial ovarian cancer (EOC), both in the relapsed and upfront setting.

A phase 1b clinical study assessing doublet combinations of IMGN853 with bevacizumab, carboplatin, and/or PLD in patients with FRα-positive ovarian cancer is conducted. The study includes two components: a dose finding component to determine the maximum tolerated dose (MTD) and recommended dosing for the combination of IMGN853+bevacizumab, IMGN853+carboplatin, and IMGN853+PLD; and a dose expansion component. In the dose expansion component, two expansion cohorts are evaluated: (1) the combination of IMGN853+bevacizumab in patients who have not received prior treatment with bevacizumab ("bevacizumab naive") and (2) the combination of IMGN853+bevacizumab in patients who have received prior treatment with bevacizumab. Additional possible cohorts include: (1) the combination of IMGN853+carboplatin in patients who have not received prior treatment with bevacizumab ("bevacizumab naive"), (2) the combination of IMGN853+PLD in patients who have not received prior treatment with bevacizumab ("bevacizumab naïve"), (3) the triple combination of IMGN853+bevacizumab+PLD in patients who have not received prior treatment with bevacizumab ("bevacizumab naive"), or (4) the triple combination of IMGN853+bevacizumab+carboplatin in patients who have not received prior treatment with bevacizumab ("bevacizumab naive"); (5) the combination of IMGN853+carboplatin in patients who have received prior treatment with bevacizumab, (6) the combination of IMGN853+PLD in patients who have received prior treatment with bevacizumab, (7) the triple combination of IMGN853+bevacizumab+PLD in patients who have received prior treatment with bevacizumab, or (8) the triple combination of IMGN853+bevacizumab+carboplatin in patients who have received prior treatment with bevacizumab; (9) the triple combination of IMGN853+bevacizumab+carboplatin; and/or (10) the triple combination of IMGN853+bevacizumab+PLD. Responses to the combination therapy are assessed using RECIST and Gynecologic Cancer Intergroup (GCIG) criteria (where appropriate).

Example 11

Combination of IMGN853 with Carboplatin Promotes Synergistic Growth Inhibitory Effects and Cell Cycle Perturbations In Vitro, and IMGN853 Potentiates the Antitumor Activity of Carboplatin In Vivo Carboplatin in combination with paclitaxel has represented the chemotherapeutic standard of care for EOC patients in the first-line adjuvant setting. To test whether IMGN853 co-treatment could improve the activity of carboplatin in EOC, the combinatorial effects of IMGN853 and carboplatin exposure in inhibiting growth of the platinum-sensitive ovarian carcinoma cell line IGROV-1 was evaluated. IGROV-1 cells were treated in vitro with increasing concentrations of IMGN853, carboplatin, or both, and combinatorial activity was assessed using Median Effect analysis (FIG. 9A). The combination was synergistic, indicating that IMGN853 augmented the effects of the platinum compound in these ovarian tumor cells.

Cell cycle analysis revealed that carboplatin exposure resulted in an accumulation of IGROV-1 cells in both the S and G2/M phases (FIG. 9B), effects previously reported to precede cell death induced by this agent in ovarian line. Treatment with IMGN853 alone resulted in an enrichment of cells in G2/M, in accordance with the well-established anti-mitotic activity of maytansinoids. Consistent with these results, co-treatment with both agents resulted in almost half of all viable cells accumulating in G2/M. Expression changes in the phosphorylated form of histone H2AX (γH2AX), a sensitive indicator of DNA damage that occurs in response to alkylating agents or as a result of mitotic catastrophe, was also examined. Single agent IMGN853 treatment induced γH2AX expression in IGROV-1 cells and to levels higher than those seen following carboplatin exposure alone. Combination treatment augmented the degree of γH2AX upregulation, indicative of enhanced DNA damage and consistent with a catastrophic phenotype (FIG. 9C).

To examine whether these in vitro cellular effects translated to improved efficacy in vivo, mice bearing patient-derived xenografts (PDX) obtained from an individual with EOC were treated with IMGN853 and carboplatin, both as single agents and in combination (FIG. 9D). It was previously determined that IMGN853 exhibited robust single agent activity in this platinum-sensitive PDX model (data not shown); therefore a suboptimal dose of IMGN853 was selected in order to permit evaluation of potential combinatorial improvements in efficacy. Animals received a single administration of IMGN853 (2.5 mg/kg) or carboplatin (80 mg/kg), and each regimen inhibited tumor growth as monotherapy (T/C values of 43% and 20% on day 39, respectively). Consistent with the in vitro findings above, concurrent treatment with both agents resulted in a substantial enhancement of antitumor activity, inhibiting tumor growth by 97% (i.e. T/C value 3%) at the same time point. Importantly, the combination of IMGN853 with platinum-based therapy was well tolerated, with no toxicity or loss of body weights seen over the course of the study.

The combinatorial benefit conferred by IMGN853/carboplatin treatment was compared with clinically relevant chemotherapeutic combinations in the same PDX model. Tumor-bearing animals received two consecutive weekly doses (QWx2) of carboplatin (80 mg/kg, i.p.) in combination with i.v. paclitaxel (10 mg/kg), PLD (4 mg/kg), or IMGN853 (5 mg/kg). As expected, treatment with the carboplatin-paclitaxel doublet was efficacious in this model of platinum sensitivity (FIG. 9E). Combination carboplatin and PLD treatment, commonly indicated in the platinum-sensitive recurrence setting, was also active in suppressing tumor growth. Notably, IMGN853 plus carboplatin combination therapy induced the greatest degree of tumor growth inhibition, including complete regressions (CR) in 6 of 7 tumor-bearing mice. In contrast, only 2 CRs were seen with the carboplatin/PLD combination, and none were observed in the carboplatin/paclitaxel-treated group. The carboplatin-paclitaxel doublet was well tolerated in this model, although some delayed toxicity was observed in animals from the PLD/carboplatin and IMGN853/carboplatin treated groups (data not shown). The higher incidence of CRs was strongly indicative of a better durability of response for the combination, and overall the data further supports the combination of IMGN853 with carboplatin for improving response to platinum therapy in EOC.

Example 12

Figure 10A:
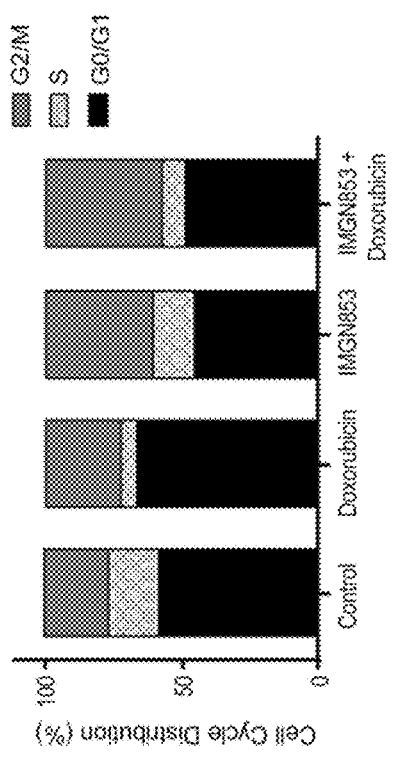
FIG. 10A shows IGROV-1 cells treated with increasing concentrations of IMGN853, doxorubicin, or both, and the effects on proliferation. The Combination Index (CI) was calculated using Median Effect analysis. Data from 3 independent experiments are shown, with points below the dotted line representing synergy between the drug pair.

Combination IMGN853 and PLD Treatment Results in Superior Therapeutic Activity in Platinum-Resistant PDX Tumors In clinical practice, PLD is a widely used second-line treatment for recurrent and/or platinum-resistant EOC, with this treatment showing superior tolerability to doxorubicin. Similar to what was observed with carboplatin, the combination of IMGN853 and doxorubicin was synergistic with respect to in vitro antiproliferative activity in the IGROV-1 cell line (FIG. 10A) and resulted in a more pronounced S plus G2/M cell cycle delay (FIG. 10B).

Figure 10C:
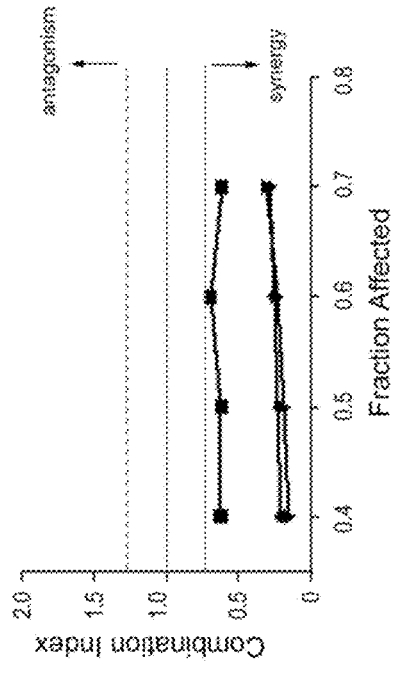
FIG. 10C shows the antitumor activity of two consecutive weekly doses of IMGN853 (5 mg/kg) and PLD (4 mg/kg) alone or in combination (n=8 mice/group) in platinum-resistant ovarian cancer PDXs established in SCID mice. Data are expressed as mean and SEM for each time point.
Figure 10B:
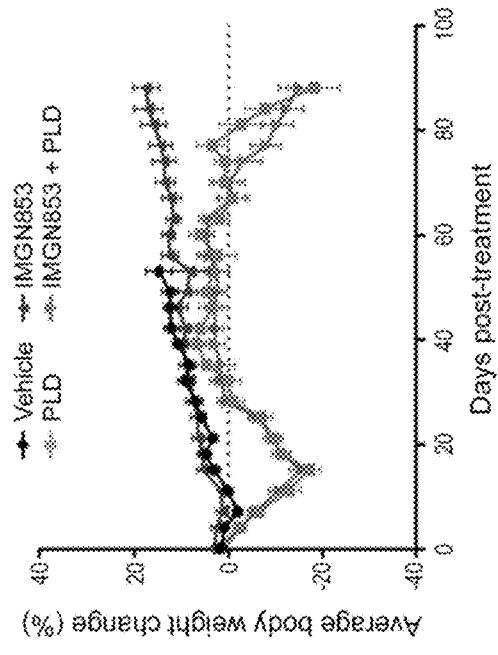
FIG. 10B shows IGROV-1 cells treated with doxorubicin (200 nM) or IMGN853 (8 nM), both alone and in combination, for 6 hours. Cells were washed, and the cell cycle distribution was determined following 24 hour culture in drug-free medium.
Figure 10D:
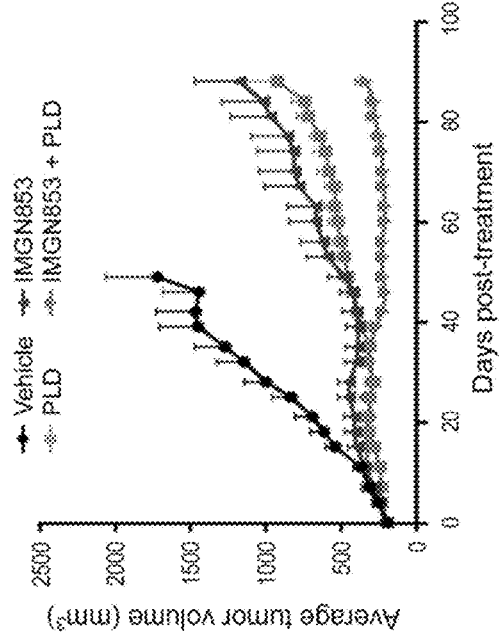
FIG. 10D shows body weights in mice measured twice weekly. Mean values are plotted against vehicle controls.

To extend the in vitro observations, the combination of IMGN853 and PLD was examined in a platinum-resistant EOC PDX model (FIG. 10C). Vehicle-treated animals progressed quickly and were removed from study when tumors reached volumes between 1500-2000 $mm^3$. QWx2 dosing of IMGN853 (5 mg/kg) inhibited tumor growth by 81% on day 49, and a similar degree of inhibition (83%) was seen when PLD (4 mg/kg) was administered on the same schedule. Even at these efficacious dose levels, combination treatment resulted in an improved and sustained antitumor response, completely abrogating tumor growth in this aggressive model of EOC. Importantly, all regimens were well tolerated, and the addition of IMGN853 to PLD conferred no additional toxicity or changes in body weight compared to PLD treatment alone (FIG. 10D). Thus, within the context of platinum-resistant disease, the combination of IMGN853 with PLD resulted in superior, durable efficacy compared to the single-agent activity of either compound alone.

This study further supports the finding that the synergistic improvements in antitumor activity seen with the IMGN85/PLD combination in vitro translate to improved and durable efficacy over the respective single-agent treatments and, importantly, exhibited good tolerability in a platinum-resistant PDX model. Combinatorial benefit has previously been reported for PLD with another FRα-targeting compound, vintafolide, in preclinical EOC models, which prompted late stage clinical evaluations of that combination in subsequent phase II and III human trials. Without wishing to be bound by theory, IMGN853 possesses a broader spectrum of bioactivity relative to vintafolid, including a more potent payload, longer circulation time, and "bystander cytotoxicity," i.e., the ability to eradicate adjacent FRα-negative or low-expressing tumor cells, and thus the findings provide a compelling rationale for the combination of IMGN853 and PLD in EOC patients with recurrent disease.

Example 13

Figure 12B:
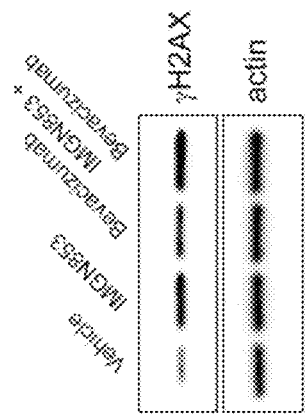
FIG. 12B shows tumor extracts immunoblotted for γH2AX or actin (loading control) as indicated.
Figure 12A:
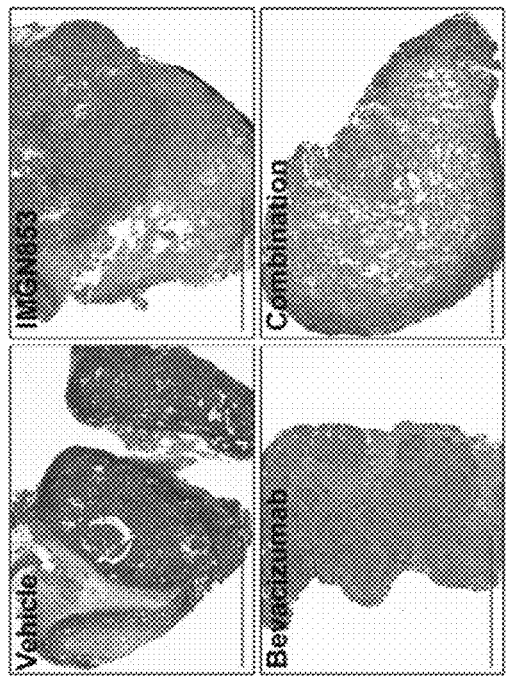
FIG. 12A shows OV-90 tumor-bearing mice treated with a single dose of vehicle, IMGN853 (2.5 mg/kg), bevacizumab (5 mg/kg), or IMGN853 plus bevacizumab and tumors harvested 4 days later. Histological staining (H&E) revealed the presence of large, central necrotic zones in tumors from combination-treated mice. Original magnification, 4×; scale bars, 2 mm (for Combination panel, 600 µm).
Figure 12C:
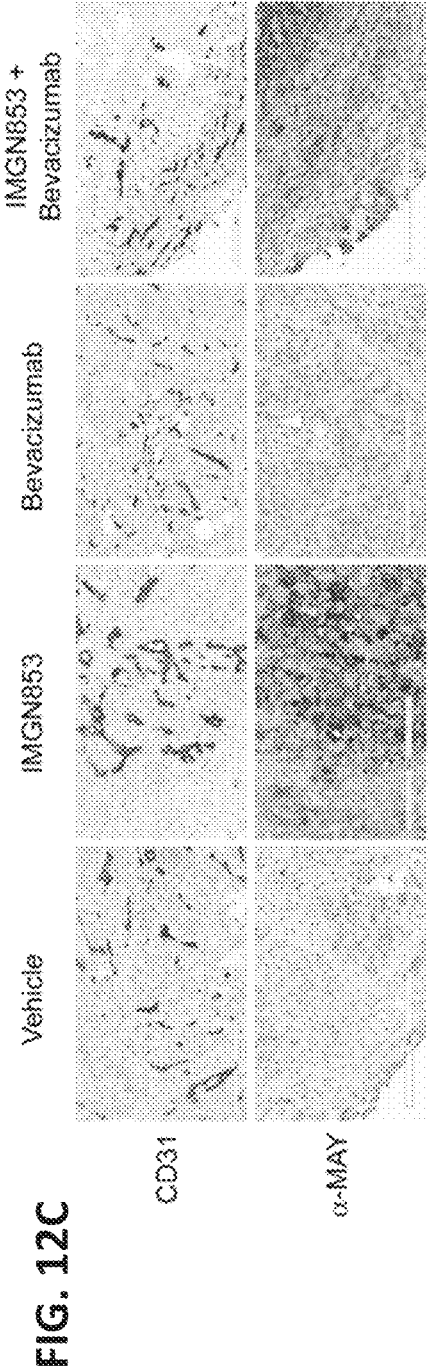
FIG. 12C shows immunohistochemical evaluation of CD31 expression (upper panel) and maytansine detection (anti-MAY; lower panel) in tumor tissues on day 4. For each group, representative micrographs from one of three tumors are shown. Original magnification, 20×; scale bars, 200 µm.

The IMGN853-Bevacizumab Combination Induces Rapid Microvascular Disruption and Extensive Necrotic Damage in OV-90 Xenografts To advance the mechanistic understanding of the superior efficacy seen with the IMGN853 in the presence of bevacizumab in vivo, OV-90 tumors from animals treated with either IMGN853 (2.5 mg/kg), bevacizumab (5 mg/kg), or the combination were harvested 4 days post-dosing and examined (FIGS. 12A-12C). It is noteworthy that combination therapy completely arrested tumor growth at this early time point, as measured by changes in tumor volumes, in contrast to only delays seen with corresponding single agent dosing (e.g. see FIG. 2B). Histological (H&E) staining revealed that tumors from combination-treated mice were structurally comprised of large necrotic cores surrounded by a smaller rim of viable cells at the periphery (FIG. 12A). This extent of cellular destruction was not observed in any of the other treatment groups, and it is consistent with the rapid tumor stabilization conferred by the dosing regimen. Next, as a pharmacodynamic readout, tumor γH2AX levels were measured by immunoblotting (FIG. 12B). As expected, γH2AX expression was negligible in tumors from vehicle-treated mice but was robustly induced following single-agent IMGN853 treatment. Consistent with the observed improvements in antitumor activity, the addition of bevacizumab to IMGN853 resulted in further elevations in γH2AX levels relative to those seen with IMGN853 monotherapy.

Interestingly, γH2AX upregulation was also observed in tumors following bevacizumab exposure alone, albeit to a lesser degree than IMGN853 (FIG. 12B). While genotoxic insults are the primary inducers of γH2AX, accumulation of this protein can also occur in response to hypoxia. This result, therefore, suggested that increased hypoxic conditions arising from bevacizumab-induced vascular disruption were contributing to the amplified DNA damage profile. In order to examine treatment-related effects on microvessels, immunohistochemical staining with the endothelial cell marker CD31 was performed (FIG. 12C, upper panel). Tumors from control and IMGN853-treated mice had numerous large vessels, which were decreased in size and showed loss of luminal integrity following bevacizumab treatment. Notably, dual IMGN853 and bevacizumab administration led to marked changes in the tumor microvasculature. These included a clear reduction in the number of large branched vascular structures, with the smaller CD31-stained areas lacking clear lumens and predominantly localized to the peripheral rim regions. Additional staining of corresponding tissue samples with an anti-maytansine antibody confirmed tumor-directed delivery of IMGN853 in mice treated with ADC-containing regimens (FIG. 12C, lower panel).

Without wishing to be bound by theory, it is possible that the presence of bevacizumab promotes better tumor penetration and exposure to the ADC, resulting in more effective eradication of tumor cells. In this regard, it is well established that bevacizumab treatment can induce normalization of the tumor vasculature, an effect that has been suggested to result in reduced interstitial pressures and improved drug delivery. However, there are preclinical and clinical observations of reduced tumor uptake of both chemotherapeutic drugs and antibodies following antiangiogenic therapy.

It is to be appreciated that the Detailed Description section, and not the Summary and Abstract sections, is intended to be used to interpret the claims. The Summary and Abstract sections sets forth one or more, but not all, exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for treating a patient having a FOLR1-expressing cancer comprising administering to said patient in need thereof bevacizumab in combination with an immunoconjugate that binds to folate receptor 1 (FOLR1), wherein said immunoconjugate comprises an antibody or antigen-binding fragment thereof comprising a heavy chain variable region (VH) complementary determining region (CDR)1 sequence of SEQ ID NO:9, a VH CDR2 sequence of SEQ ID NO:10, and a VH CDR3 sequence of SEQ ID NO:12, and a light chain variable region (VL) CDR1 sequence of SEQ ID NO:6, a VL CDR2 sequence of SEQ ID NO:7, and a VL CDR3 sequence of SEQ ID NO:8, wherein said immunoconjugate comprises a maytansinoid;
   wherein the maytansinoid is linked to the antibody or antigen-binding fragment thereof by sulfo-N-succinimidyl 4-(2-pyridyldithio)butanoate (sulfo-SPDB);
   wherein the immunoconjugate is administered once every three weeks at a dose of 5 mg/kg adjusted ideal body weight (AIBW) or 6 mg/kg AIBW, and wherein the bevacizumab is administered once every three weeks at a dose of 15 mg/kg; and
   wherein the cancer has previously been treated with bevacizumab.

2. The method of claim 1, wherein the immunoconjugate that binds to FOLR1 comprises an antibody or antigen-binding fragment thereof that comprises a VH comprising the sequence of SEQ ID NO:3 and a VL comprising the sequence of SEQ ID NO:5, wherein the maytansinoid is DM4, and wherein immunoconjugate is administered once every three weeks at a dose of 6 mg/kg AIBW.

3. The method of claim 2, wherein the immunoconjugate is administered once every three weeks at a dose of 6 mg/kg AIBW.

4. The method of claim 1, wherein the immunoconjugate comprises an antibody comprising (i) a heavy chain comprising the same amino acid sequence as the amino acid sequence of the heavy chain encoded by the plasmid deposited with the American Type Culture Collection (ATCC) as PTA-10772 and (ii) a light chain comprising the same amino acid sequence as the amino acid sequence of the light chain encoded by the plasmid deposited with the ATCC as PTA-10774, and the cytotoxin DM4, and wherein immunoconjugate is administered once every three weeks at a dose of 6 mg/kg AIBW.

5. The method of claim 1, which further comprises administration of a steroid to the patient, wherein the steroid is administered as an eye drop.

6. The method of claim 1, wherein the cancer is ovarian cancer, peritoneal cancer, fallopian cancer, endometrial cancer, or lung cancer.

7. The method of claim 6, wherein the ovarian cancer is platinum-resistant epithelial ovarian cancer.

8. The method of claim 1, wherein FOLR1 expression in the cancer is measured by immunohistochemistry (IHC).

9. The method of claim 8, wherein at least 50% of cells in a sample obtained from the patient have an IHC score of at least 2.

10. The method of claim 8, wherein at least 75% of cells in a sample obtained from the patient have an IHC score of at least 2.

11. The method of claim 8, wherein at least 50% of cells in a sample obtained from the patient have an IHC score of at least 3.

12. The method of claim 8, wherein at least 75% of cells in a sample obtained from the patient have an IHC score of at least 3.

13. The method of claim 1, wherein the immunoconjugate and the bevacizumab are administered in separate pharmaceutical compositions.

14. The method of claim 1, wherein the cancer is primary platinum refractory cancer or platinum resistant cancer.

15. The method of claim 1, wherein the cancer is platinum sensitive cancer.

16. The method of claim 1, wherein the administration is selected from the group consisting of a first-line therapy, a second-line therapy, a third-line therapy, a fourth-line therapy, and a fifth-line therapy.

17. A method for treating a patient having a FOLR1-expressing cancer comprising administering to said patient in need thereof bevacizumab in combination with an immunoconjugate that binds to folate receptor 1 (FOLR1), wherein said immunoconjugate comprises an antibody or antigen-binding fragment thereof comprising a heavy chain variable region (VH) complementary determining region (CDR)1 sequence of SEQ ID NO:9, a VH CDR2 sequence of SEQ ID NO:10, and a VH CDR3 sequence of SEQ ID NO:12, and a light chain variable region (VL) CDR1 sequence of SEQ ID NO:6, a VL CDR2 sequence of SEQ ID NO:7, and a VL CDR3 sequence of SEQ ID NO:8, wherein said immunoconjugate comprises a maytansinoid,
   wherein the maytansinoid is linked to the antibody or antigen-binding fragment thereof by sulfo-N-succinimidyl 4-(2-pyridyldithio)butanoate (sulfo-SPDB), and
   wherein the immunoconjugate is administered once every three weeks at a dose of 6 mg/kg AIBW, wherein the cancer is platinum-resistant epithelial ovarian cancer (EOC), and wherein the immunoconjugate and the bevacizumab are administered in separate pharmaceutical compositions.

18. The method of claim 17, wherein the cancer has not previously been treated with bevacizumab.

19. The method of claim 17, wherein FOLR1 expression in the cancer is measured by immunohistochemistry (IHC).

20. The method of claim 19, wherein at least 50% of cells in a sample obtained from the patient have an IHC score of at least 2.

21. The method of claim 19, wherein at least 75% of cells in a sample obtained from the patient have an IHC score of at least 2.

22. The method of claim 17, which further comprises administration of a steroid to the patient, wherein the steroid is administered as an eye drop.

23. The method of claim 17, wherein the maytansinoid is DM4.

24. The method of claim 23, wherein the immunoconjugate that binds to FOLR1 comprises an antibody or antigen-binding fragment thereof that comprises a VH comprising the sequence of SEQ ID NO:3 and a VL comprising the sequence of SEQ ID NO:5.

25. The method of claim 17, wherein the immunoconjugate comprises an antibody comprising (i) a heavy chain comprising the same amino acid sequence as the amino acid sequence of the heavy chain encoded by the plasmid deposited with the American Type Culture Collection (ATCC) as PTA-10772 and (ii) a light chain comprising the same amino acid sequence as the amino acid sequence of the light chain encoded by the plasmid deposited with the ATCC as PTA-10774, and the cytotoxin DM4.

* * * * *